US012780859B2

(12) United States Patent
Zhang

(10) Patent No.: US 12,780,859 B2
(45) Date of Patent: Nov. 3, 2026

(54) CLASS OF PLATINUM COMPOUNDS FOR TREATING CANCER, AND METHOD FOR PREPARATION THEREOF

(71) Applicant: SHANGHAI HAIJU BIOLOGICAL TECHNOLOGY CO., LTD., Shanghai (CN)

(72) Inventor: Ruling Zhang, Shanghai (CN)

(73) Assignee: SHANGHAI HAIJU BIOLOGICAL TECHNOLOGY CO., LTD., Shanghai (CN)

( * ) Notice: Subject to any disclaimer, the term of this patent is extended or adjusted under 35 U.S.C. 154(b) by 808 days.

(21) Appl. No.: 18/025,695

(22) PCT Filed: Sep. 11, 2020

(86) PCT No.: PCT/CN2020/114659
§ 371 (c)(1),
(2) Date: Mar. 10, 2023

(87) PCT Pub. No.: WO2022/052014
PCT Pub. Date: Mar. 17, 2022

(65) Prior Publication Data

US 2023/0339997 A1 Oct. 26, 2023

(51) Int. Cl.

| | |
|---|---|
| ***A61P 35/00*** | (2006.01) |
| ***A61K 47/64*** | (2017.01) |
| ***A61K 47/68*** | (2017.01) |
| ***C07F 15/00*** | (2006.01) |
| ***C07K 5/08*** | (2006.01) |

(52) U.S. Cl.
CPC ...... *C07F 15/0093* (2013.01); *A61K 47/6425* (2017.08); *A61K 47/643* (2017.08); *A61K 47/6851* (2017.08); *A61P 35/00* (2018.01); *C07K 5/0827* (2013.01)

(58) Field of Classification Search
CPC ............ C07F 15/0093; A61K 47/6425; A61K 47/643; A61K 47/6851; A61P 35/00; C07K 5/0827
See application file for complete search history.

(56) References Cited

U.S. PATENT DOCUMENTS

2006/0089341 A1 4/2006 Kratz et al.
2015/0368281 A1 12/2015 Chen et al.
2016/0317549 A1* 11/2016 Bilodeau et al. .... A61K 31/555 548/403
2018/0104353 A1* 4/2018 Sengupta et al. ...... A61K 47/60 514/492
2018/0154018 A1* 6/2018 Yurkovetskiy et al. .................... A61K 47/6889 530/328
2019/0216858 A1* 7/2019 Law ....................... A61K 35/34 424/93

FOREIGN PATENT DOCUMENTS

CN 104610415 A 5/2015
CN 104768962 A 7/2015
CN 108368143 A 8/2018
KR 20100107961 A * 10/2010 ............ A61K 38/12
WO 2014075391 A1 5/2014
WO 2017097986 A1 6/2017

OTHER PUBLICATIONS

KR 20100107961 A (Hong et al.; English language machine translation) (Year: 2010).*
Drug Des. Dev. Ther. 2017, 11, 599-616 (Ndagi et al.) (Year: 2017).*
Webster's New Collegiate Dictionary, 1961, p. 136 (definition of "certain") (Year: 1961).*
J. Struct. Biol. 2006, 155, 38-44 (Hall et al.) (Year: 2006).*
Jun. 10, 2021 International Search Report issued in International Patent Application No. PCT/CN2020/114659.
Jun. 10, 2021 Written Opinion of the International Searching Authority issued in International Patent Application No. PCT/CN2020/114659.
Wang, Xing et al., A trifunctional Pt(II) complex alleviates the NHEJ/HR-related DSBs repairs to evade cisplatin-resistance in NSCLC, Bioorganic Chemistry, vol. 104, Sep. 1, 2020, pp. 1-14, Fig. 1, abstract, Table 1.
Warnecke, Andre et al., Synthesis and Biological Activity of Water-Soluble Maleimide Derivatives of the Anticancer Drug Carboplatin Designed as Albumin-Binding Prodrugs, Bioconjugate Chem., vol. 15, Dec. 31, 2004, pp. 1349-1359, and scheme 4.

* cited by examiner

*Primary Examiner* — Amy C Bonaparte
*Assistant Examiner* — Derek Rhoades

(57) ABSTRACT

Provided is the novel class of platinum compounds shown in formula (I), and their use as pharmaceutical agents, especially for treating cancer alone or in combination and for preventing cancer. The described novel platinum compounds have been shown, through experimentation, to have superior in vivo antitumor effects, significantly better than the clinical drug carboplatin, and to have significantly improved the aqueous solubility of platinum-based drugs, and can be made into lyophilized powder or injectable solution, resolving the defect of inconvenient clinical use. In view of the foregoing, the disclosed class of platinum compounds has good prospects for clinical application.

(I)

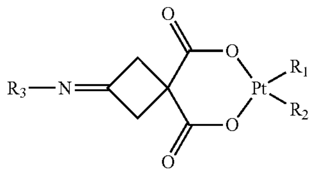

19 Claims, No Drawings

CLASS OF PLATINUM COMPOUNDS FOR TREATING CANCER, AND METHOD FOR PREPARATION THEREOF

The present application is a National Stage of International Application No. PCT/CN2020/114659, filed on Sep. 11, 2020.

TECHNICAL FIELD

The present disclosure relates to a novel class of platinum anticancer compounds and a preparation method thereof, belonging to the field of chemical pharmacy.

BACKGROUND

Cancer is a disease that seriously threatens human health and life. In 2015, there were 4.3 million new cancer cases and 2.8 million deaths in China. The number of cancer cases and deaths in China has ranked the first in the world. About 10000 people are diagnosed with cancer every day, with an average of 7 people every minute. Cancer has become one of the medical problems that human beings urgently need to overcome.

Currently, there are three main means of treating cancer: surgical treatment, radiotherapy and chemotherapy. The basis of chemotherapy is chemotherapy drugs, and countries all over the world invest a lot of manpower, materials and financial resources in the research of anticancer drugs every year. The application of platinum drugs in clinical cancer treatment originated in 1969, when Rosenberg et al. discovered the promising anticancer activity of platinum (II) complex cisplatin. Platinum drugs represented by cisplatin, carboplatin and oxaliplatin and the like are widely used as the first choice for the treatment of many tumors due to their strong anticancer activity and wide spectrum of action. According to the latest statistics, 85% of the combined chemotherapy schemes currently used in clinical use are mainly platinum antitumor drugs as the main drugs, or platinum antitumor drugs are involved in the compatibility.

Studies have shown that platinum drugs have the defect of poor water solubility. The water solubility of cisplatin is 1.0 mg/mL, that of carboplatin is 17.0 mg/mL, and that of oxaliplatin is 6.0 mg/mL, which has brought many adverse effects on the stability and clinical application of pharmaceutical preparations. The poor water solubility of platinum drugs also directly affects the accumulation and metabolism of drugs in the body, resulting in their accumulation in kidney tissue and blood, which can not be excreted by the body in time, and it is easy to produce cumulative poisoning.

A large number of clinical trials have confirmed that antitumor angiogenesis is crucial in the treatment of cancer and is a key link in the process of inhibiting tumor growth. Tumor angiogenesis is regulated by various protein molecules in the integrin family, such as αvβ3, αvβ6, α5β1, etc. Integrin, first proposed by Richard in 1987, is a kind of heterodimeric transmembrane glycoprotein composed of α and β subunits. At present, at least 25 kinds of a subunits and 11 kinds of β subunits are known, and the two are connected to each other to form more than 20 different integrin molecules. Integrin is an extracellular matrix receptor, in which integrin αvβ3 is highly expressed on the surface of neovascular endothelial cells, neuroblastoma, osteosarcoma, glioblastoma, breast cancer, prostate cancer and other tumor cells, but not expressed or expressed at very low levels in existing blood vessels and normal tissues; integrin αvβ6 is up-regulated in pancreatic cancer, breast cancer, lung cancer, oral and skin squamous cell carcinoma, colon cancer, gastric cancer and endometrial cancer, and down regulated in normal adults; integrin α5β1 is highly expressed in colorectal cancer, breast cancer, ovarian cancer, lung cancer, gastric cancer, glioma and other tumors, but not expressed or expressed at low levels in mature normal cells and blood vessels. The highly restricted expression in the process of tumor growth and metastasis makes integrin a very favorable target for tumor targeted therapy.

CONTENT OF THE PRESENT INVENTION

The present disclosure discloses a novel class of platinum compounds represented by formula (I), and a use thereof as a medicament, particularly a medicament for treating, preventing cancer alone or in combination.

(I)

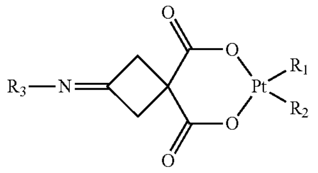

The present disclosure discloses a novel class of platinum compounds represented by formula (I). Compared with the antitumor platinum compounds of the prior art, the solubility and in vivo tumor inhibition activity of the platinum compounds disclosed in the present disclosure are greatly improved, resulting in unexpected technical effects.

(I)

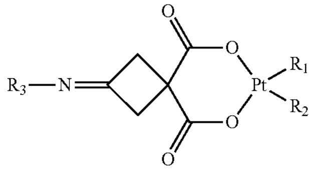

The present disclosure provides a compound represented by the following formula (I) or a pharmaceutically acceptable salt thereof, (I)

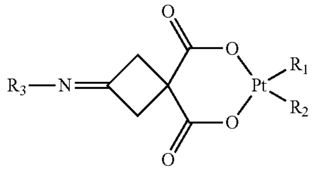

wherein:

$R_1$ and $R_2$ are linked together to form the following structure:

(A1)

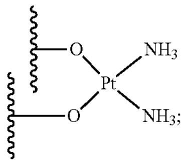

;

(A2)

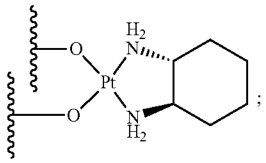

;

(A3)

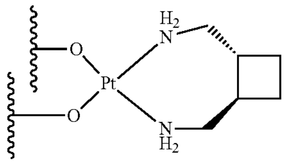

;

(A4)

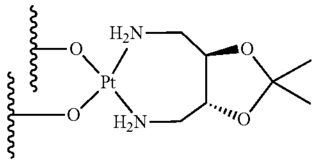

;

(A5)

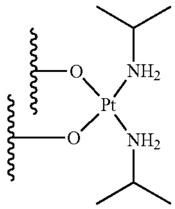

;

(A6)

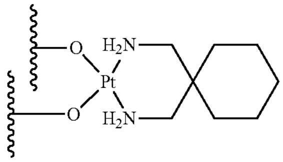

;

(A7)

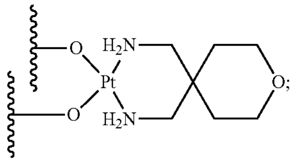

; or (A8)

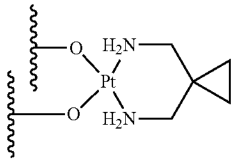

;

$R_3$ is a group with certain functionalities, which is characterized in that $R_3$ is able to effectively enhance the targeting or water solubility of platinum compounds.

In some embodiments of the present disclosure, $R_1$ and $R_2$ are linked together to form moiety (A1), (A2), (A3) or (A4):

(A1)

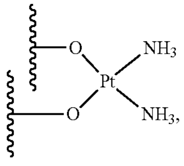

, (A2)

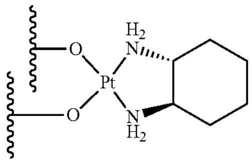

;

(A3)

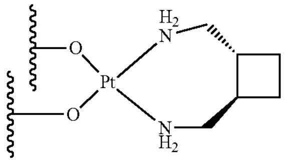

;

(A4)

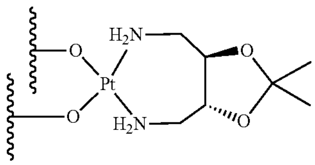

.

In some embodiments of the present disclosure, $R_1$ and $R_2$ are linked together to form moiety (A1), and the general formula of this series of platinum compounds is:

I-A1

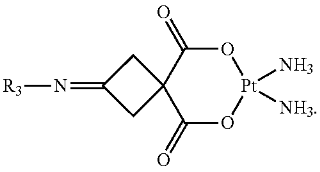

.

In some embodiments of the present disclosure, $R_1$ and $R_2$ are linked together to form moiety (A2), and the general formula of this series of platinum compounds is:

I-A2

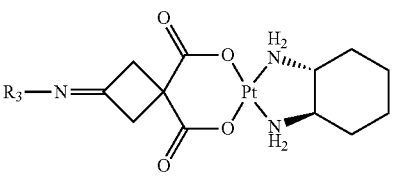

.

In some embodiments of the present disclosure, $R_1$ and $R_2$ are linked together to form moiety (A3), and the general formula of this series of platinum compounds is:

I-A3

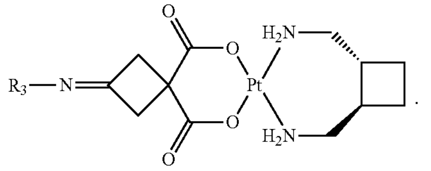

In some embodiments of the present disclosure, $R_1$ and $R_2$ are linked together to form moiety (A4), and the general formula of this series of platinum compounds is:

I-A4

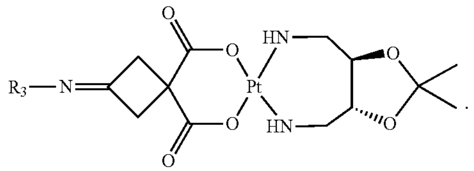

In some embodiments of the present disclosure, $R_3$ is a group with certain functionalities, which is characterized in that $R_3$ is able to effectively enhance the targeting or water solubility of platinum compounds;

$R_3$ is the following structure:

R3-1

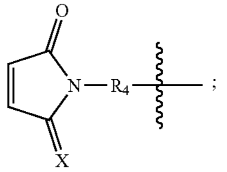

R3-2

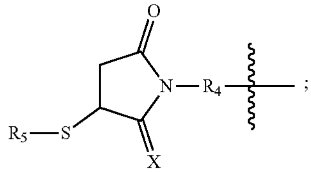

or

R3-3

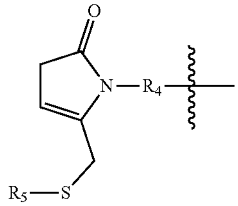

wherein, X is C or O; $R_4$ is a linker, which has the function of improving the water solubility of the compound; $R_5$ is a group with targeting function.

In some embodiments of the present disclosure, $R_4$ is selected from: $C_{1-12}$ alkyl, $C_{1-12}$ alkoxy, $C_{1-12}$ alkylcarbonyl, phenoxy or phenylamino optionally substituted by 1 to 2 halogens, $C_{1-12}$ alkylamino, $C_{1-12}$ alkoxy-$C_{1-12}$ alkylamino, $C_{1-12}$ alkylcarbonyloxy, $C_{1-12}$ alkyl-$C_{3-8}$ cycloalkylcarbonyloxy, $(C_{1-4}$ alkyl-O$)_m$—$C_{1-12}$ alkylcarbonyloxy, $C_{1-12}$ alkylcarbonylamino-$(C_{1-4}$ alkyl-O$)_m$—$C_{1-12}$ alkylcarbonyloxy, $C_{1-12}$ alkylcarbonylamino and phenyl-$C_{1-12}$ alkylcarbonylamino.

In some embodiments of the present disclosure, $R_4$ is the following structure:

R4-1

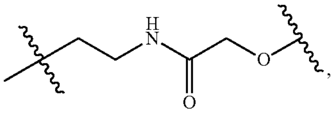

R4-2

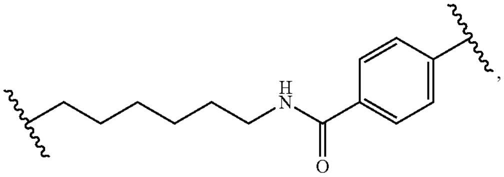

R4-3

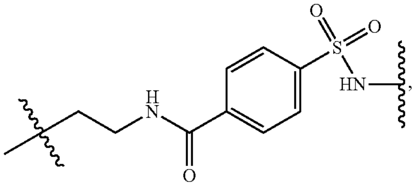

R4-4

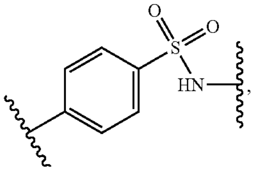

R4-5

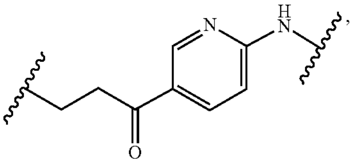

R4-6

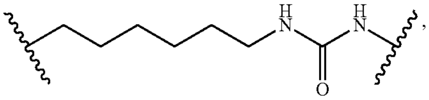

R4-7

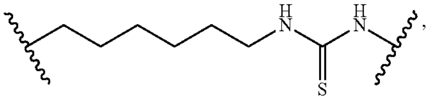

R4-8

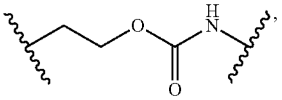

R4-9

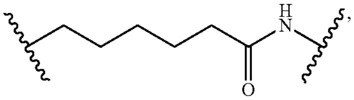

R4-10

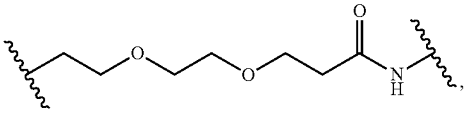

-continued

R4-11

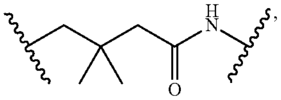

R4-12

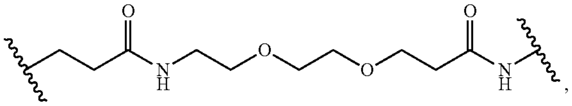

R4-13

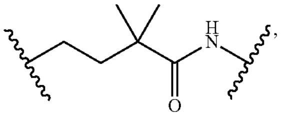

R4-14

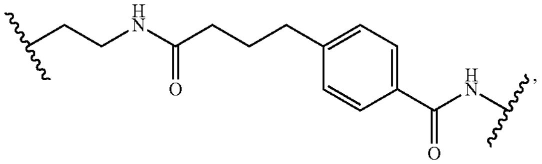

R4-15

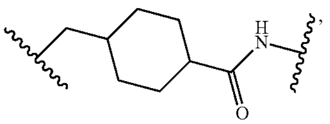

R4-16

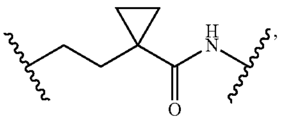

-continued

R4-17

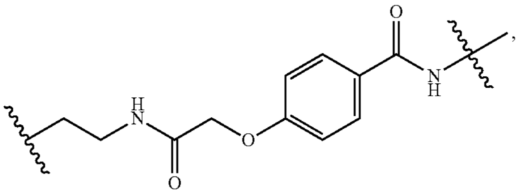

or

R4-18

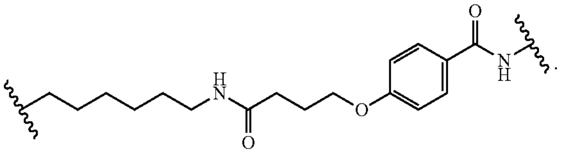

In some embodiments of the present disclosure, $R_5$ is: human serum albumin HAS; an antibody that binds to a tumor-associated antigen, such as an anti-folate receptor α antibody, an anti-mesothelin antibody, an anti-Her2 antibody, an anti-EGFR antibody, an anti-VEGFR antibody, an anti-CD20 antibody, an anti-CD22 antibody, an anti-CD28 antibody, an anti-CD33 antibody, an anti-BR96 antibody; or, a molecule that is able to specifically bind to a tumor cell surface integrin receptor.

In some embodiments of the present disclosure, $R_5$ is the molecule that is able to specifically bind to the tumor cell surface integrin receptor, wherein the integrin receptor includes, but is not limited to, αvβ3, αvβ6, α5β1.

In some embodiments of the present disclosure, $R_5$ is the molecule that is able to specifically bind to an integrin, and comprises an arginine-glycine-aspartic acid (RGD) tripeptide sequence in chemical structure, preferably but not limited to the following structures:

R5-1

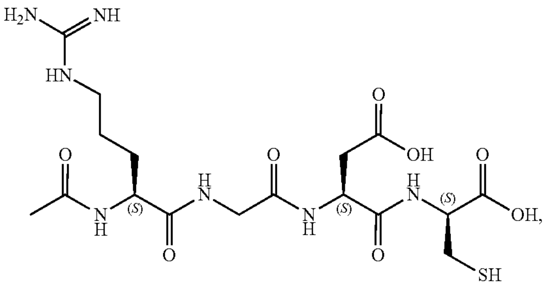

Ac-RGDC

R5-2

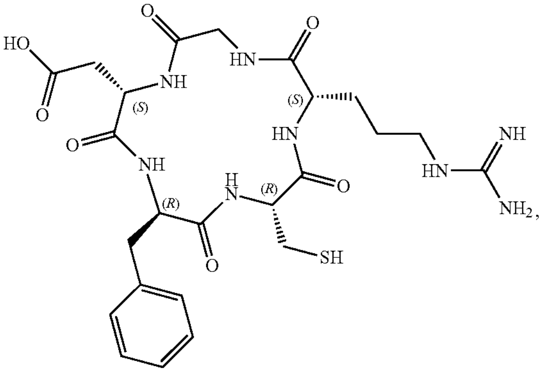

cyclo(RGDfC)

-continued
R5-3
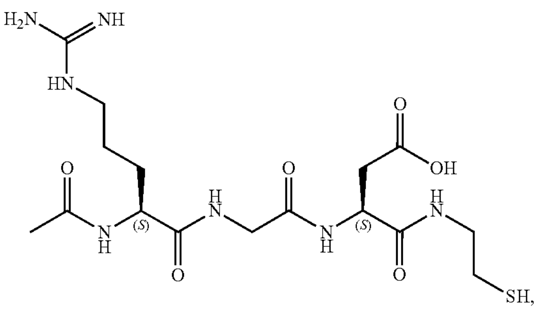
Ac-RGD-CONH—CH2CH2—SH
R5-4
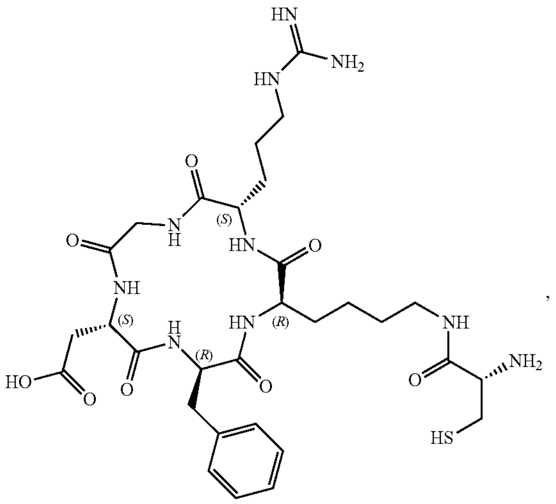
cyclo(RGDfK-C)
R5-5
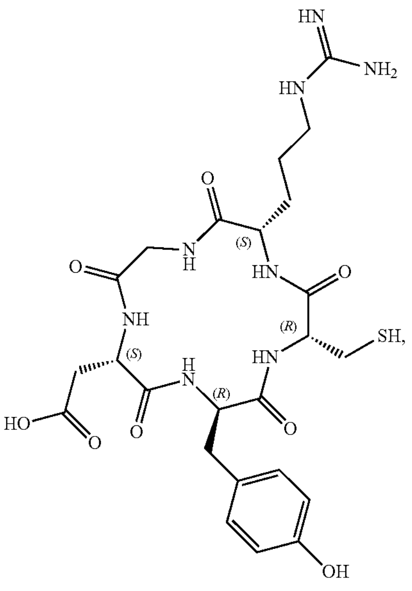
cyclo(RGDyC)
R5-6
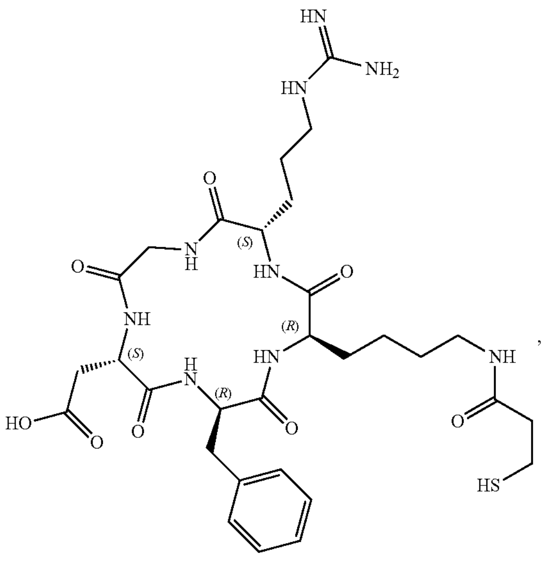
cyclo(RGDfK-NHCO—CH2CH2—SH)

-continued
R5-7
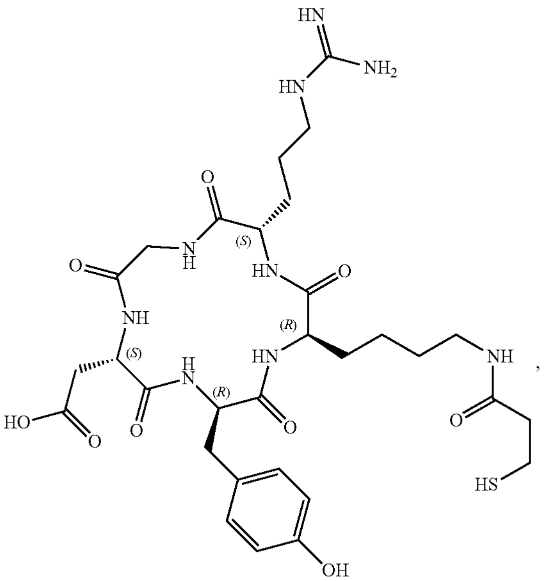
cyclo(RGDyK-NHCO—CH2CH2—SH)
,
R5-8
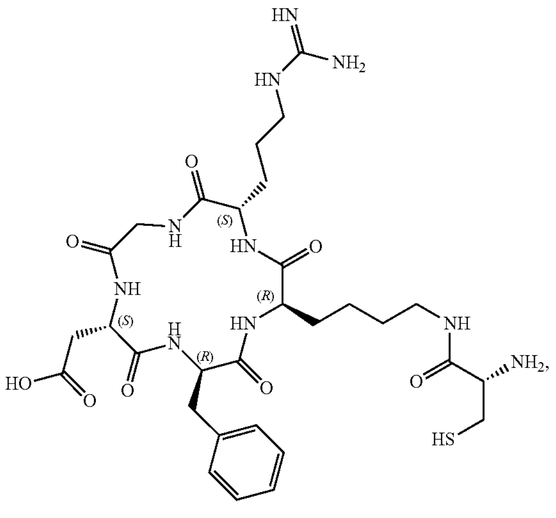
cyclo(RGDyK-C)
R5-9
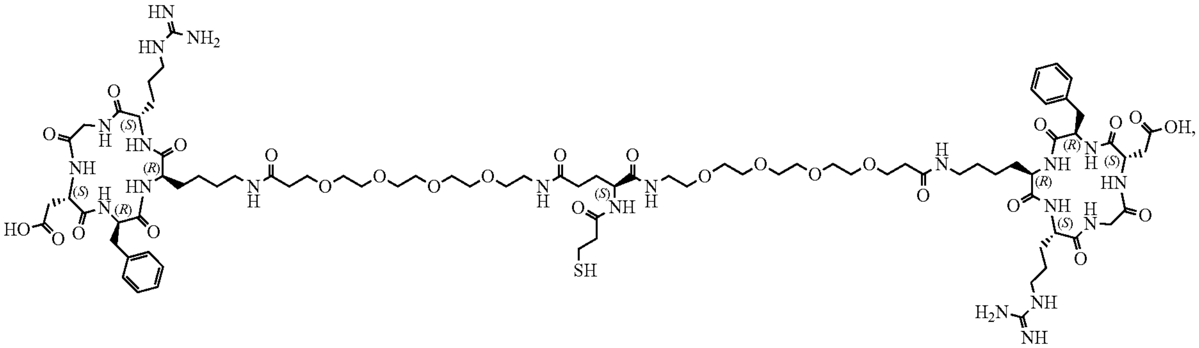
E[peg4-cyclo(RGDfK)]2-NHCO—CH2CH2—SH
R5-10
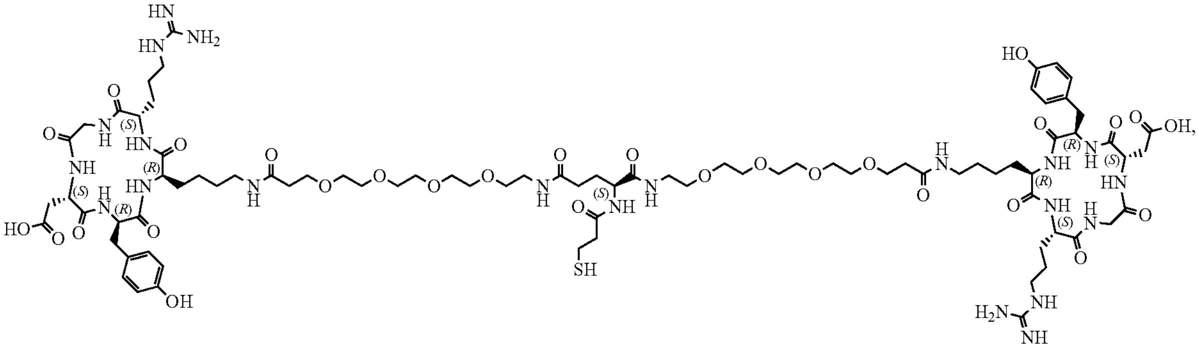
E[peg4-cyclo(RGDyK)]2-NHCO—CH2CH2—SH In some embodiments of the present disclosure, the general structure formula is shown in any one of the following structures:
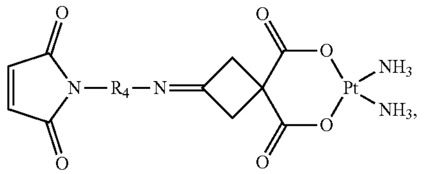
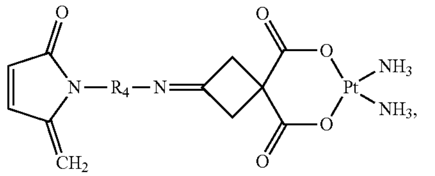
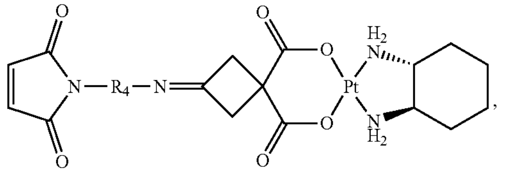
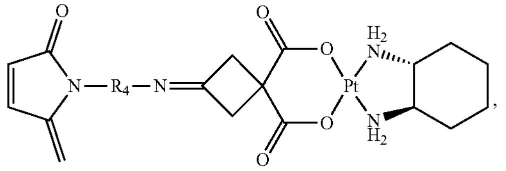
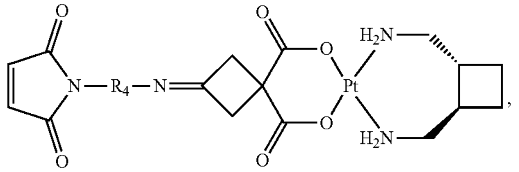
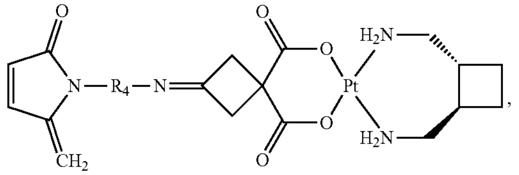
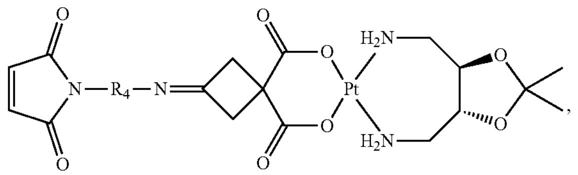
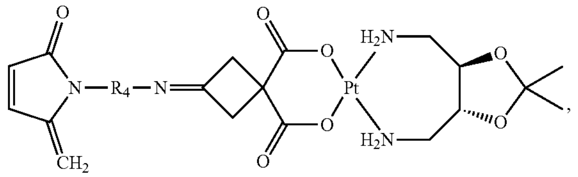
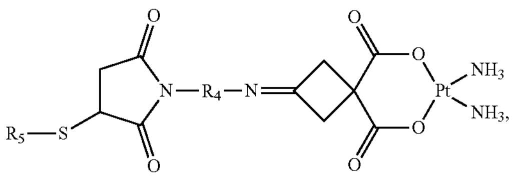
-continued
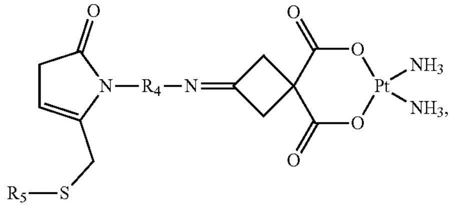
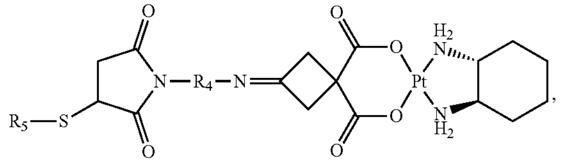
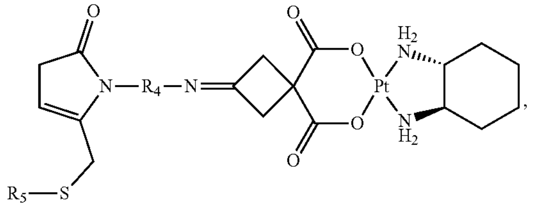
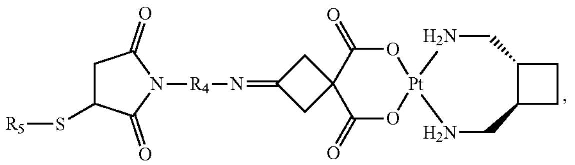
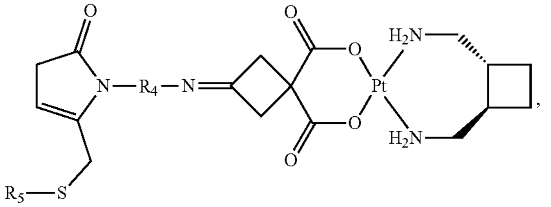
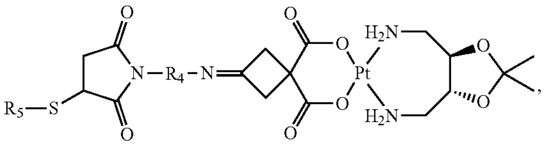
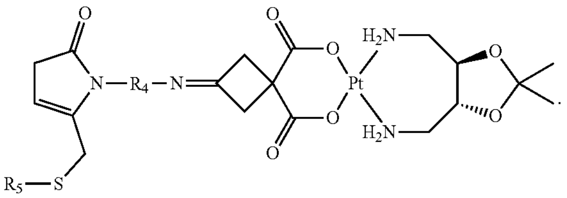
In some embodiments of the present disclosure, the compound represented by formula (I) is:

S1
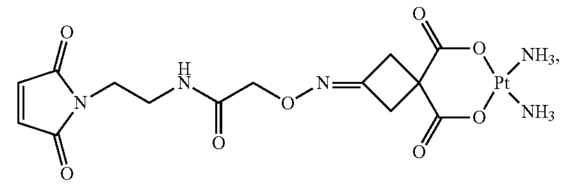
S2
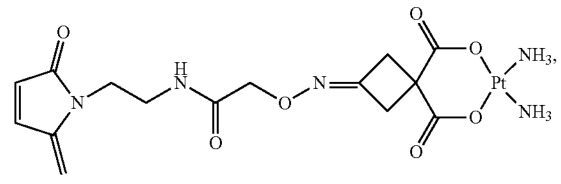
S3
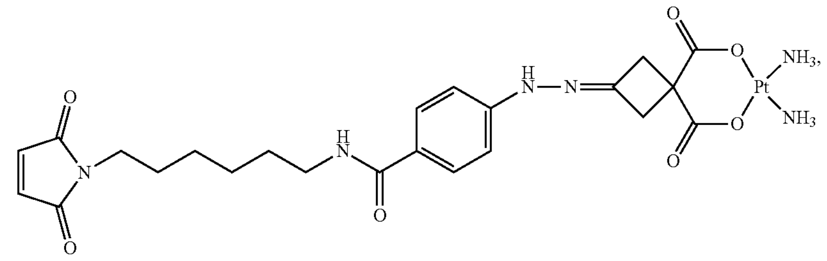
S4
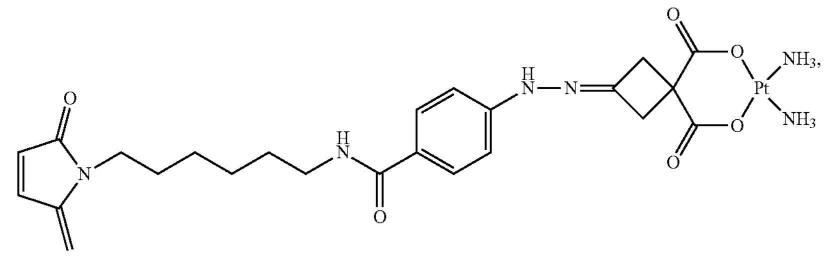
S5
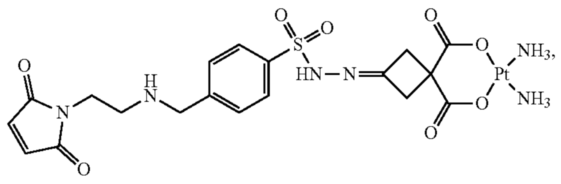
S6
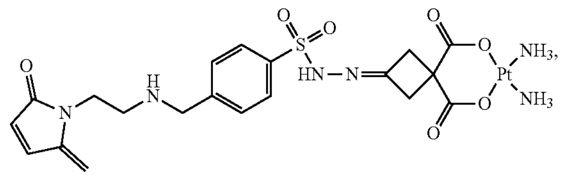
S7
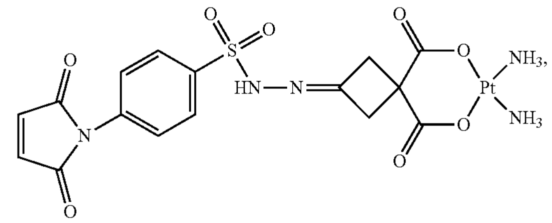
S8
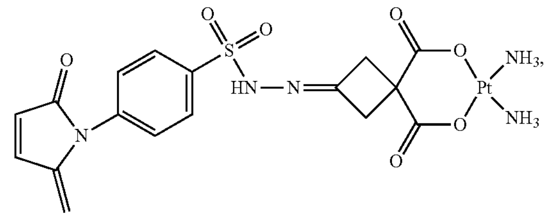
S9
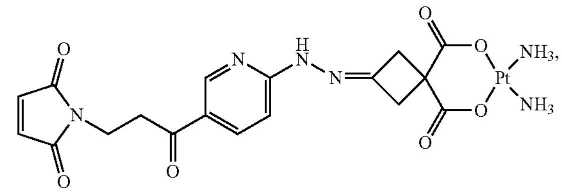
S10
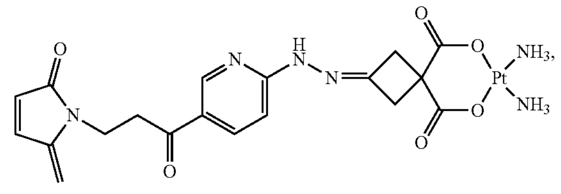
S11
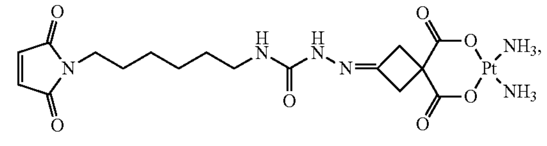
S12
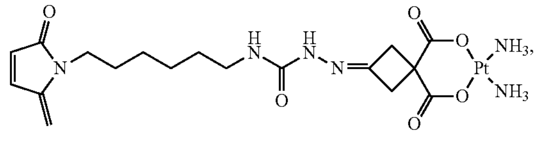

-continued
S13
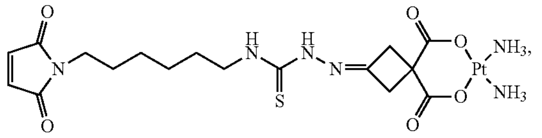
S14
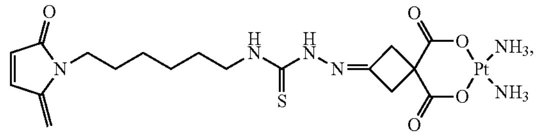
S15
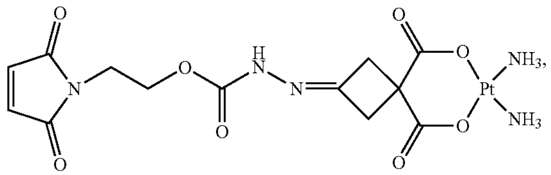
S16
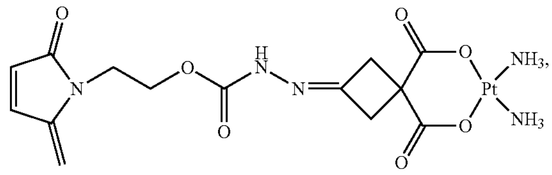
S17
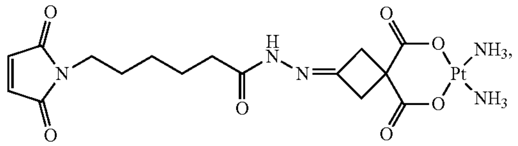
S18
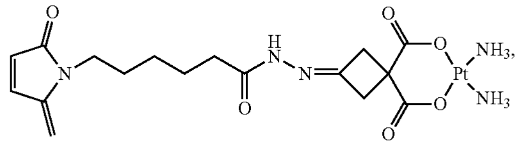
S19
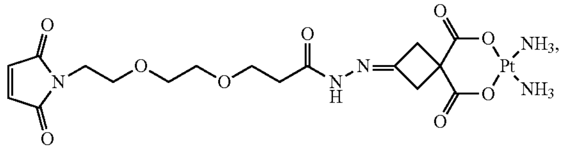
S20
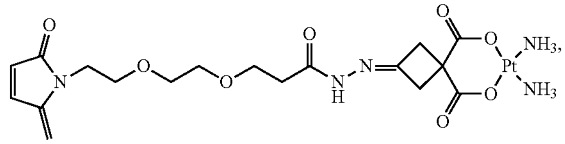
S21
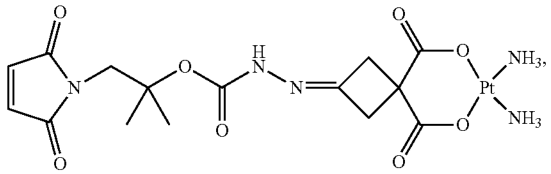
S22
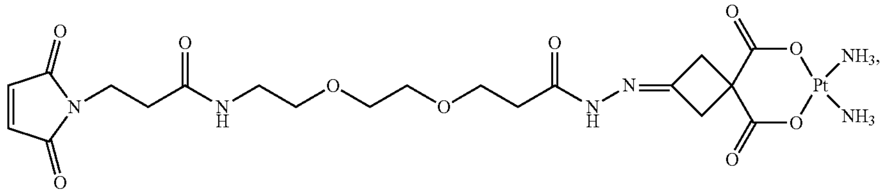
S23
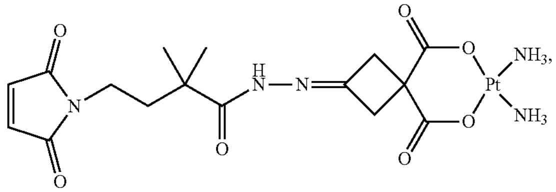
S24
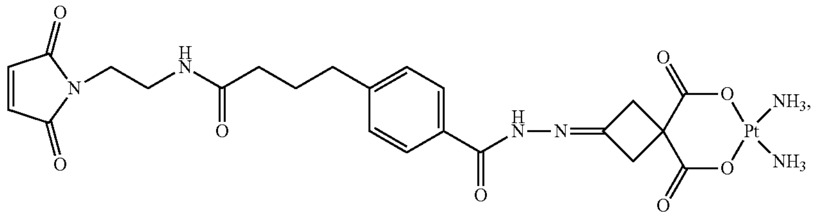

-continued
S25
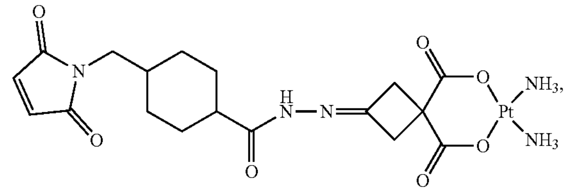
S26
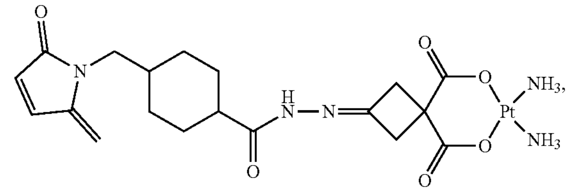
S27
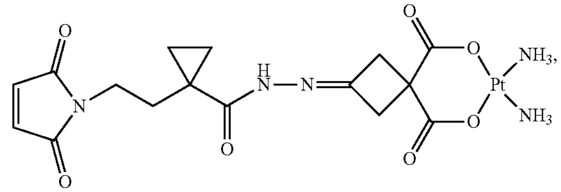
S28
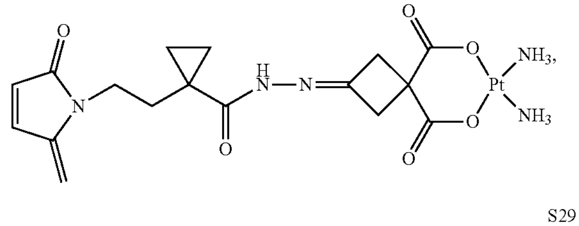
S29
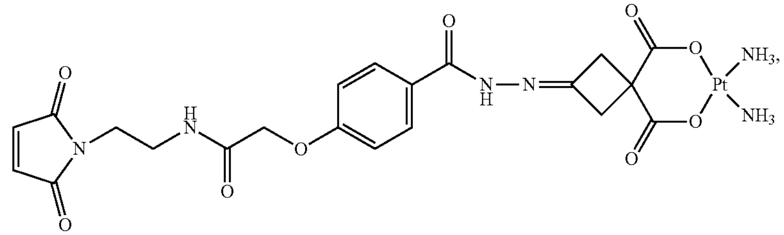
S30
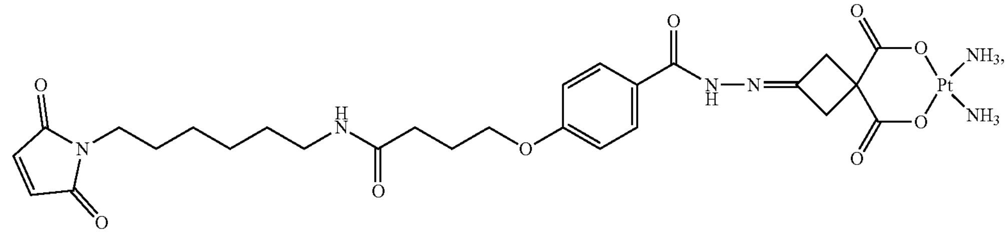
S31
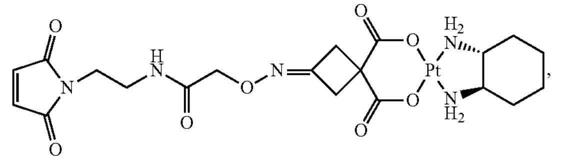
S32
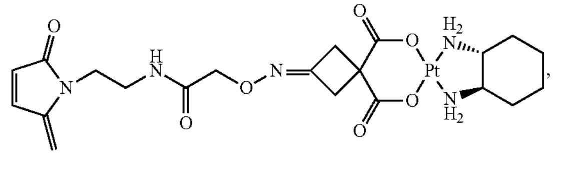
S33
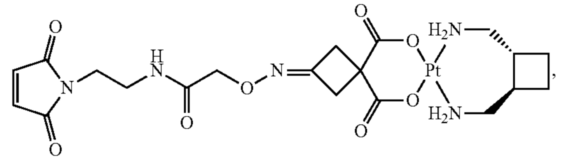
S34
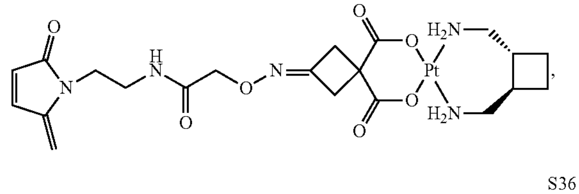
S35
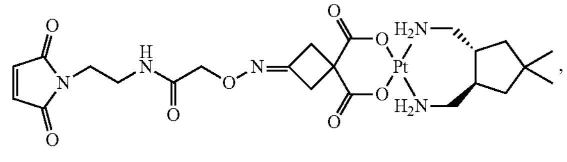
S36
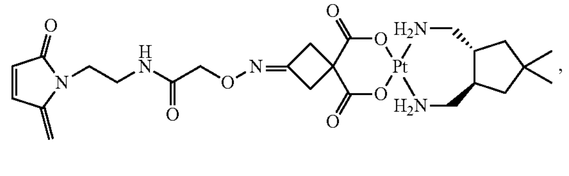

-continued
S37
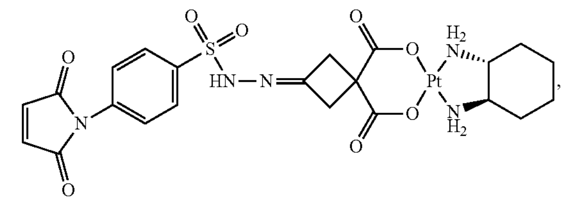,
S38
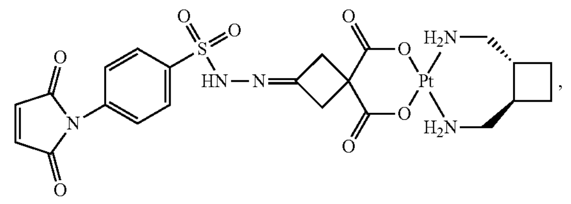,
S39
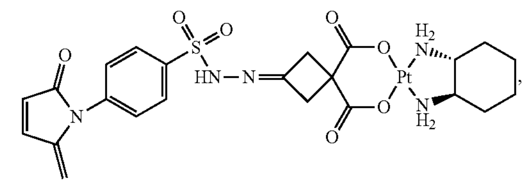,
S40
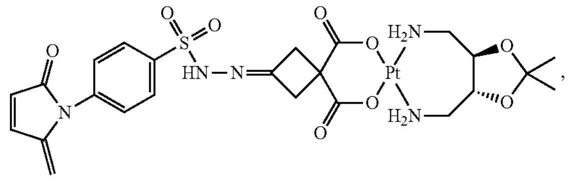,
S41
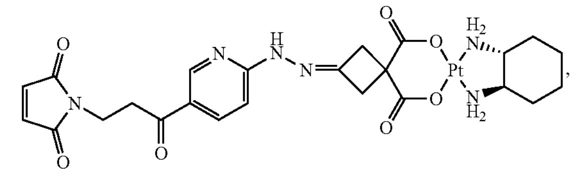,
S42
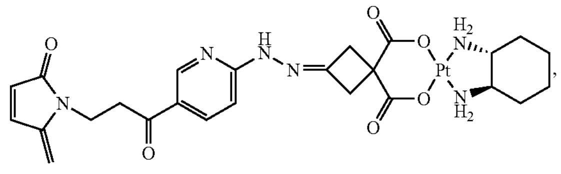,
S43
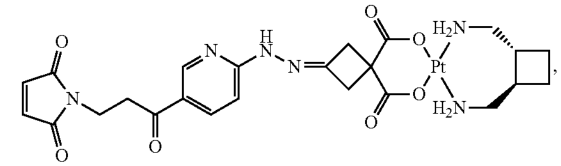,
S44
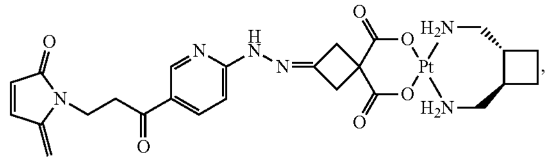,
S45
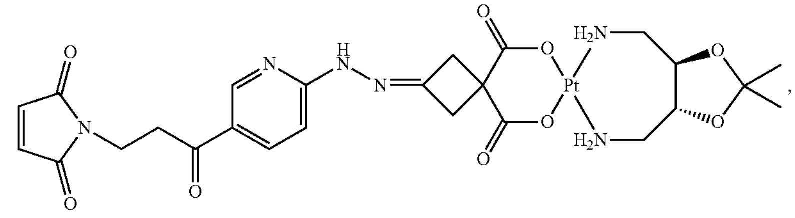,
S46
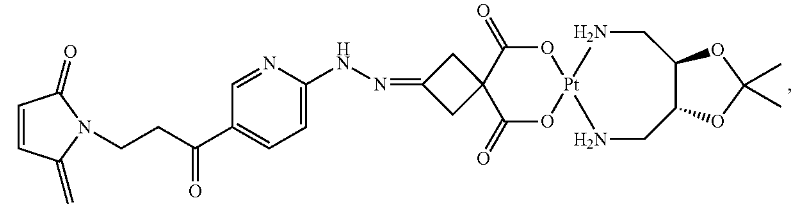,
S47
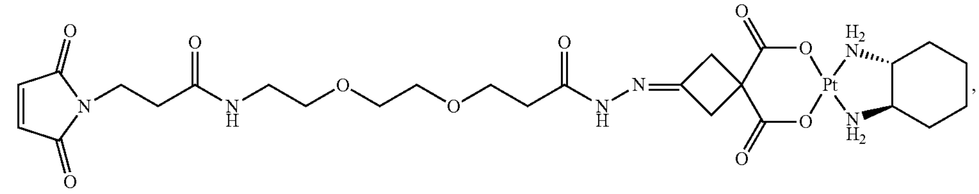, -continued
S48
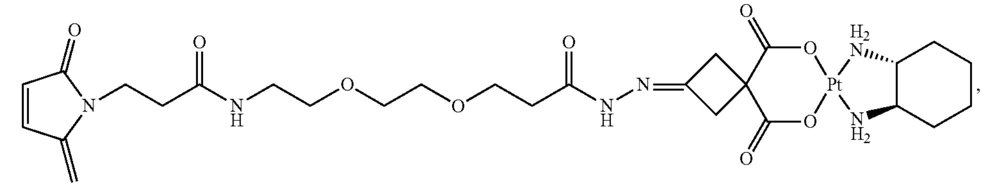
S49
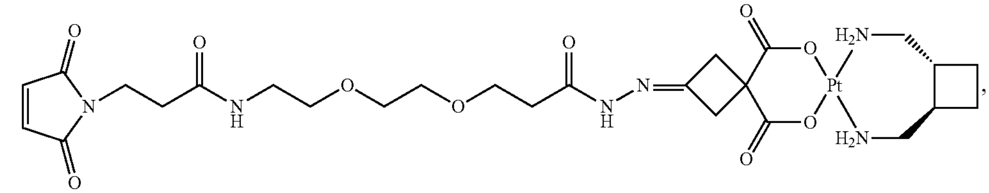
S50
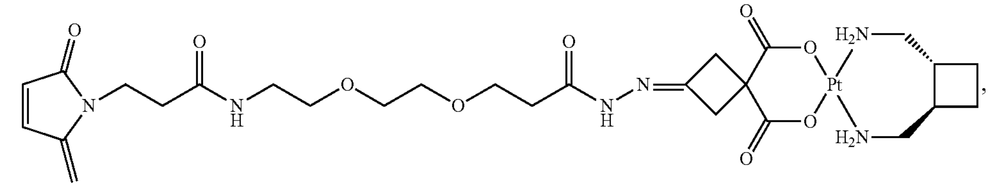
S51
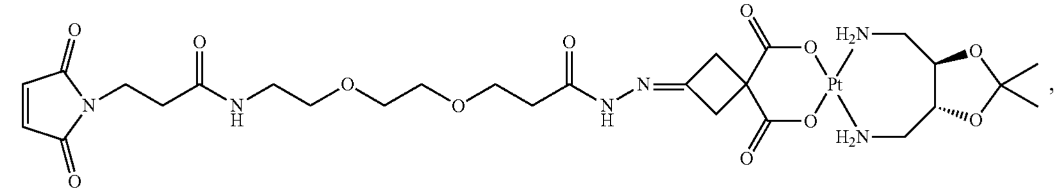
S52
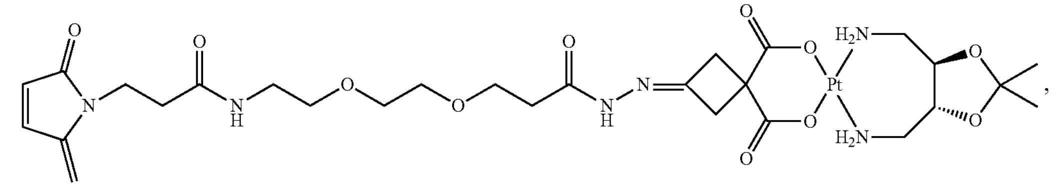
S53
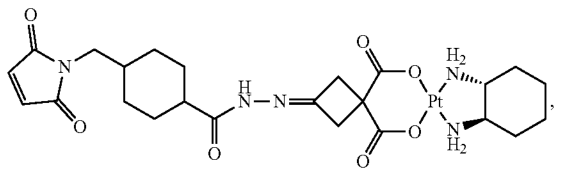
S54
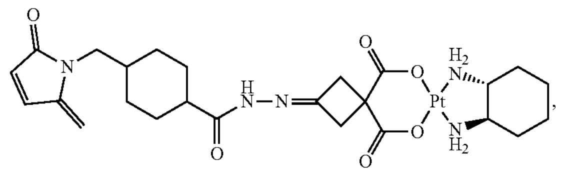
S55
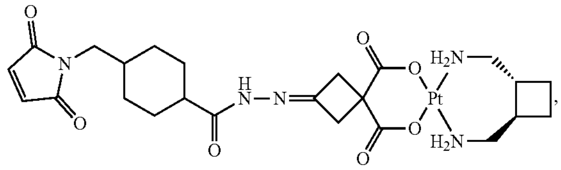
S56
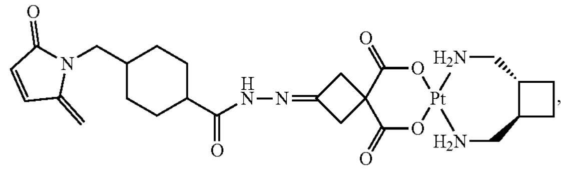
S57
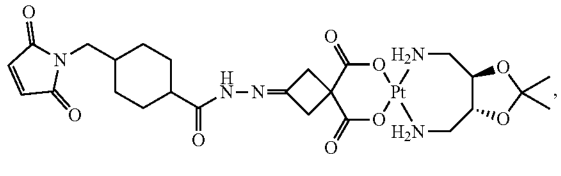
S58
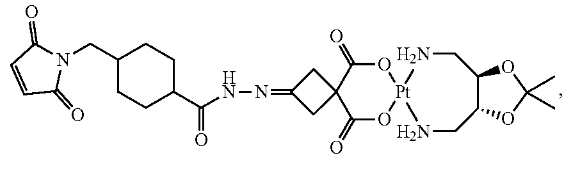

-continued
S59
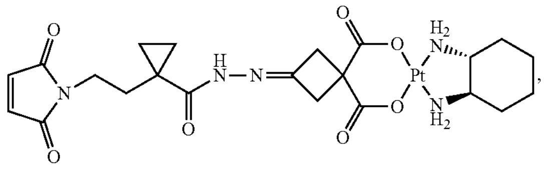
,
S60
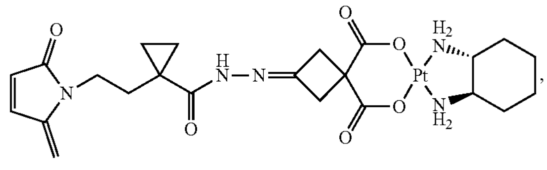
,
S61
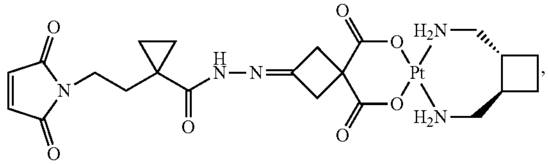
,
S62
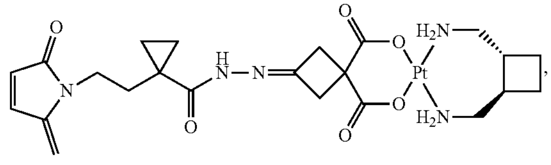
,
S63
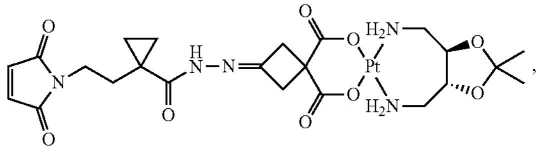
,
S64
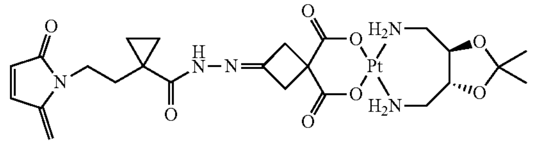
,
S65
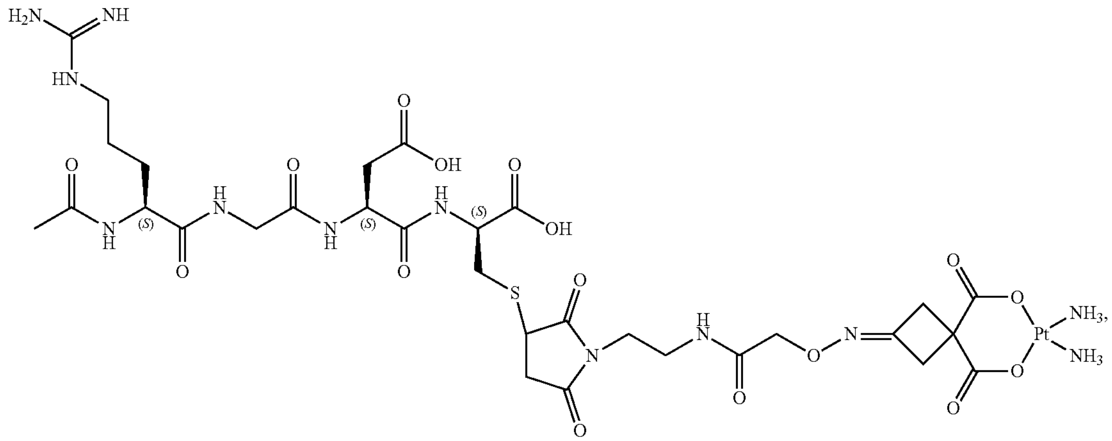
,
S66
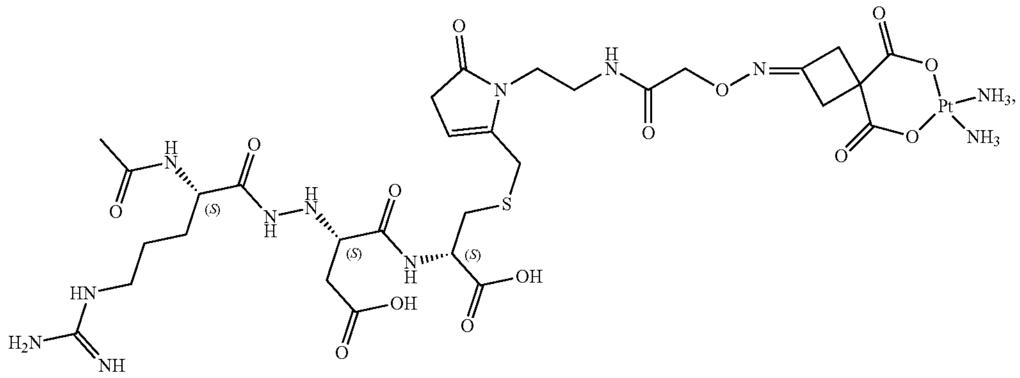
, -continued
S67
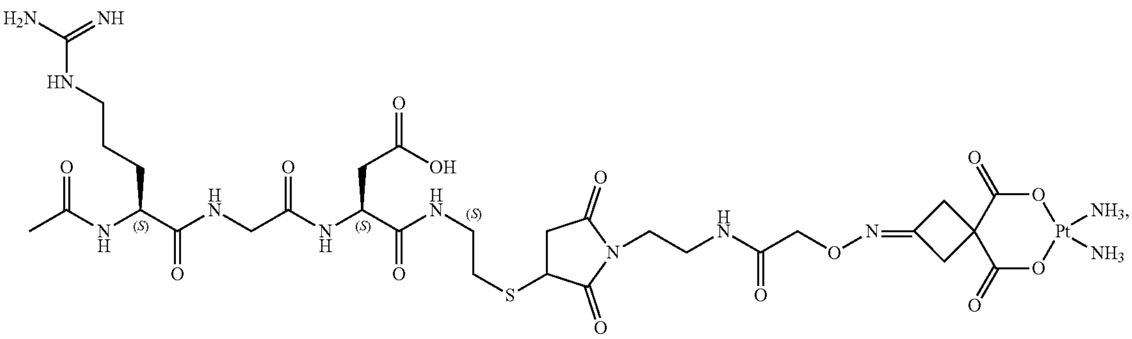
S68
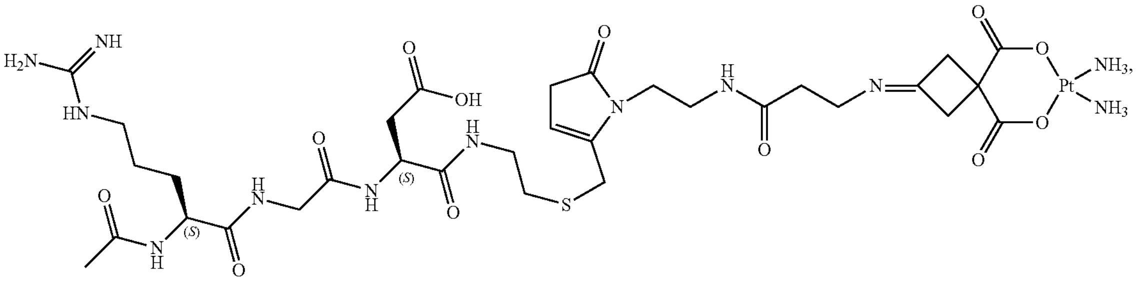
S69
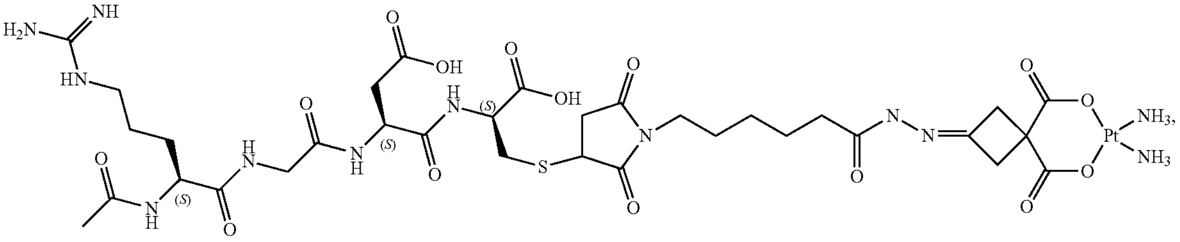
S70
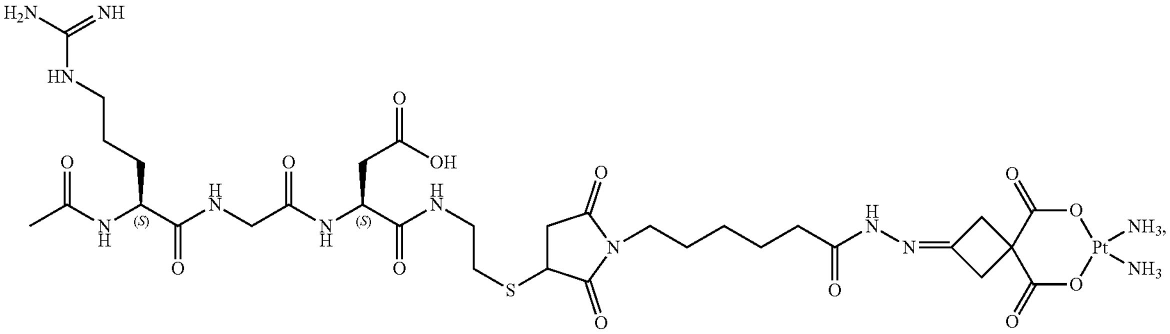

-continued
S71
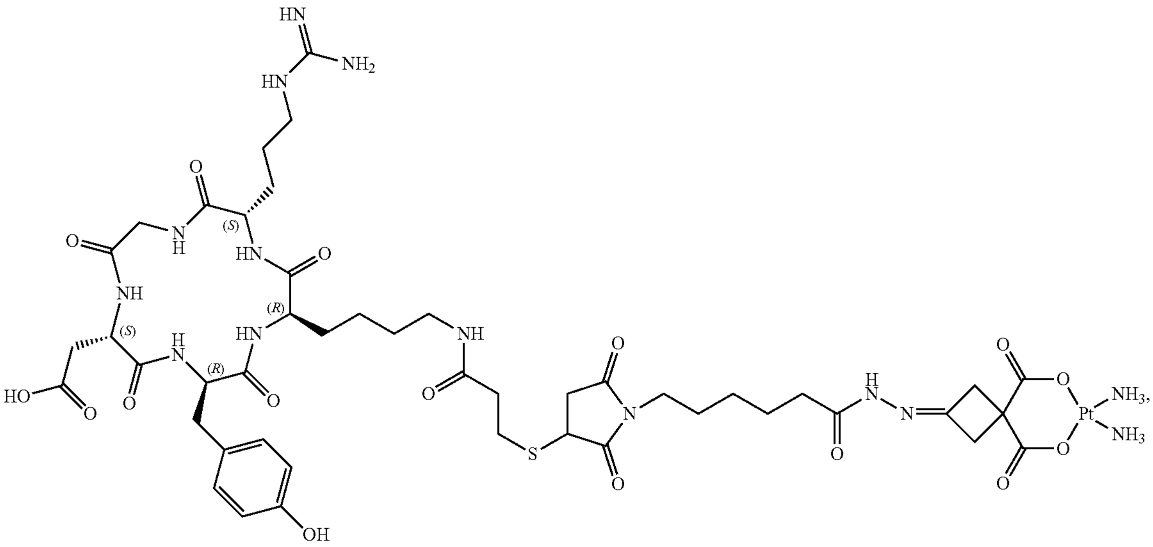
S72
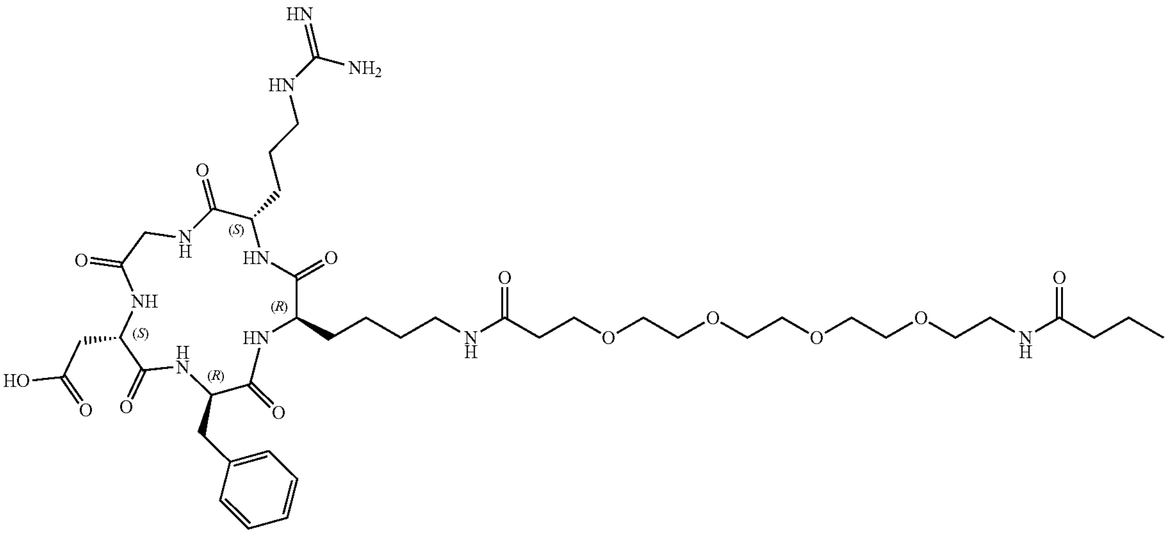

-continued
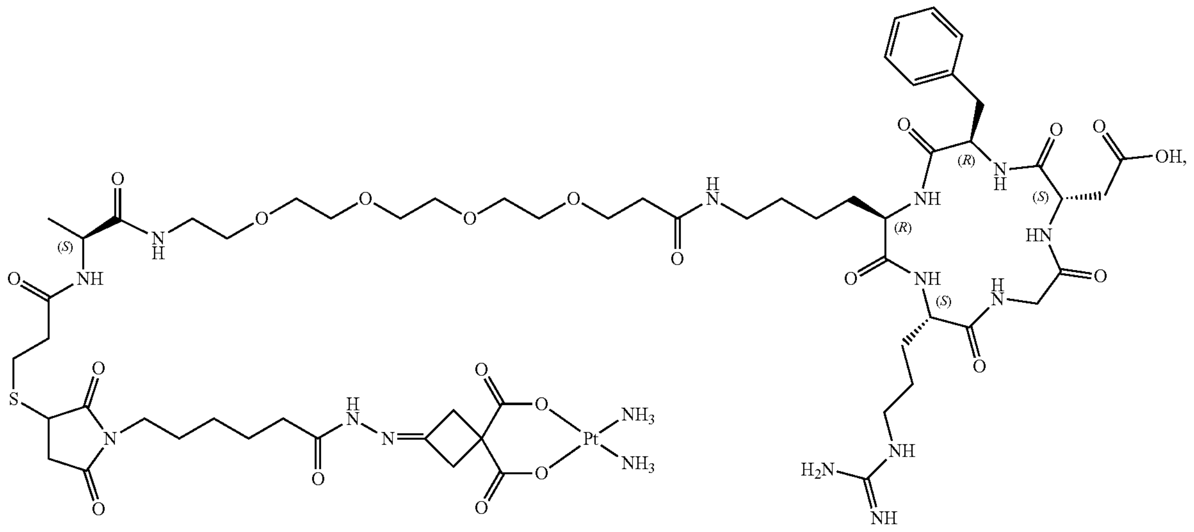
S73
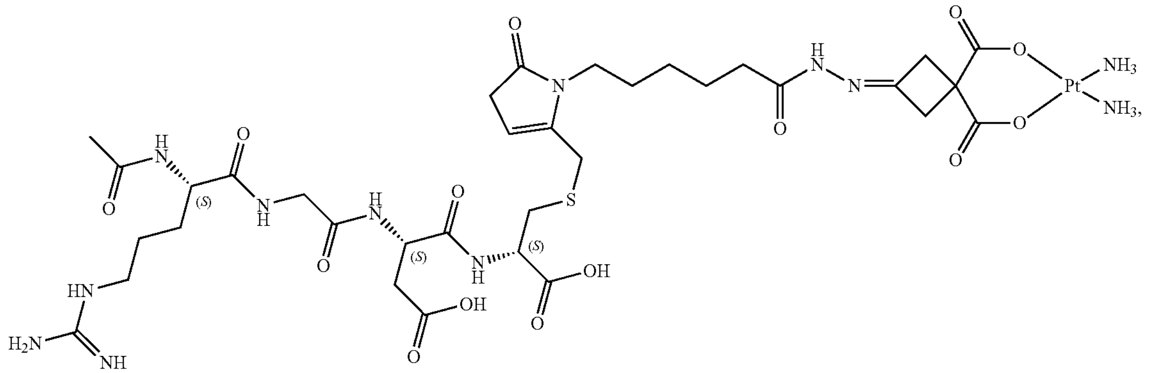
S74
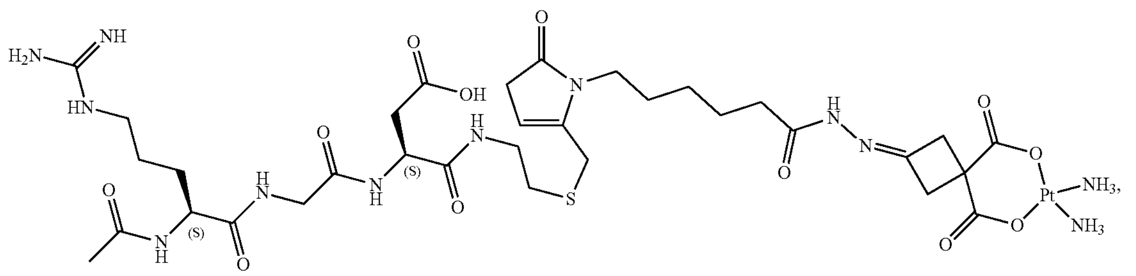

-continued
S75
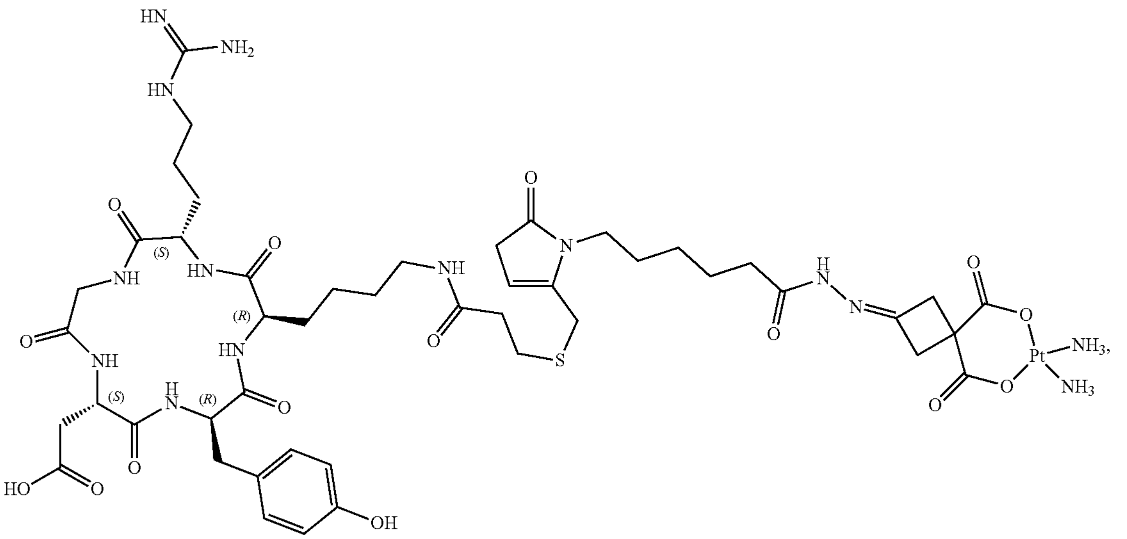
S76
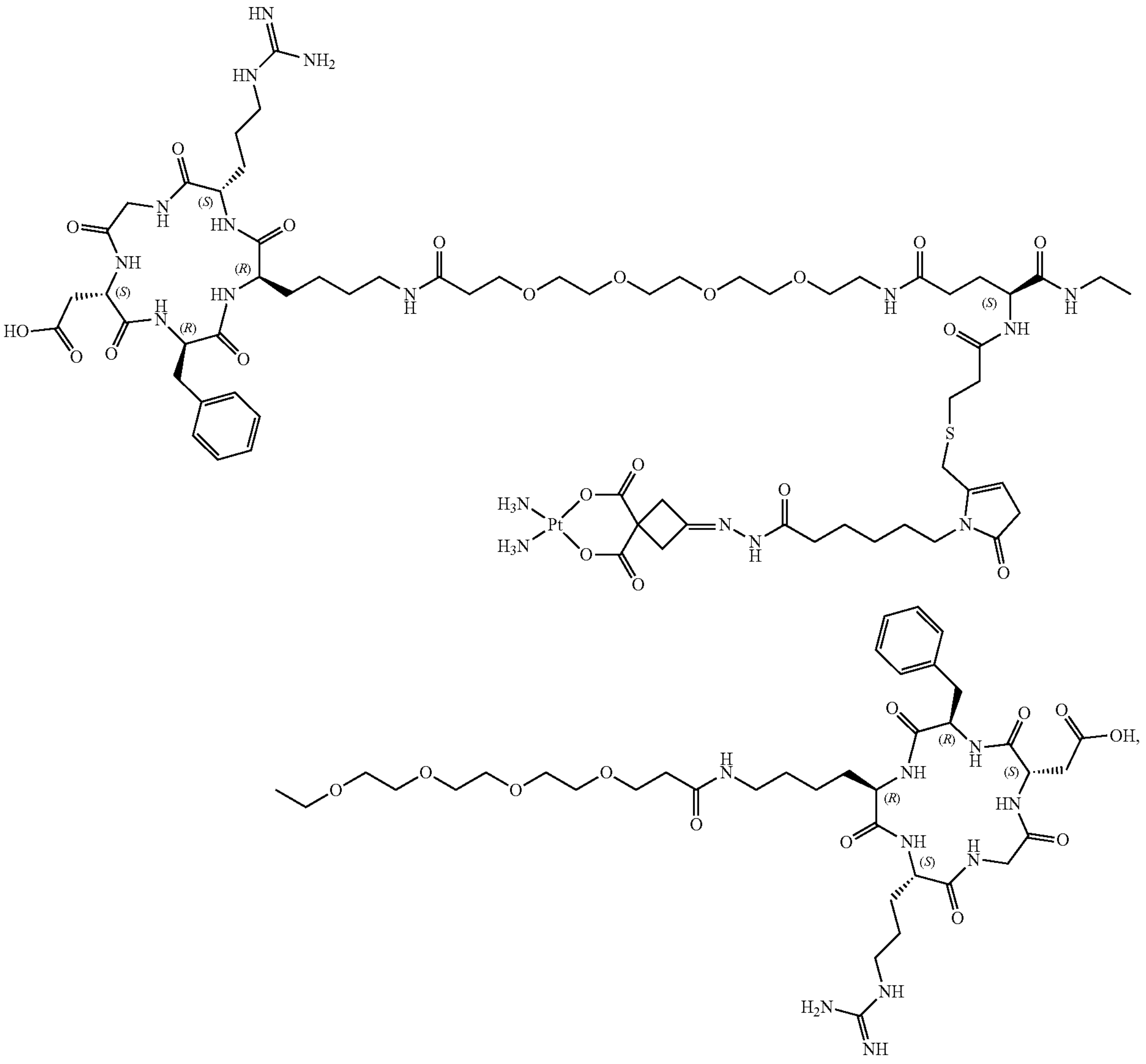

-continued
S77
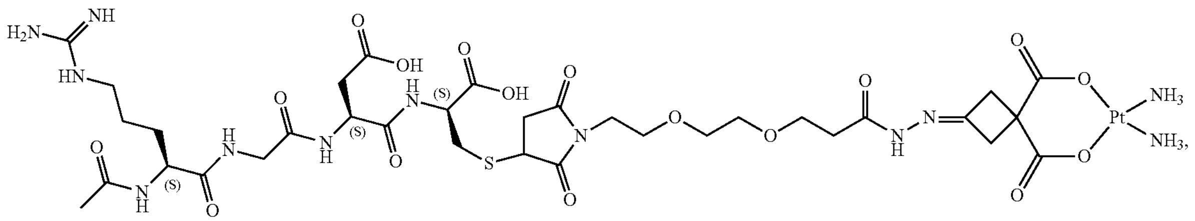
S78
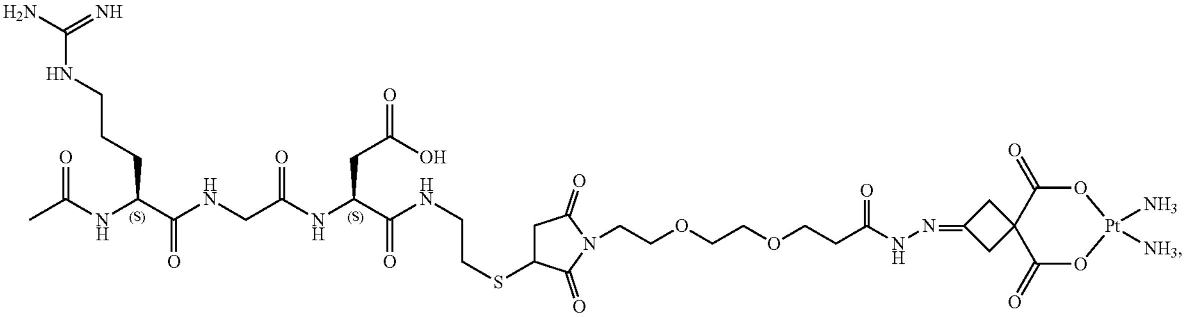
S79
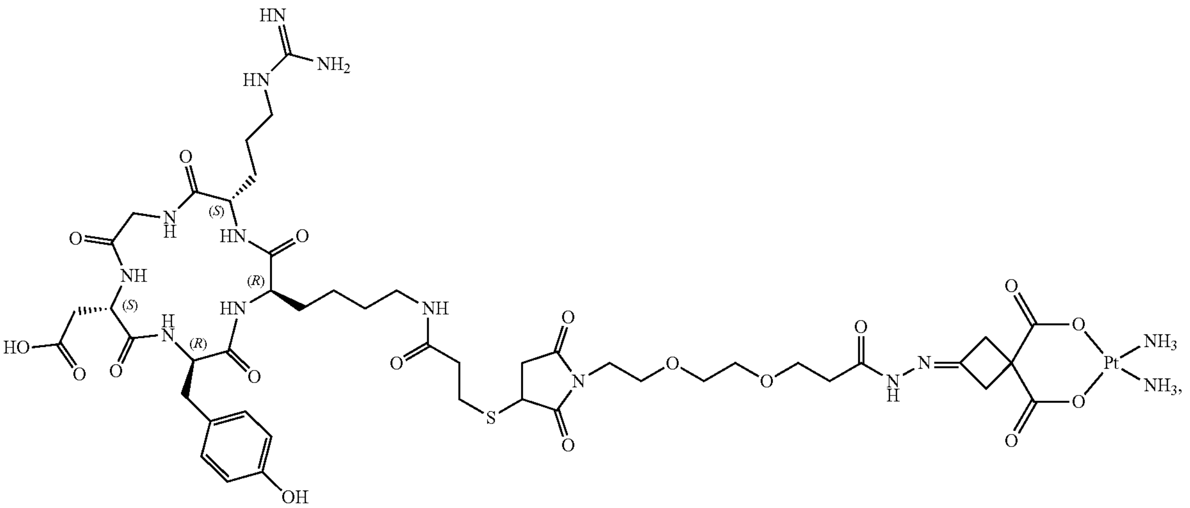
S80
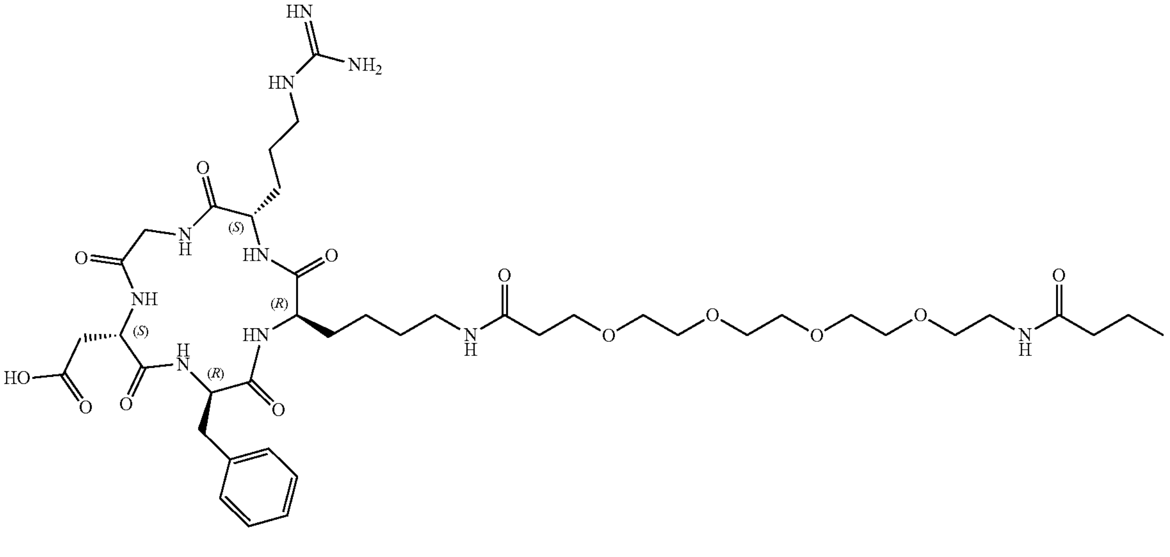

-continued
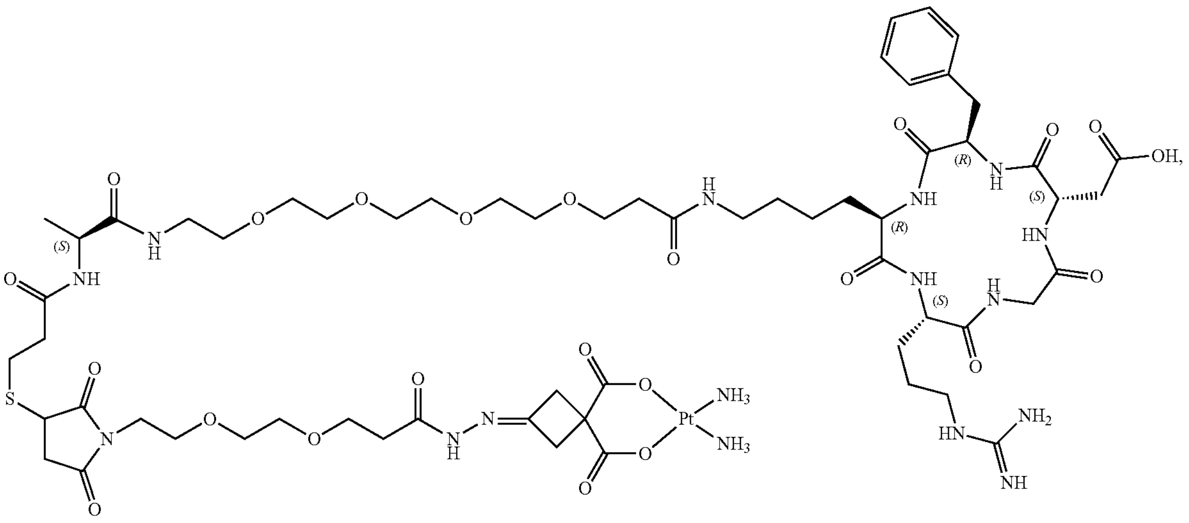
S81
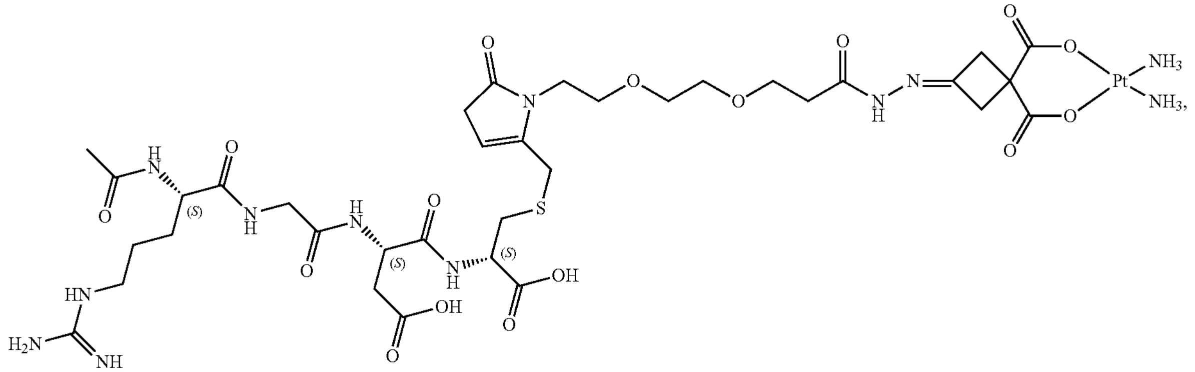
S82
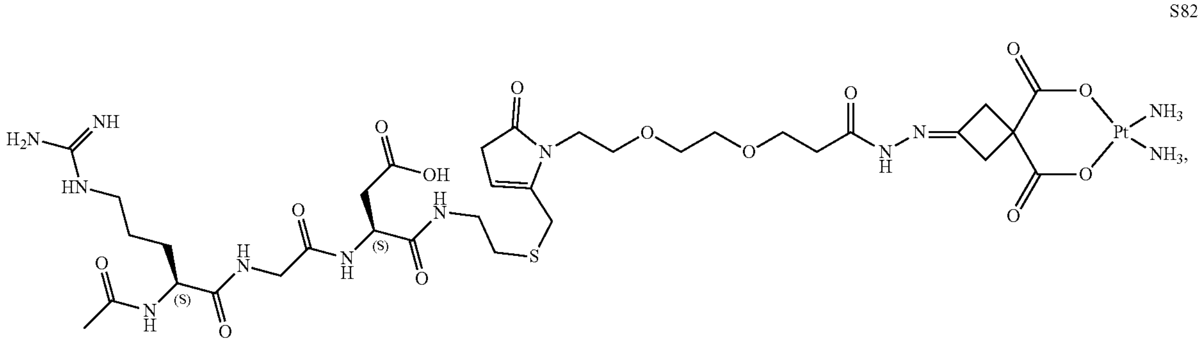

-continued
S83
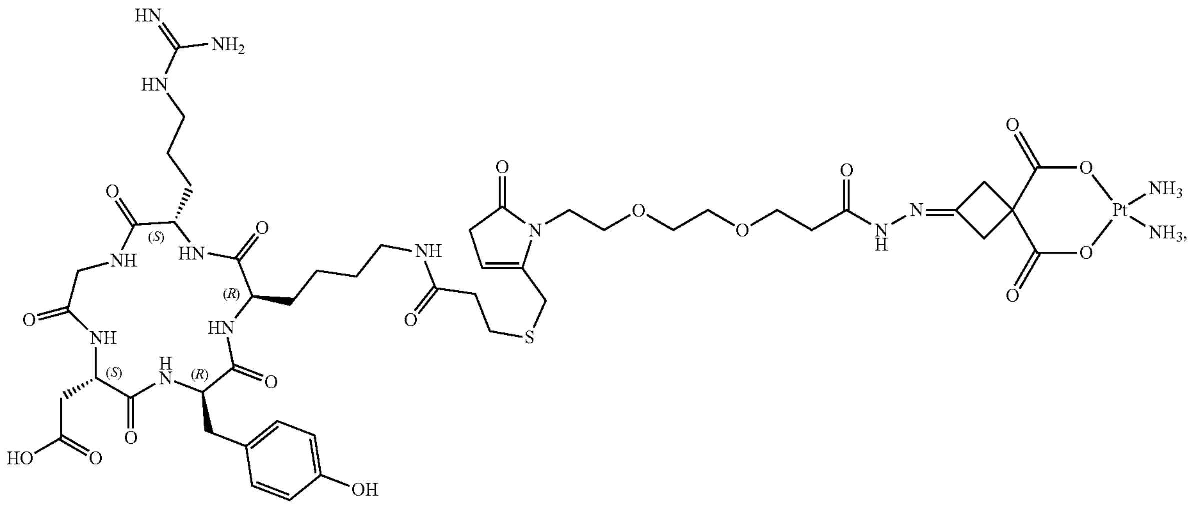
S84
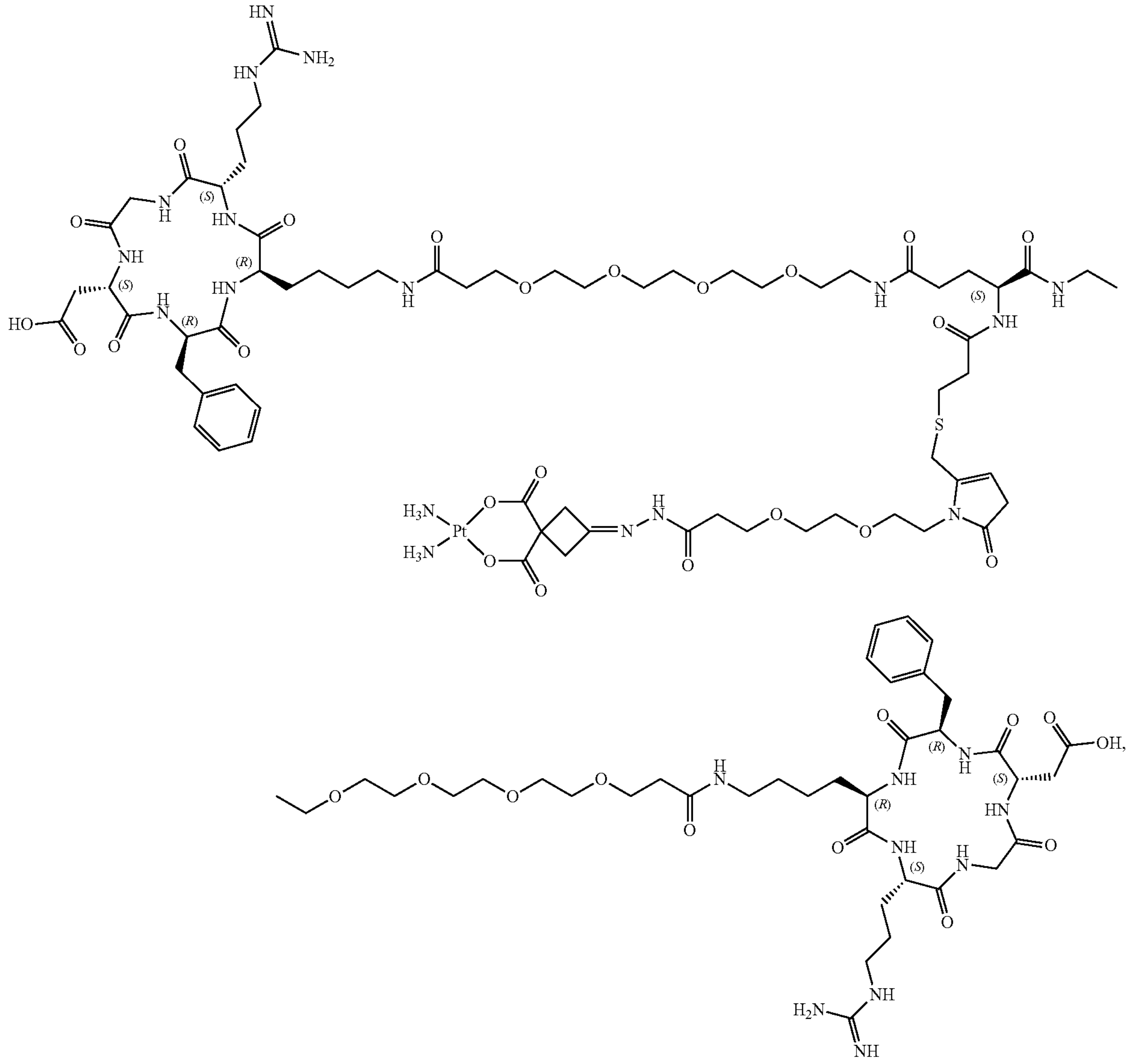

-continued
S85
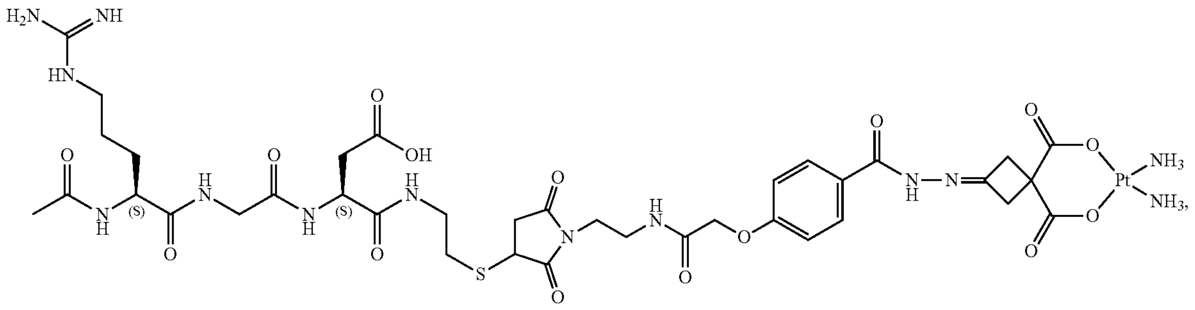
S86
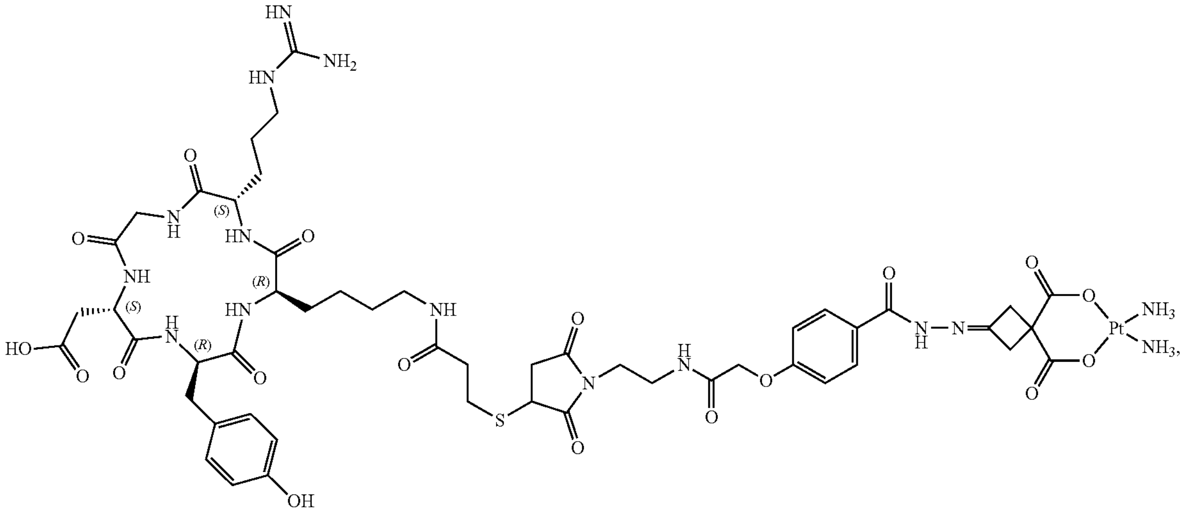
S87
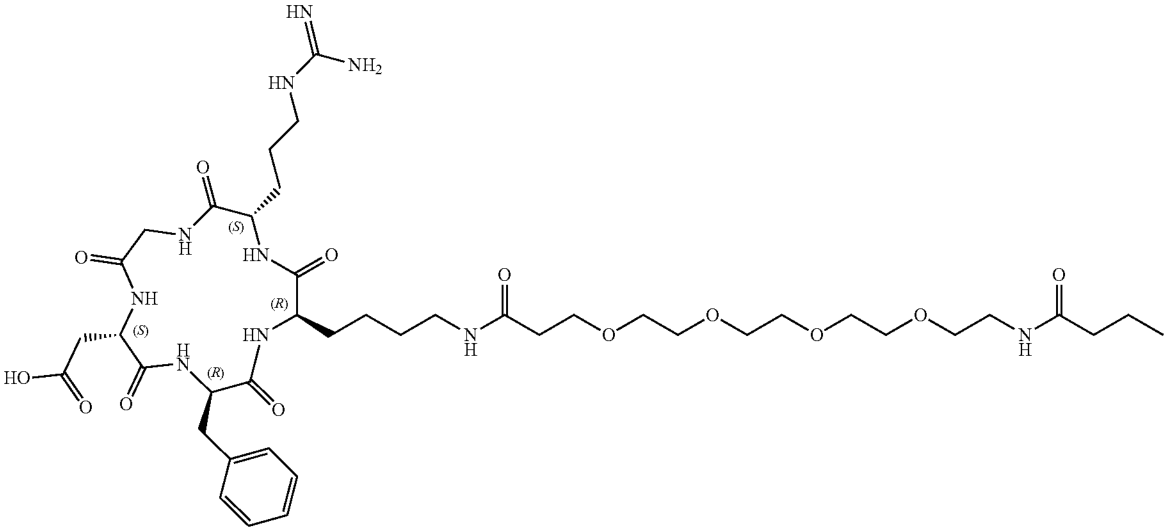

-continued
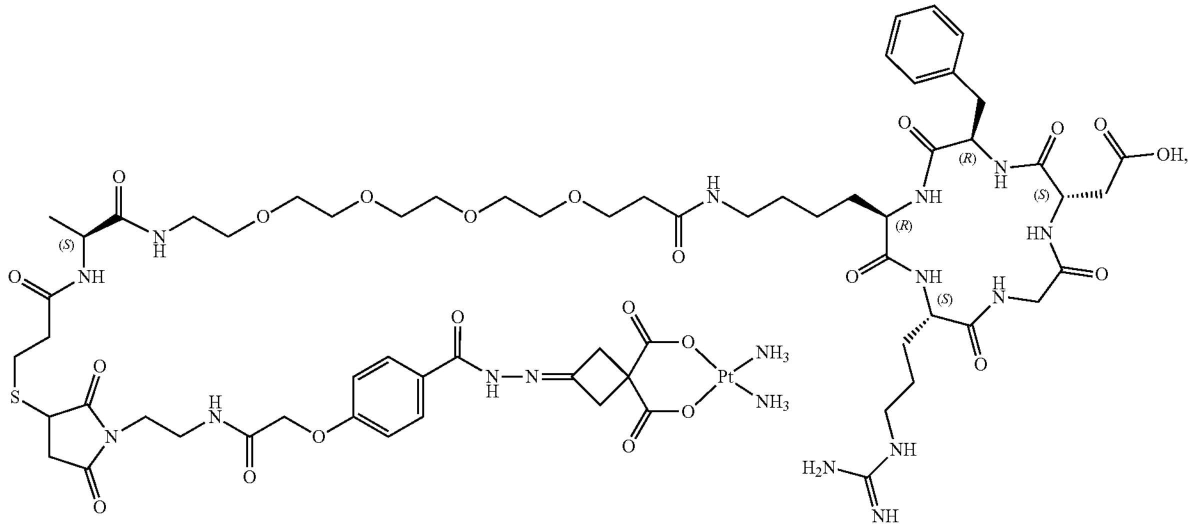
S88
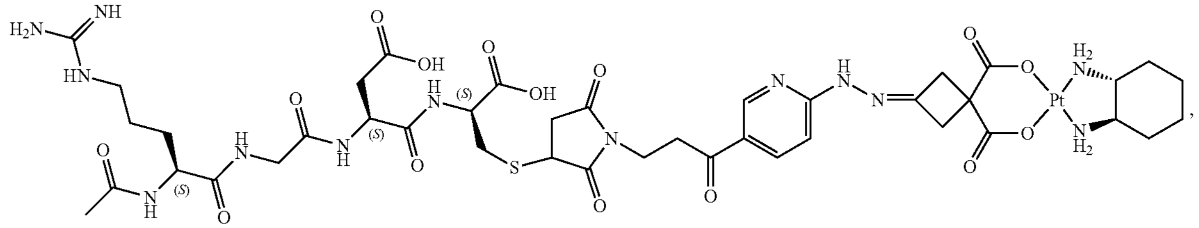
S89
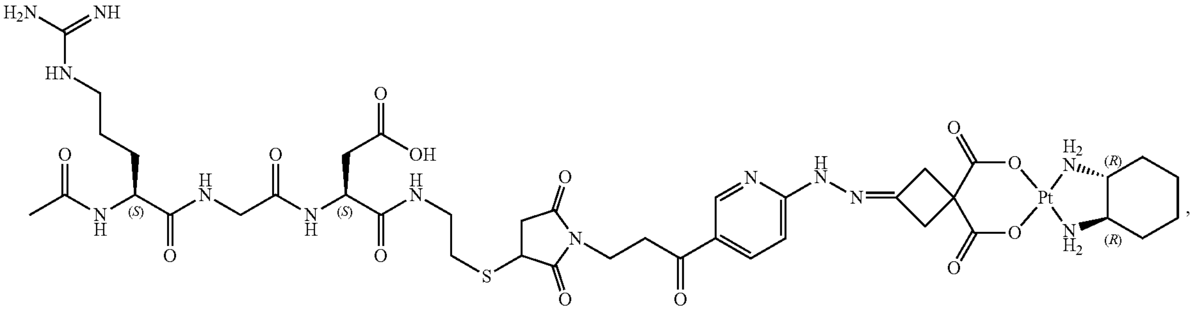
S90
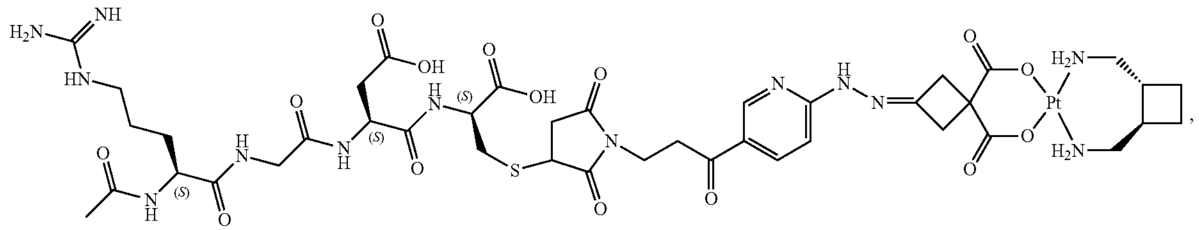

-continued
S91
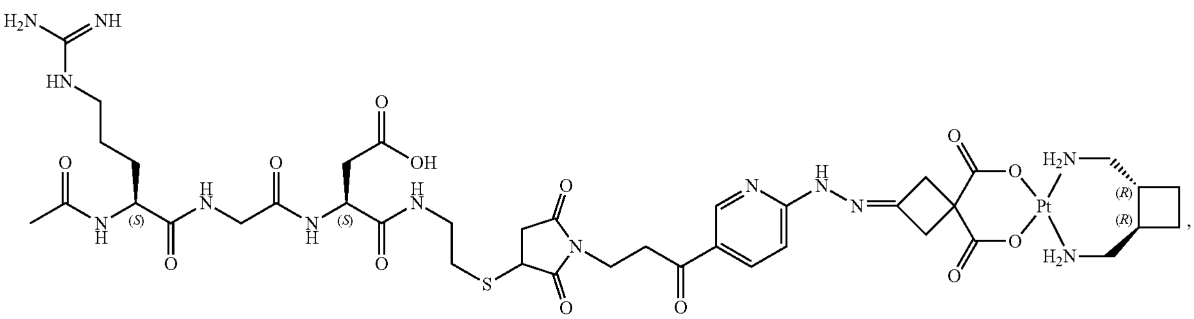
,
S92
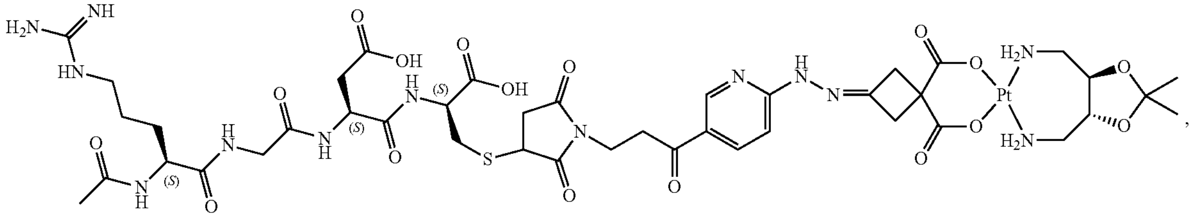
,
S93
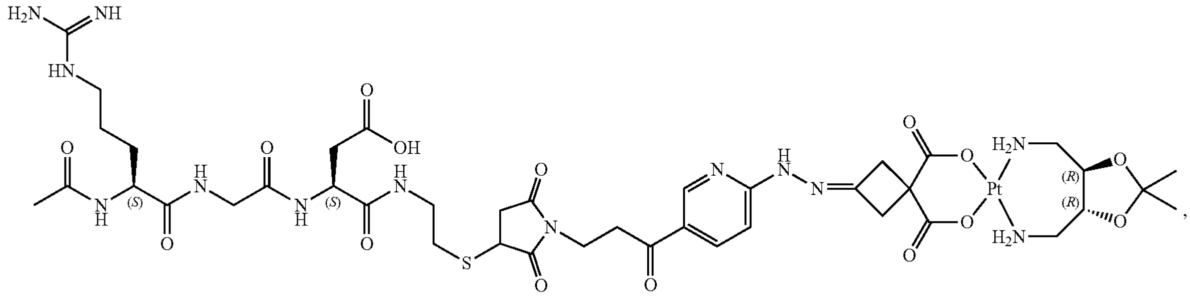
,
S94
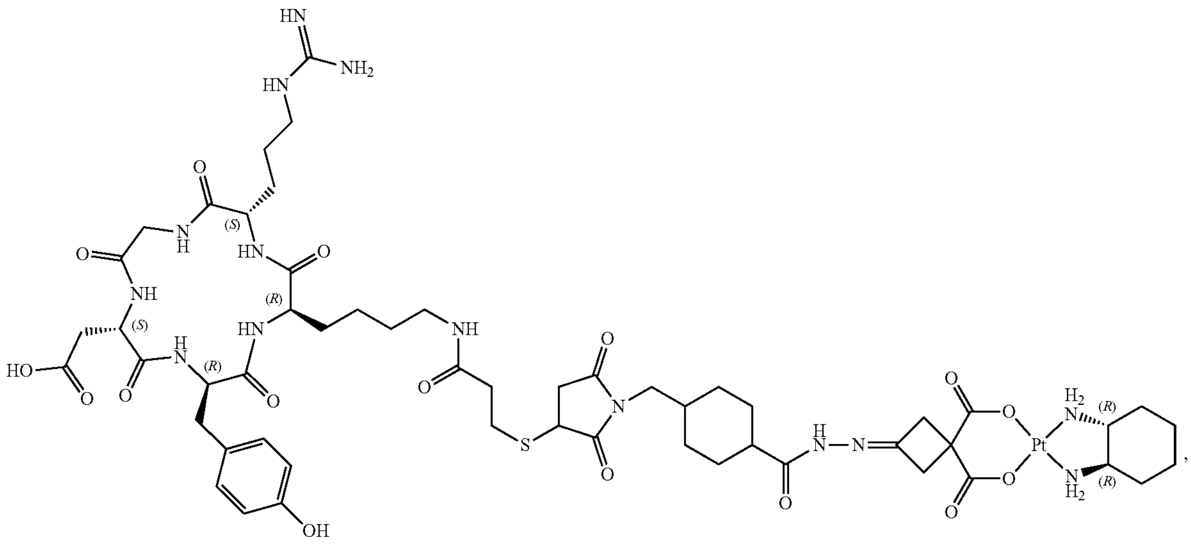
, -continued
S95
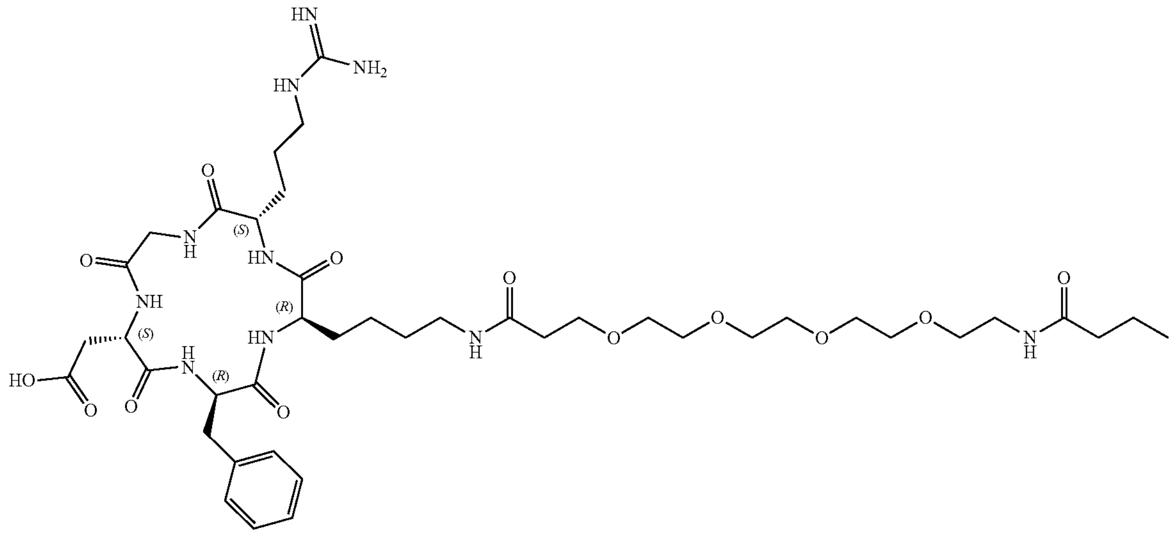
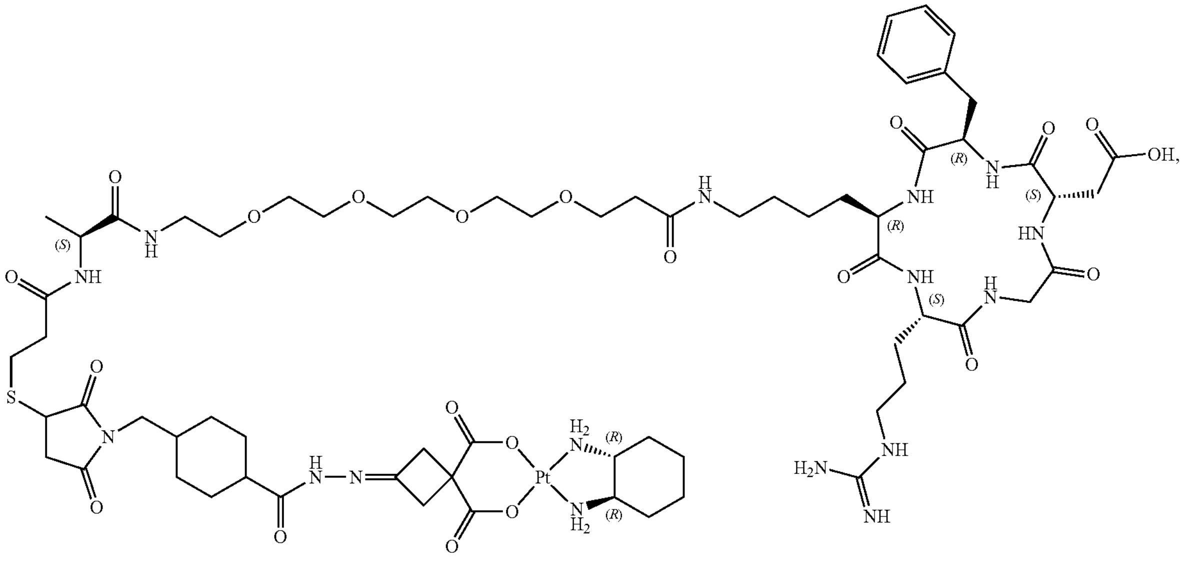
S96
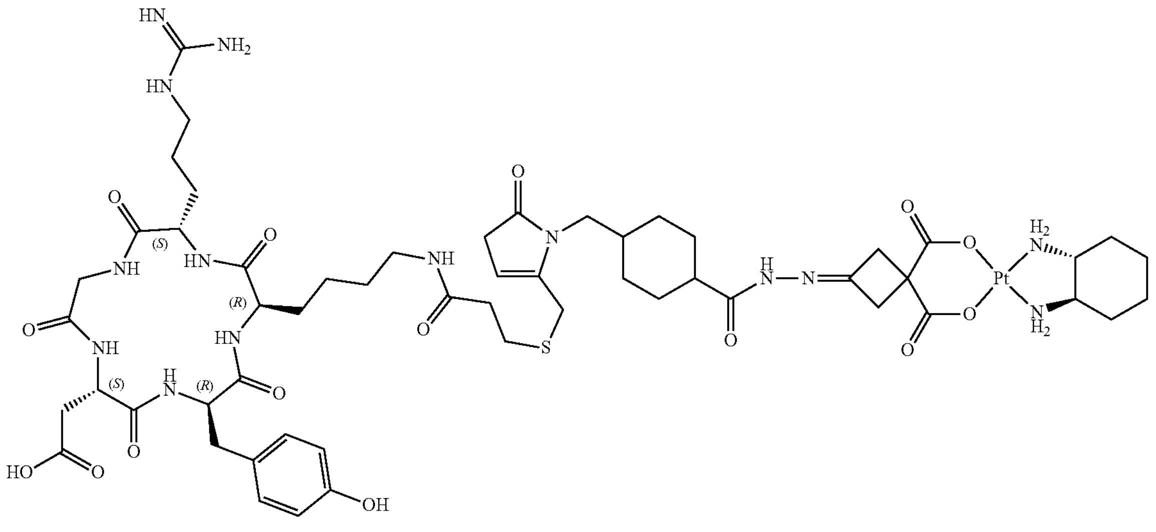
or -continued

S97

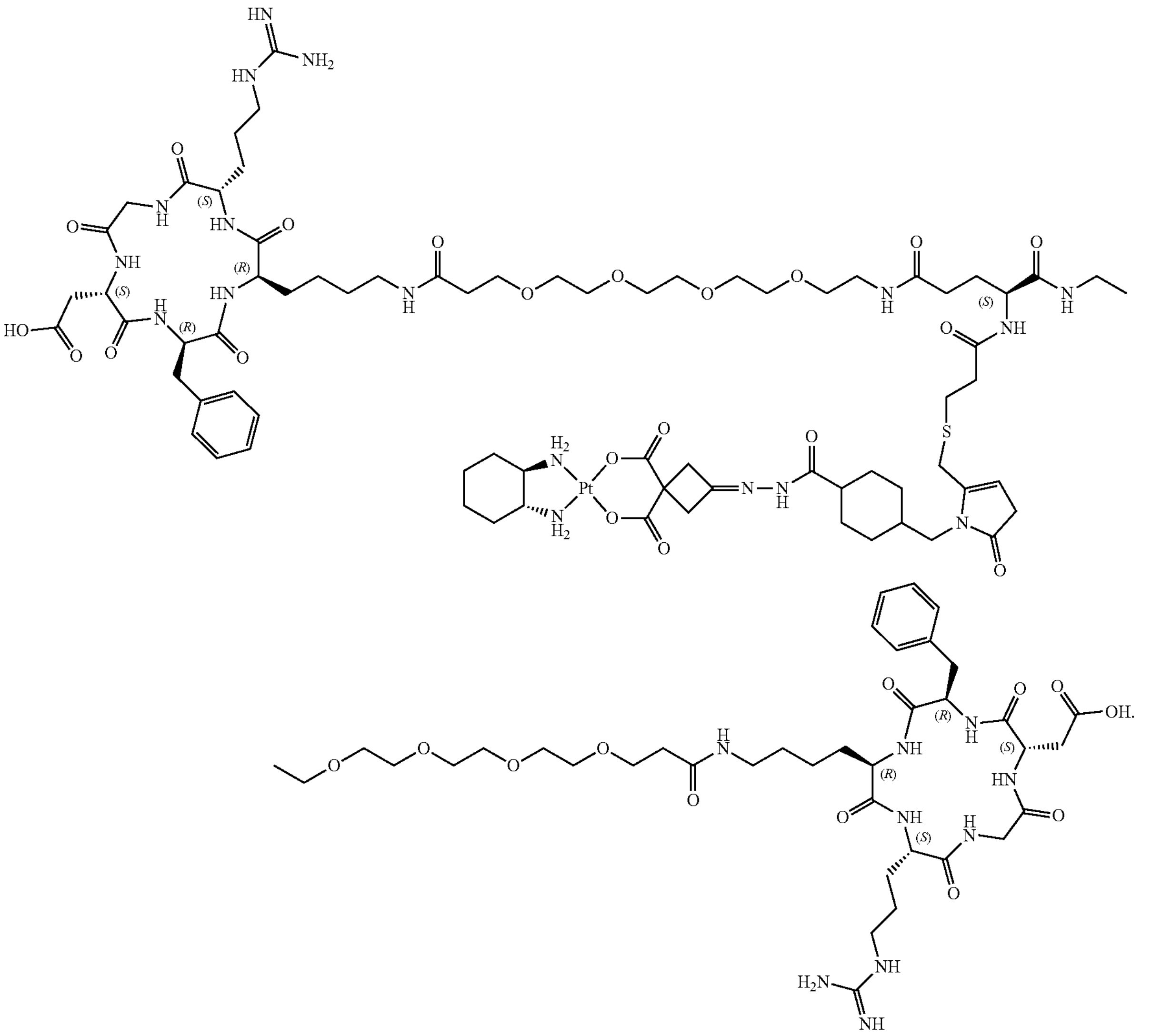

The present disclosure provides a pharmaceutical composition, comprising the compound represented by formula (I) or the pharmaceutically acceptable salt thereof and a pharmaceutically acceptable carrier.

The present disclosure provides a use of the compound represented by formula (I) or the pharmaceutically acceptable salt thereof, or the pharmaceutical composition in the manufacture of a medicament, and the medicament is preferably used for preventing and/or treating cancer, wherein, the cancer is preferably gastrointestinal cancer, colorectal cancer, colon cancer, liver cancer, hepatocellular carcinoma, pancreatic cancer, biliary tract cancer, gastric cancer, urogenital system cancer, bladder cancer, testicular cancer, cervical cancer, malignant mesothelioma, osteogenic sarcoma, esophageal cancer, laryngeal cancer, prostate cancer, hormone-resistant prostate cancer, lung cancer, small cell lung cancer, non-small cell lung cancer, breast cancer, triple negative breast cancer, breast cancer with BRCA1 and/or BRCA2 gene mutations, blood cancer, leukemia, acute primitive lymphoblastic leukemia, acute myeloid leukemia, chronic lymphocytic leukemia, chronic myeloid leukemia, lymphoma, Hodgkin's lymphoma, non-Hodgkin's lymphoma, follicular lymphoma, diffuse large B-cell lymphoma, ovarian cancer, brain cancer, neuroblastoma, Ewing sarcoma, renal cell carcinoma, epidermoid carcinoma, skin cancer, melanoma, head and/or neck cancer, head and neck squamous cell carcinoma, or oral cancer, more preferably colorectal cancer, colon cancer, pancreatic cancer, lung cancer, non-small cell lung cancer, ovarian cancer, cervical cancer, melanoma, head and/or neck cancer, or head and neck squamous cell carcinoma.

The present disclosure provides a use of the compound represented by formula (I) or the pharmaceutically acceptable salt thereof, or the pharmaceutical composition in the manufacture of a medicament for preventing and/or treating cancer, wherein, the compound represented by the formula (I) or the pharmaceutically acceptable salt thereof, or the pharmaceutical composition is administered in combination with an anticancer medicament and/or in combination with radiotherapy and/or immunotherapy.

The present disclosure provides a method for preventing and/or treating cancer, comprising administering a therapeutically effective amount of the compound represented by formula (I) or the pharmaceutically acceptable salt thereof, or the pharmaceutical composition to a patient;

wherein, the cancer is preferably gastrointestinal cancer, colorectal cancer, colon cancer, liver cancer, hepatocellular carcinoma, pancreatic cancer, biliary tract cancer, gastric cancer, urogenital system cancer, bladder cancer, testicular cancer, cervical cancer, malignant mesothelioma, osteogenic sarcoma, esophageal cancer, laryngeal cancer, prostate cancer, hormone-resistant prostate cancer, lung cancer, small cell lung cancer, non-small cell lung cancer, breast cancer, triple negative breast cancer, breast cancer with BRCA1 and/or BRCA2 gene mutations, blood cancer, leukemia, acute primitive lymphoblastic leukemia, acute myeloid leukemia, chronic lymphocytic leukemia, chronic myeloid leukemia, lymphoma, Hodgkin's lymphoma, non-Hodgkin's lymphoma, follicular lymphoma, diffuse large B-cell lymphoma, ovarian cancer, brain cancer, neuroblastoma, Ewing sarcoma, renal cell carcinoma, epidermoid carcinoma, skin cancer, melanoma, head and/or neck cancer, head and neck squamous cell carcinoma, or oral cancer, more preferably colorectal cancer, colon cancer, pancreatic cancer, lung cancer, non-small cell lung cancer, ovarian cancer, cervical cancer, melanoma, head and/or neck cancer, or head and neck squamous cell carcinoma.

Beneficial Results

The present disclosure discloses a series of platinum derivatives with novel structures represented by formula I, and tests their in vitro water solubility and in vivo tumor inhibition activity, which led to a completely unforeseen discovery:

1) The in vitro water solubility experiments show that the water solubility of the examples S47, S72, S80, S95 and S97 disclosed in the present disclosure are significantly improved compared with the marketed drugs. Especially the water solubility of example 72 and example S80, compared with the marketed drug carboplatin, has nearly a 1-fold improvement; the water solubility of example S47, example S95 and example S97, compared with the marketed drug oxaliplatin, has an improvement of 3 times or more, and examples S47, S72, S80, S95 and S97S can be made into a lyophilized powder or an aqueous solution dosage form, which solves the adverse effects of poor water solubility of platinum drugs in clinical application.

2) The in vivo tumor inhibition experiment in mice shows that the examples S47, S70, etc. of the present disclosure have more obvious ability to inhibit the growth of transplanted tumor S180 than the clinical drug carboplatin, and have a good dose-effect relationship, and have a broad antitumor application prospect.

DETAILED DESCRIPTION OF THE PREFERRED EMBODIMENTS

Embodiments of the present disclosure will be described in detail below in combination with examples, but those skilled in the art will understand that the following examples are only for illustrating the present disclosure, and should not be regarded as limiting the scope of the present disclosure. If no specific conditions are specified in the example, the experimental methods usually follow the conventional conditions or the conditions recommended by the manufacturer. If the manufacturer is not indicated in the reagents or instruments used, they are all conventional products that can be obtained from the market.

The structures of the compounds were determined by liquid chromatography-mass spectrometry (HPLC-MS). The mass spectrum was determined by watersZQ2000 mass spectrometer, manufacturer: Waters, model: ZQ2000.

When liquid chromatography-mass spectrometry was used for determination, the model of liquid chromatography instrument was Water 2695HPLC Waters 2998, detector: ultraviolet detector, chromatographic column: YMC pack ODS-AQ 100*4.6 mm*5 μm. The detection conditions of the liquid chromatograph were as follows:

chromatographic column temperature: 35° C.; flow rate: 1 mL/min; detection wavelength: 214 nm; gradient elution: (0 min: 90% (v/v) A, 10% (v/v) B; 10 min: 10% (v/v)A, 90% (v/v)B; 15 min: 10% (v/v)A, 90% (v/v)B; 15.1 min: 90% (v/v)A, 10% (v/v)B; 20 min: 90% (v/v)A, 10% (v/v)B); mobile phase A: 0.1% formic acid; mobile phase B: acetonitrile.

When the liquid phase instrument was used for purification, the instrument used was Dalian Elite preparative liquid chromatograph, model: P270, detector: ultraviolet detector, chromatographic column: C18 reversed-phase silica gel 20*250 mm. The preparation method of the preparative high performance liquid chromatograph was as follows:

chromatographic column temperature: 25° C.; detection wavelength: 214 nm; elution gradient: (0 min: 85% (v/v)A, 15% (v/v)B, flow rate: 25 mL/min; 8 min: 20% (v/v)A, 80% (v/v)B, flow rate: 25 mL/min; 8.01 min: 5% (v/v)A, 95% (v/v)B, flow rate: 40 mL/min; 10 min: 5% (v/v)A, 95% (v/v)B, flow rate: 40 mL/min; 10.01 min: 50% (v/v)A, 50% (v/v)B, flow rate: 40 mL/min; 12 min: 50% (v/v)A, 50% (v/v)B, flow rate: 40 mL/min); mobile phase A: 0.01% formic acid/$H_2O$; mobile phase B: acetonitrile.

Thin layer chromatography (TLC) was used for reaction detection. The development system used was dichloromethane:methanol=10:1 (volume ratio).

The digital display magnetic stirrer was used as the stirrer. Manufacturer: Dragon Laboratory Instruments, model: MS-H280-Pro.

The general synthesis method of the examples was as follows:

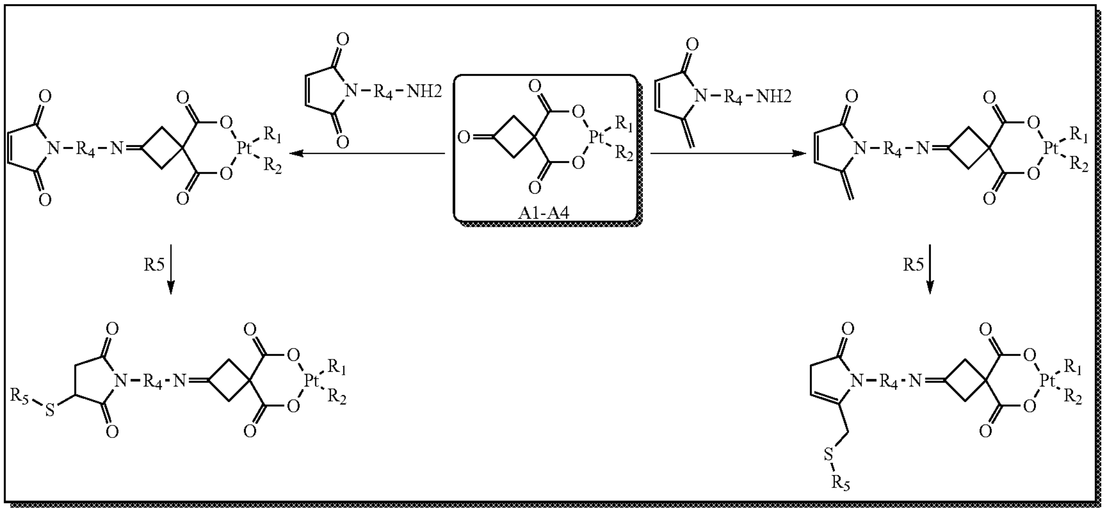
A1-A4 and
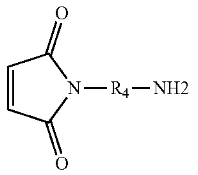
were subjected to a coupling reaction to produce
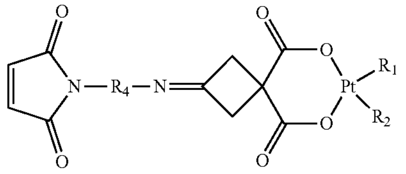
(i.e., examples 1, 3, 5, 7, 9, 11, 13, 15, 17, 19, 21, 22, 23, 24, 25, 27, 29, 30, 31, 33, 35, 37, 39, 41, 43, 45, 47, 49, 51, 53, 55, 57, 59, 61, 63);
A1-A4 and
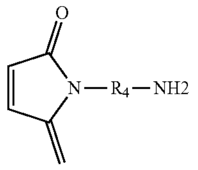
were subjected to a coupling reaction to produce
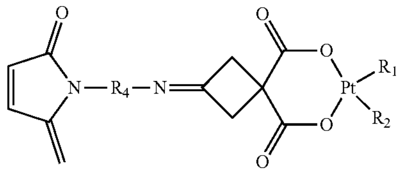
(i.e., examples 2, 4, 6, 8, 10, 12, 14, 16, 18, 20, 26, 28, 32, 34, 36, 38, 40, 42, 44, 46, 48, 50, 52, 54, 56, 58, 60, 62, 64);
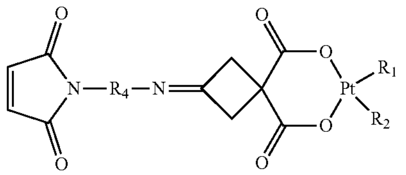
and $R_5$ were subjected to an addition reaction to produce
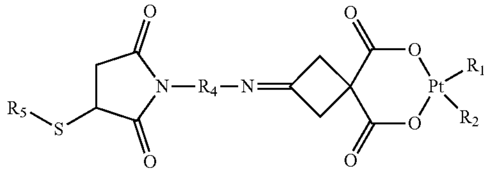
(i.e., examples 65, 67, 69, 70, 71, 72, 77, 78, 79, 80, 85, 86, 87, 88, 89, 90, 91, 92, 93, 94, 95);
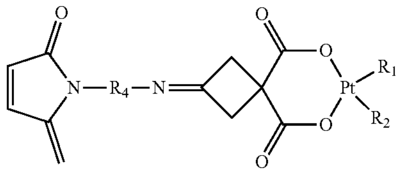

and $R_5$ were subjected to an addition reaction to produce

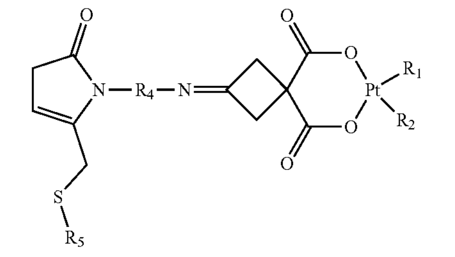

(i.e., examples 66, 68, 73, 74, 75, 76, 81, 82, 83, 84, 96, 97).

Taking example S1 and example 65 as examples, the specific implementation process was as follows:

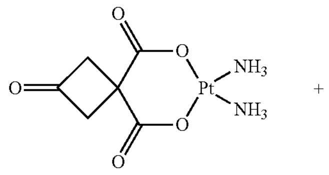

A1

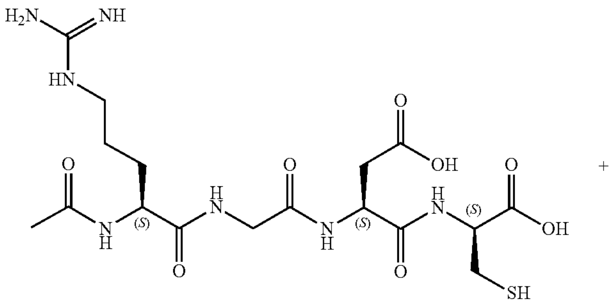

R5-1

-continued

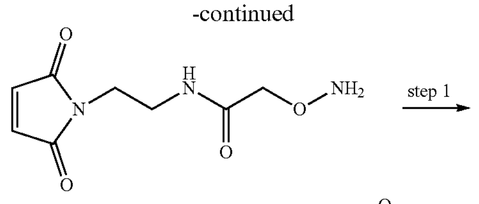

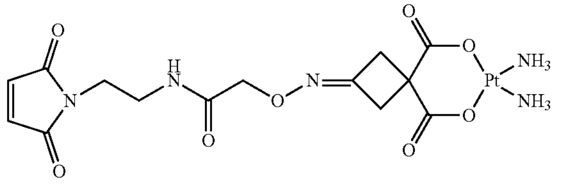

S1

1) In a 50 mL single-necked flask, A1 (177.2 mg, 0.46 mmol), 2-(aminooxy)-N-(2-(2,5-dioxo-2,5-dihydro-1H-pyrrol-1-yl)ethyl)acetamide (98 mg 0.46 mmol) were weighed in turn, and after dissolving by adding 15 mL of N,N-dimethylformamide, 4 A molecular sieve (162 mg) was added, and the reaction system was replaced with nitrogen. The reaction solution was reacted overnight at room temperature. The reaction solution was evaporated to dryness by rotary evaporation under reduced pressure, and the crude product was purified by silica gel column chromatography to obtain a white solid (169.0 mg, yield of 63.3%), i.e., example S1.

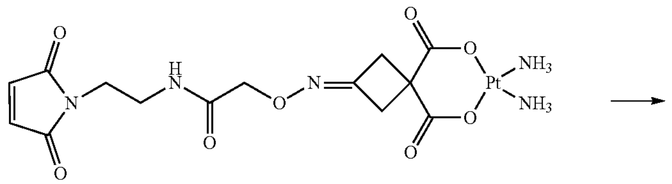

S1

-continued

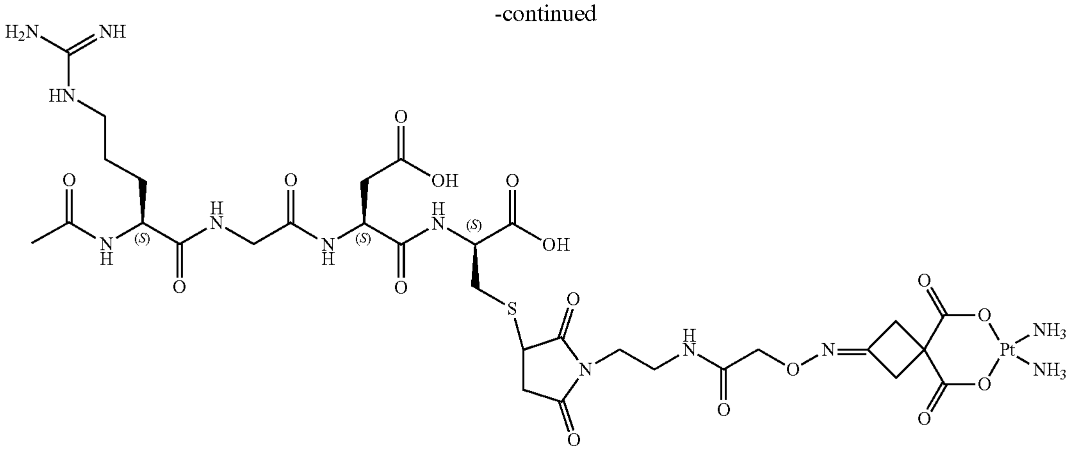

S65

2) In a 50 mL single-necked flask, example S1 (151 mg, 0.26 mmol) and R5-1 (117.5 mg, 0.26 mmol) were weighed in turn, then 15 mL of methanol was added, and the reaction system was replaced with nitrogen, and the reaction solution was reacted overnight at room temperature. The reaction solution was evaporated to dryness by rotary evaporation under reduced pressure, and refined and separated by semi-preparative HPLC, and freeze-dried by a freeze dryer to obtain a white solid (181.2 mg, yield of 65%), i.e., example S65.

A. When $R_4$ and $R_5$ were respectively different substituents, the compounds shown in Table 1 below could be obtained, i.e., examples S1-S97.

TABLE 1
| Structures of Examples | | |
|---|---|---|
| | Substituent | Example |
| $R_3$: | 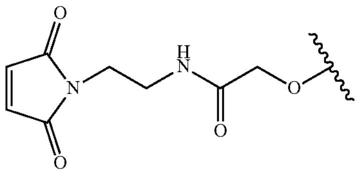 [SMILES: *OCC(=O)NCCN1C(=O)C=CC1=O] | 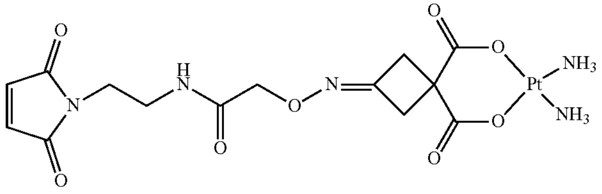 S1 |
| $R_1$, $R_2$: | 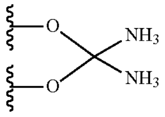 (A1) | |
| $R_3$: | 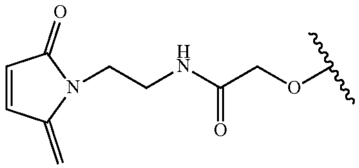 [SMILES: *OCC(=O)NCCN1C(=C)C=CC1=O] | 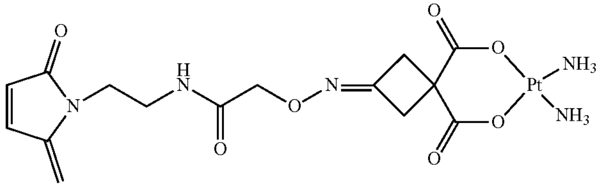 S2 |
| $R_1$, $R_2$: | 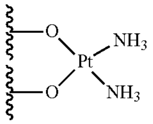 (A1) | |

TABLE 1-continued
Structures of Examples
| | Substituent | Example |
|---|---|---|
| $R_3$: | 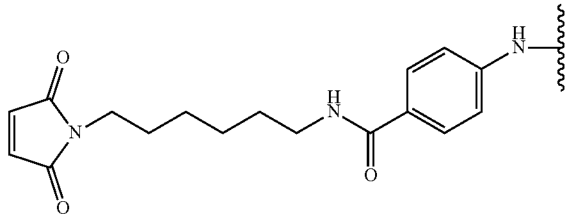 [SMILES: *Nc1ccc(C(=O)NCCCCCCN2C(=O)C=CC2=O)cc1] | 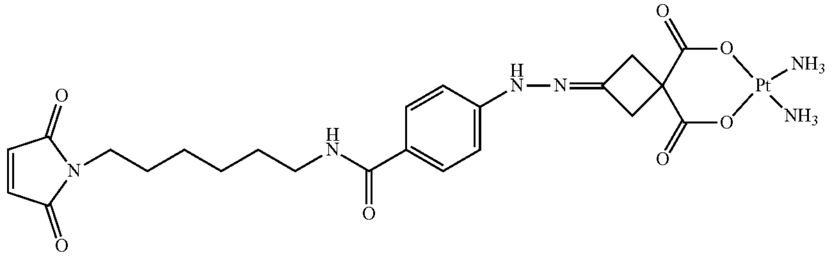<br>S3 |
| $R_1$, $R_2$: | 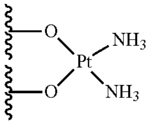<br>(A1) | |
| $R_3$: | 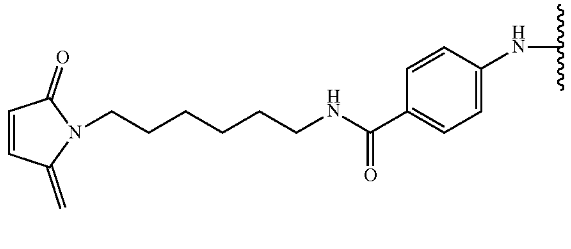 [SMILES: *Nc1ccc(C(=O)NCCCCCCN2C(=C)C=CC2=O)cc1] | 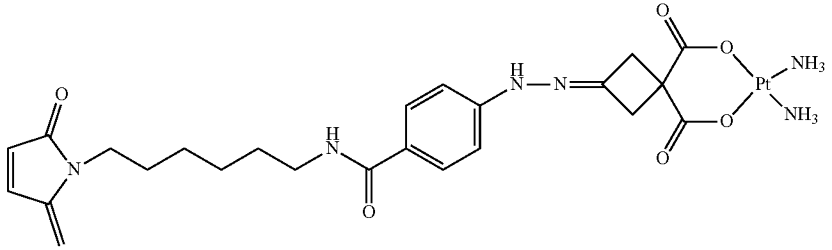<br>S4 |
| $R_1$, $R_2$: | 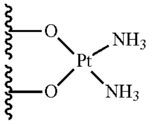<br>(A1) | |

TABLE 1-continued
| Structures of Examples | | |
|---|---|---|
| | Substituent | Example |
| $R_3$: | 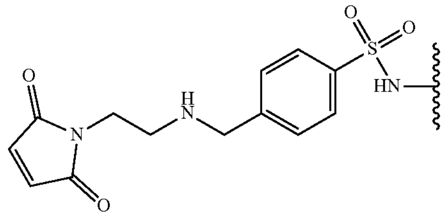 [SMILES: *NS(=O)(=O)c1ccc(CNCCN2C(=O)C=CC2=O)cc1] | 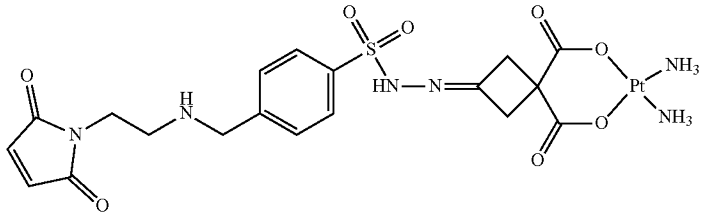<br>S5 |
| $R_1$, $R_2$: | 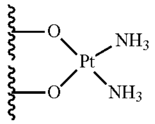<br>(A1) | |
| $R_3$: | 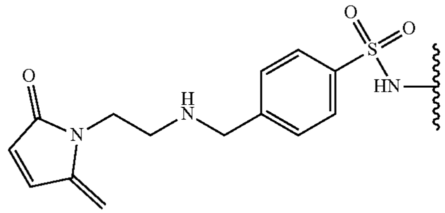 [SMILES: *NS(=O)(=O)c1ccc(CNCCN2C(=C)C=CC2=O)cc1] | 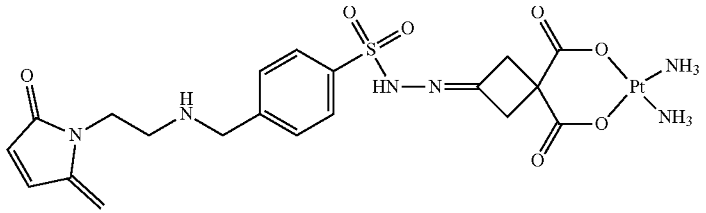<br>S6 |
| $R_1$, $R_2$: | 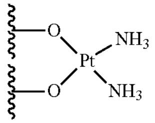<br>(A1) | |

TABLE 1-continued
| Structures of Examples | | |
|---|---|---|
| | Substituent | Example |
| $R_3$: | 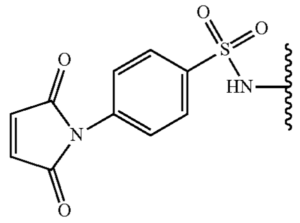 [SMILES: *NS(=O)(=O)c1ccc(N2C(=O)C=CC2=O)cc1] | 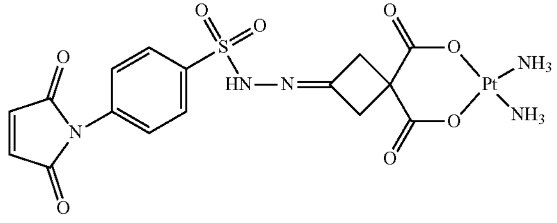 S7 |
| $R_1$, $R_2$: | 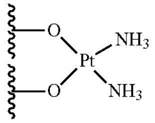 (A1) | |
| $R_3$: | 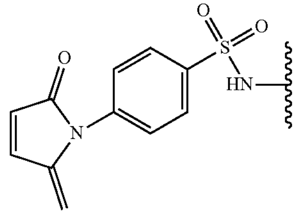 [SMILES: *NS(=O)(=O)c1ccc(N2C(=C)C=CC2=O)cc1] | 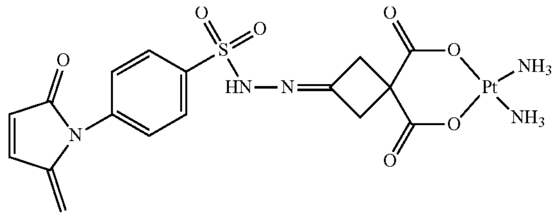 S8 |
| $R_1$, $R_2$: | 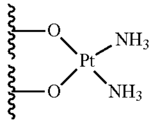 (A1) | |

TABLE 1-continued
Structures of Examples
| | Substituent | Example |
|---|---|---|
| $R_3$: | 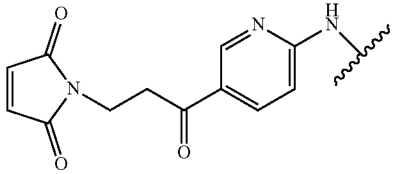 [SMILES: *Nc1ccc(C(=O)CCN2C(=O)C=CC2=O)cn1] | 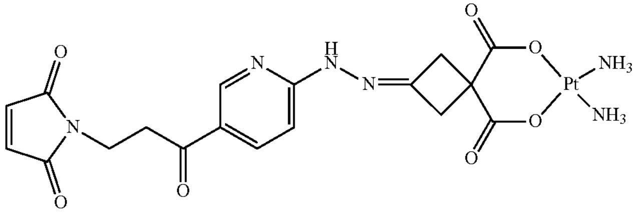 S9 |
| $R_1$, $R_2$: | 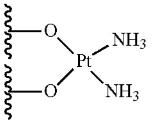 (A1) | |
| $R_3$: | 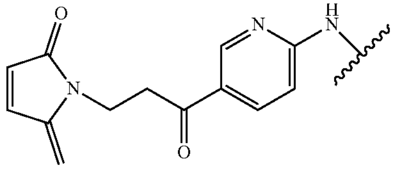 [SMILES: *Nc1ccc(C(=O)CCN2C(=C)C=CC2=O)cn1] | 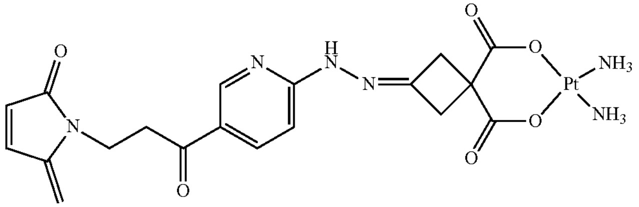 S10 |
| $R_1$, $R_2$: | 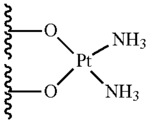 (A1) | |

TABLE 1-continued
| Structures of Examples | | |
| --- | --- | --- |
| | Substituent | Example |
| $R_3$: | 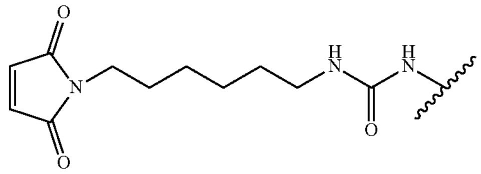 [SMILES: *NC(=O)NCCCCCCN1C(=O)C=CC1=O] | 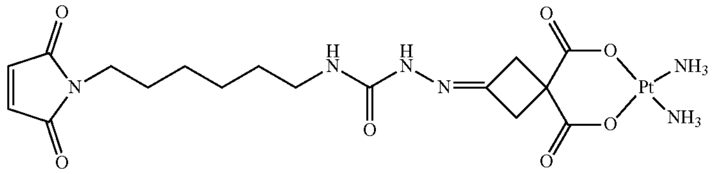<br>S11 |
| $R_1$, $R_2$: | 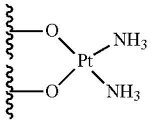<br>(A1) | |
| $R_3$: | 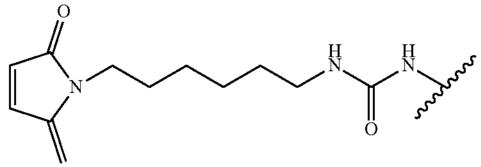 [SMILES: *NC(=O)NCCCCCCN1C(=C)C=CC1=O] | 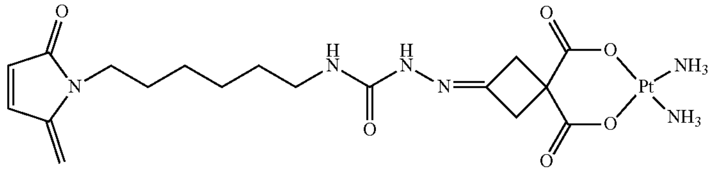<br>S12 |
| $R_1$, $R_2$: | 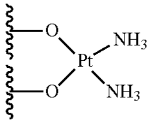<br>(A1) | |
| $R_3$: | 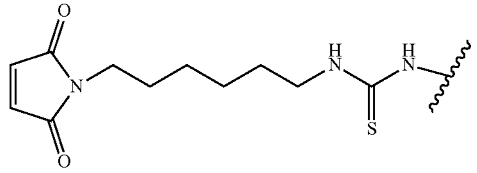 [SMILES: *NC(=S)NCCCCCCN1C(=O)C=CC1=O] | 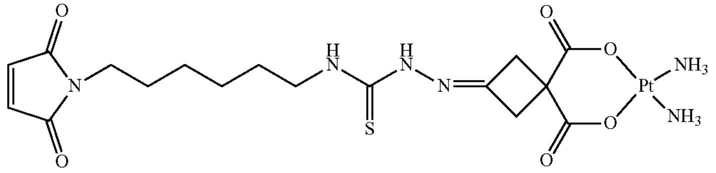<br>S13 |

TABLE 1-continued
Structures of Examples
| | Substituent | Example |
|---|---|---|
| $R_1$, $R_2$: | 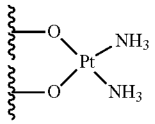 (A1) | |
| $R_3$: | 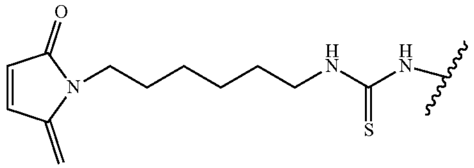 [SMILES: *NC(=S)NCCCCCCN1C(=C)C=CC1=O] | 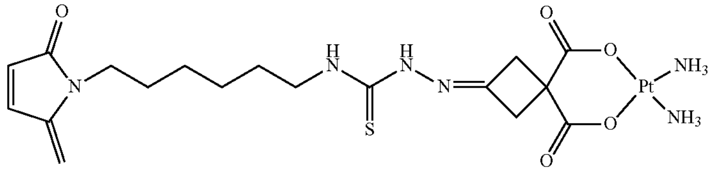 S14 |
| $R_1$, $R_2$: | 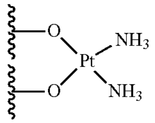 (A1) | |
| $R_3$: | 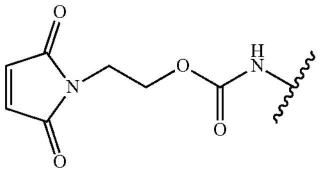 [SMILES: *NC(=O)OCCN1C(=O)C=CC1=O] | 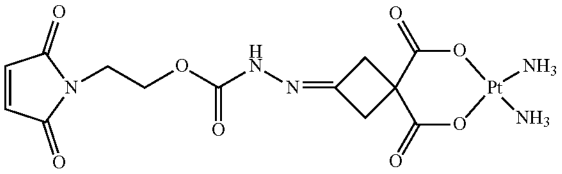 S15 |
| $R_1$, $R_2$: | 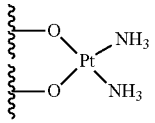 (A1) | |

TABLE 1-continued
Structures of Examples
| | Substituent | Example |
|---|---|---|
| $R_3$: | 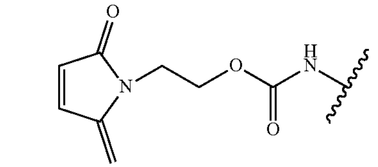 [SMILES: *NC(=O)OCCN1C(=C)C=CC1=O] | 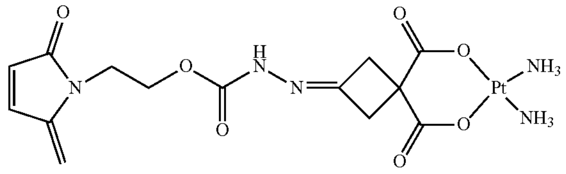 S16 |
| $R_1$, $R_2$: | 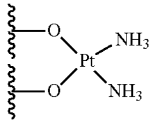 (A1) | |
| $R_3$: | 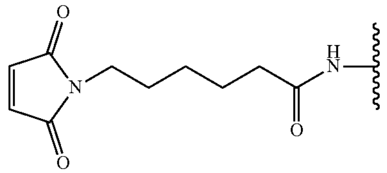 [SMILES: *NC(=O)CCCCCN1C(=O)C=CC1=O] | 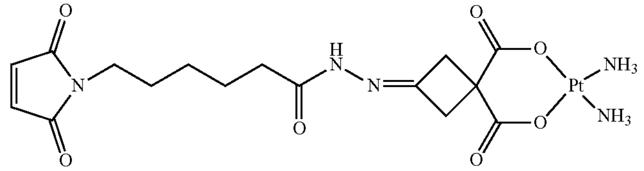 S17 |
| $R_1$, $R_2$: | 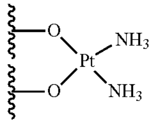 (A1) | |
| $R_3$: | 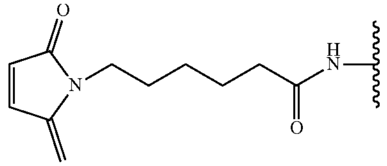 [SMILES: *NC(=O)CCCCCN1C(=C)C=CC1=O] | 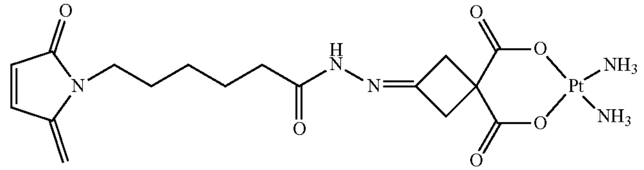 S18 |

TABLE 1-continued
Structures of Examples
| | Substituent | Example |
|---|---|---|
| $R_1$, $R_2$: | 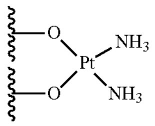 (A1) | |
| $R_3$: | 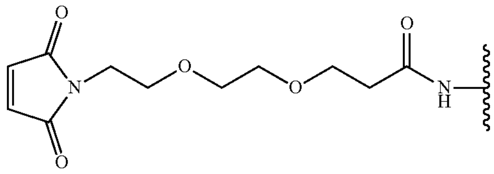 [SMILES: *NC(=O)CCOCCOCCN1C(=O)C=CC1=O] | 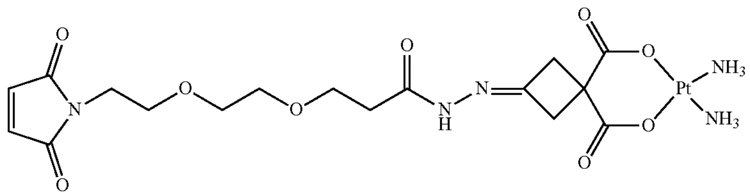 S19 |
| $R_1$, $R_2$: | 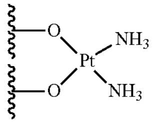 (A1) | |
| $R_3$: | 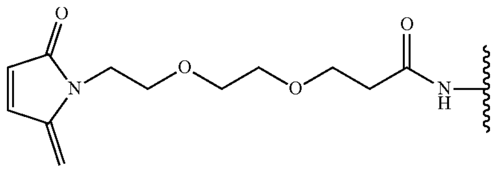 [SMILES: *NC(=O)CCOCCOCCN1C(=C)C=CC1=O] | 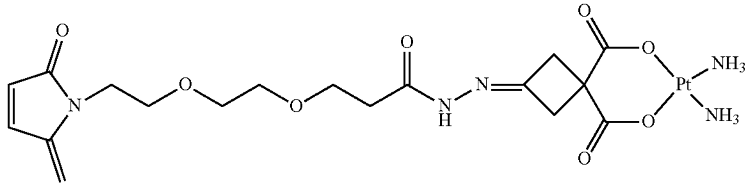 S20 |
| $R_1$, $R_2$: | 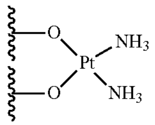 (A1) | |

TABLE 1-continued
| Structures of Examples | | |
|---|---|---|
| | Substituent | Example |
| $R_3$: | 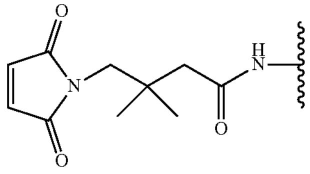 [SMILES: *NC(=O)CC(C)(C)CN1C(=O)C=CC1=O] | 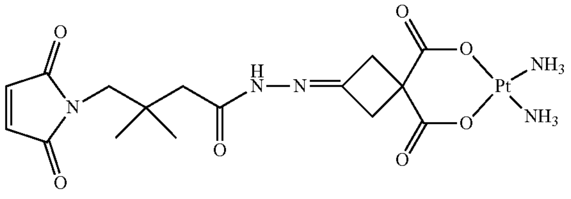 S21 |
| $R_1$, $R_2$: | 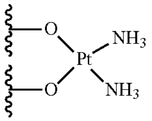 (A1) | |
| $R_3$: | 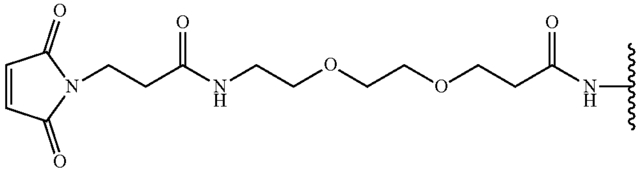 [SMILES: *NC(=O)CCOCCOCCNC(=O)CCN1C(=O)C=CC1=O] | 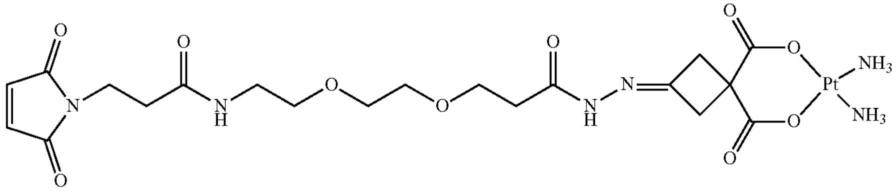 S22 |
| $R_1$, $R_2$: | 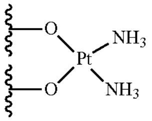 (A1) | |

TABLE 1-continued
| Structures of Examples | | |
|---|---|---|
| | Substituent | Example |
| $R_3$: | 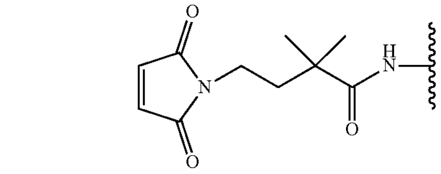 [SMILES: *NC(=O)C(C)(C)CCN1C(=O)C=CC1=O] | 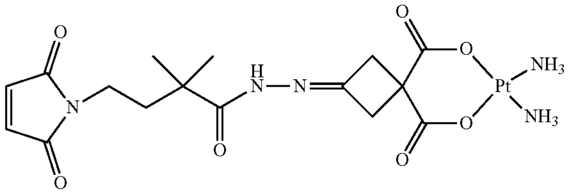<br>S23 |
| $R_1$, $R_2$: | 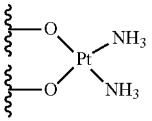<br>(A1) | |
| $R_3$: | 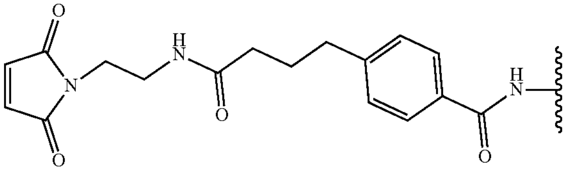 [SMILES: *NC(=O)c1ccc(CCCC(=O)NCCN2C(=O)C=CC2=O)cc1] | 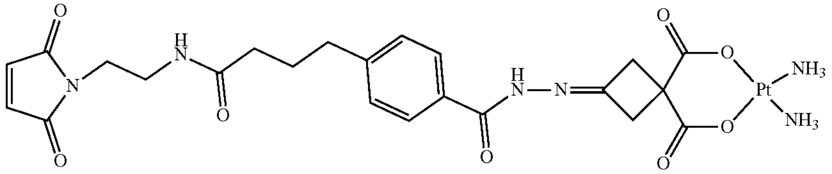<br>S24 |
| $R_1$, $R_2$: | 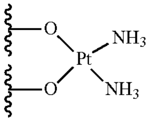<br>(A1) | |
| $R_3$: | 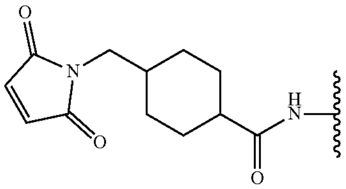 [SMILES: *NC(=O)C1CCC(CN2C(=O)C=CC2=O)CC1] | 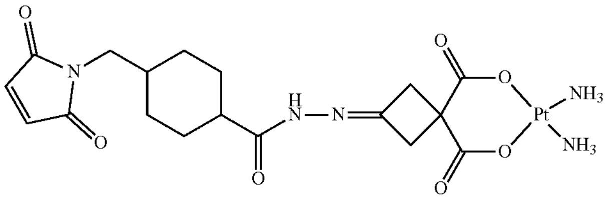<br>S25 |

TABLE 1-continued
Structures of Examples
| | Substituent | Example |
|---|---|---|
| $R_1$, $R_2$: | 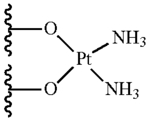 (A1) | |
| $R_3$: | 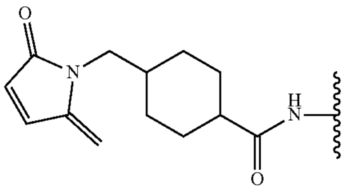 [SMILES: *NC(=O)C1CCC(CN2C(=C)C=CC2=O)CC1] | 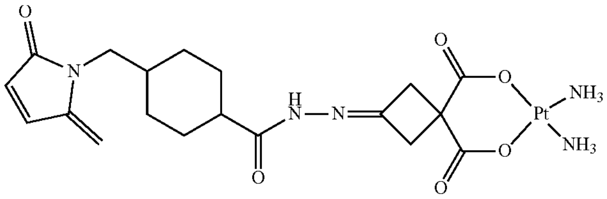 S26 |
| $R_1$, $R_2$: | 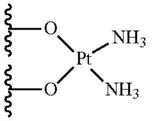 (A1) | |
| $R_3$: | 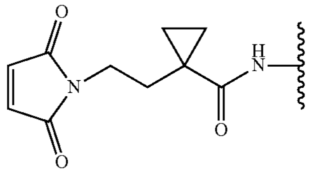 [SMILES: *NC(=O)C1(CCN2C(=O)C=CC2=O)CC1] | 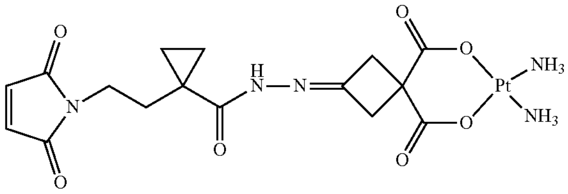 S27 |
| $R_1$, $R_2$: | 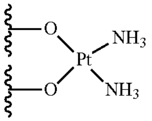 (A1) | |

TABLE 1-continued
| Structures of Examples | | |
|---|---|---|
| | Substituent | Example |
| $R_3$: | 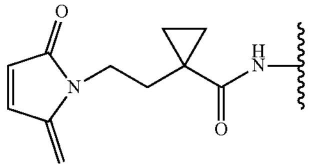 [SMILES: *NC(=O)C1(CCN2C(=C)C=CC2=O)CC1] | 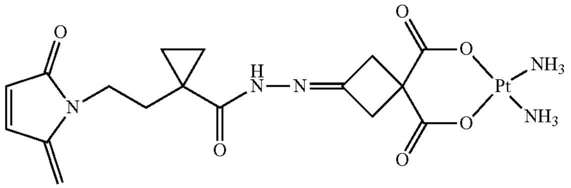<br>S28 |
| $R_1$, $R_2$: | 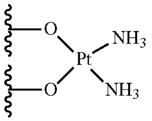<br>(A1) | |
| $R_3$: | 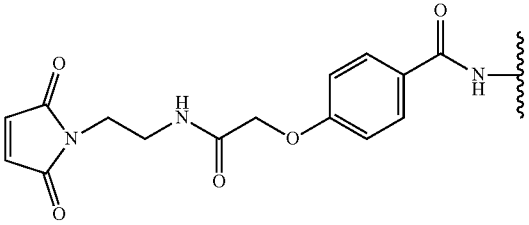 [SMILES: *NC(=O)c1ccc(OCC(=O)NCCN2C(=O)C=CC2=O)cc1] | 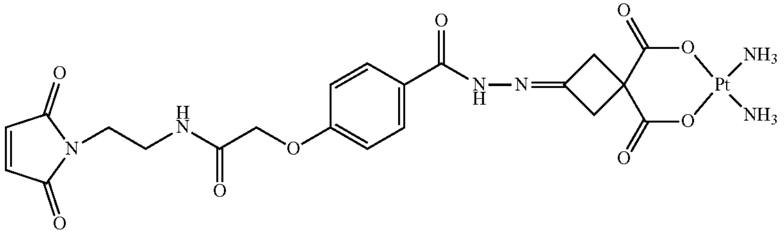<br>S29 |
| $R_1$, $R_2$: | 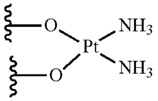<br>(A1) | |

TABLE 1-continued
Structures of Examples
| Substituent | | Example |
|---|---|---|
| R$_3$: | 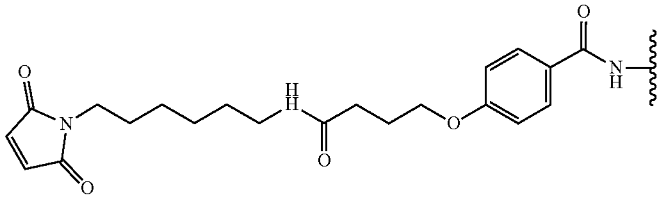 | 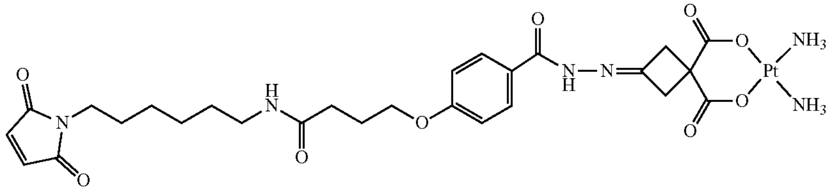 S30 |
| R$_1$, R$_2$: | 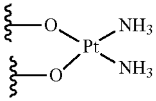 (A1) | |
| R$_3$: | 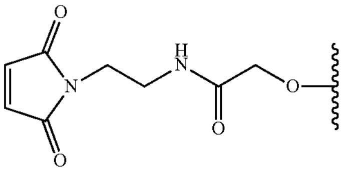 [SMILES: *OCC(=O)NCCN1C(=O)C=CC1=O] | 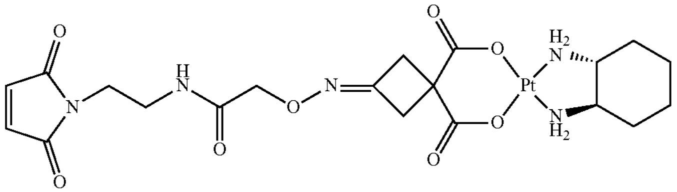 S31 |
| R$_1$, R$_2$: | 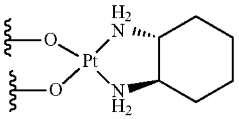 (A2) | |
| R$_3$: | 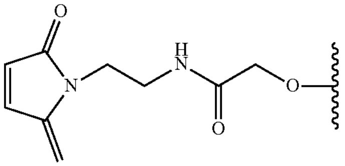 [SMILES: *OCC(=O)NCCN1C(=C)C=CC1=O] | 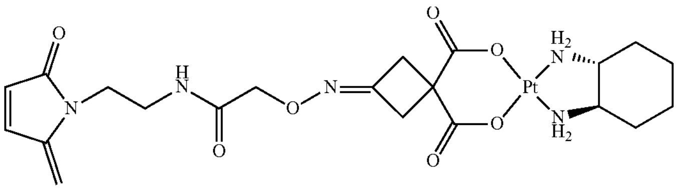 S32 |

TABLE 1-continued
| Structures of Examples | | |
|---|---|---|
| | Substituent | Example |
| R₁, R₂: | 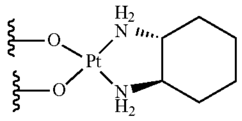<br>(A2) | |
| R₃: | 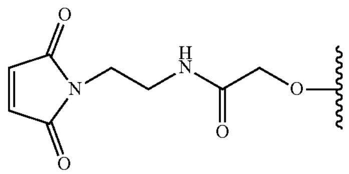 [SMILES: *OCC(=O)NCCN1C(=O)C=CC1=O] | 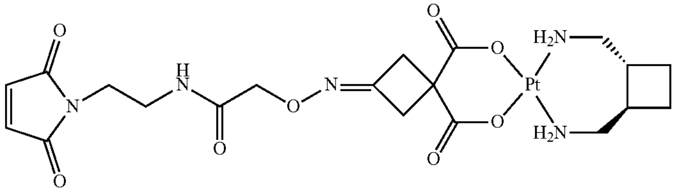<br>S33 |
| R₁, R₂: | 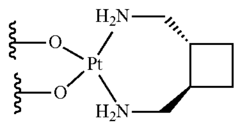<br>(A3) | |
| R₃: | 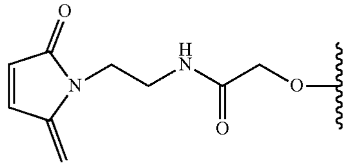 [SMILES: *OCC(=O)NCCN1C(=C)C=CC1=O] | 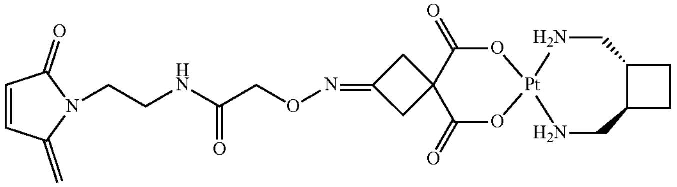<br>S34 |
| R₁, R₂: | 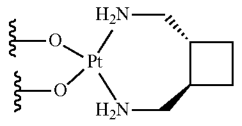<br>(A3) | |

TABLE 1-continued
| Structures of Examples | | |
|---|---|---|
| | Substituent | Example |
| $R_3$: | 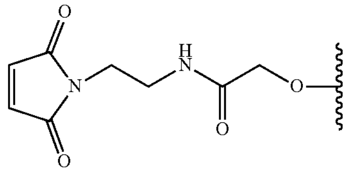 | 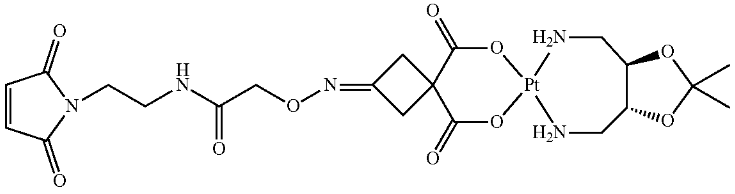 S35 |
| $R_1$, $R_2$: | 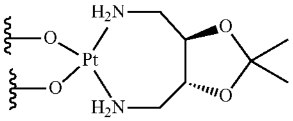 (A4) | |
| $R_3$: | 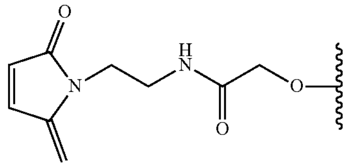 [SMILES: *OCC(=O)NCCN1C(=C)C=CC1=O] | 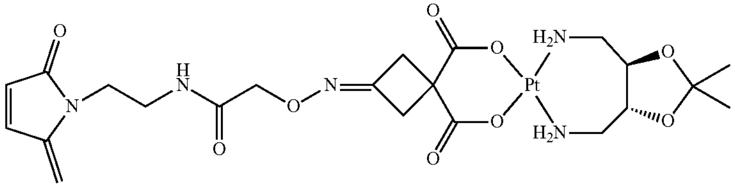 S36 |
| $R_1$, $R_2$: | 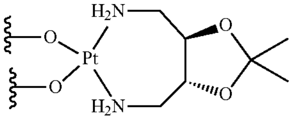 (A4) | |

TABLE 1-continued
| Structures of Examples | | |
|---|---|---|
| | Substituent | Example |
| $R_3$: | 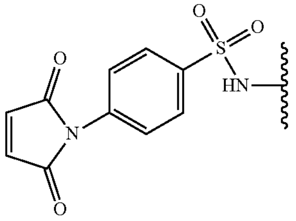 [SMILES: *NS(=O)(=O)c1ccc(N2C(=O)C=CC2=O)cc1] | 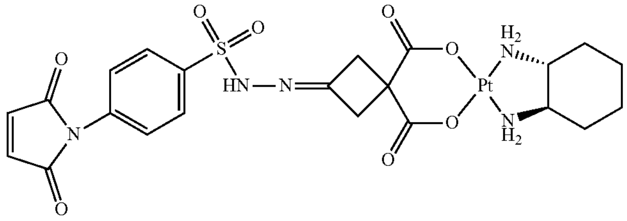<br>S37 |
| $R_1$, $R_2$: | 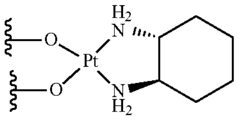<br>(A2) | |
| $R_3$: | 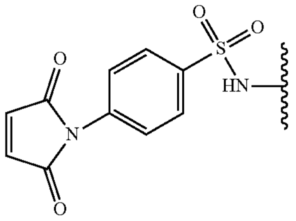 [SMILES: *NS(=O)(=O)c1ccc(N2C(=O)C=CC2=O)cc1] | 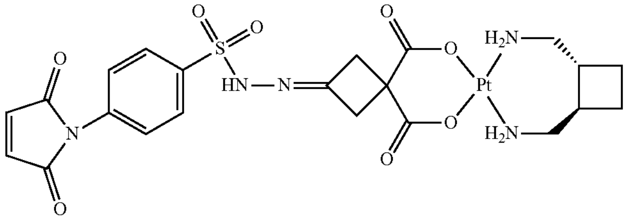<br>S38 |
| $R_1$, $R_2$: | 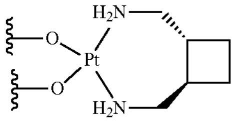<br>(A3) | |

TABLE 1-continued
Structures of Examples
| | Substituent | Example |
|---|---|---|
| $R_3$: | 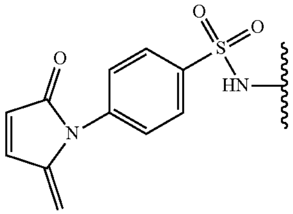 [SMILES: *NS(=O)(=O)c1ccc(N2C(=C)C=CC2=O)cc1] | 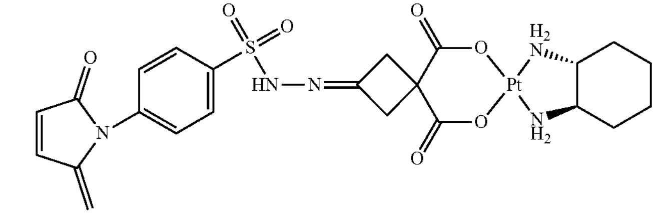 S39 |
| $R_1$, $R_2$: | 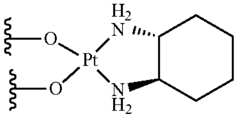 (A2) | |
| $R_3$: | 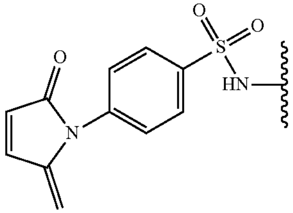 [SMILES: *NS(=O)(=O)c1ccc(N2C(=C)C=CC2=O)cc1] | 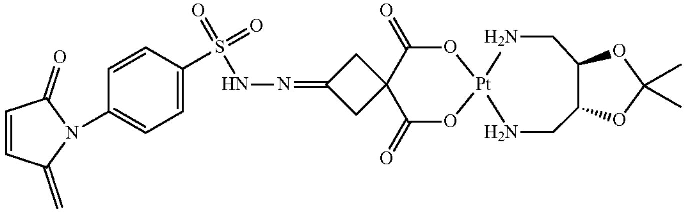 S40 |
| $R_1$, $R_2$: | 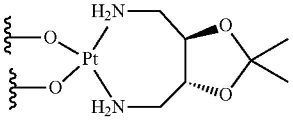 (A4) | |

TABLE 1-continued
Structures of Examples
| | Substituent | Example |
|---|---|---|
| $R_3$: | 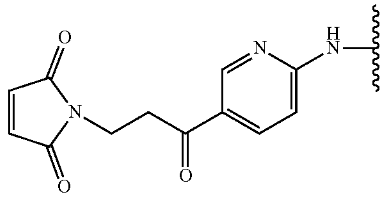 [SMILES: *Nc1ccc(C(=O)CCN2C(=O)C=CC2=O)cn1] | 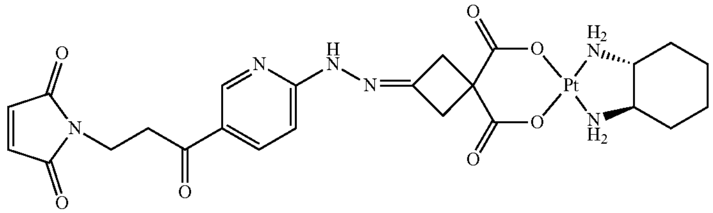 S41 |
| $R_1$, $R_2$: | 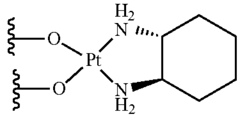 (A2) | |
| $R_3$: | 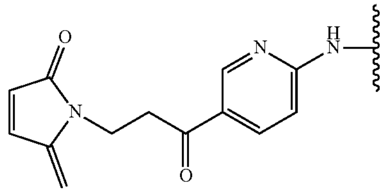 [SMILES: *Nc1ccc(C(=O)CCN2C(=C)C=CC2=O)cn1] | 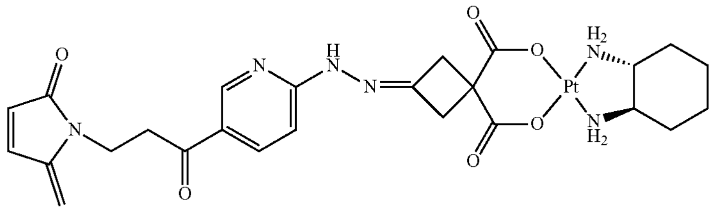 S42 |
| $R_1$, $R_2$: | 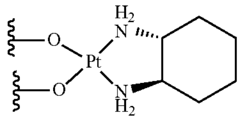 (A2) | |

TABLE 1-continued
| Structures of Examples | | |
|---|---|---|
| | Substituent | Example |
| $R_3$: | 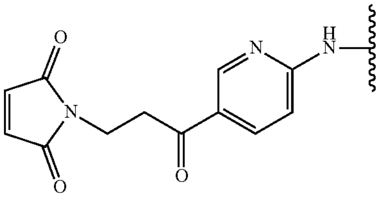 [SMILES: *Nc1ccc(C(=O)CCN2C(=O)C=CC2=O)cn1] | 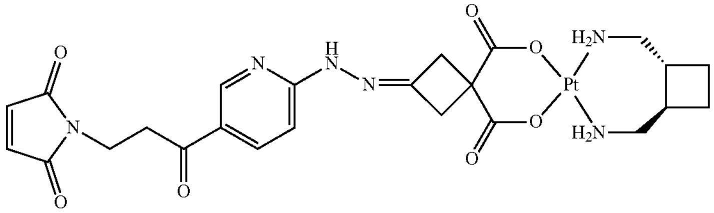 S43 |
| $R_1$, $R_2$: | 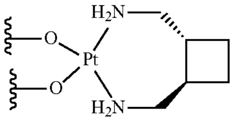 (A3) | |
| $R_3$: | 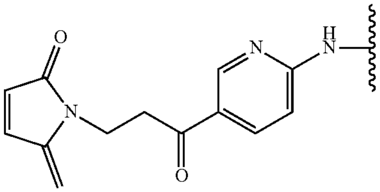 [SMILES: *Nc1ccc(C(=O)CCN2C(=C)C=CC2=O)cn1] | 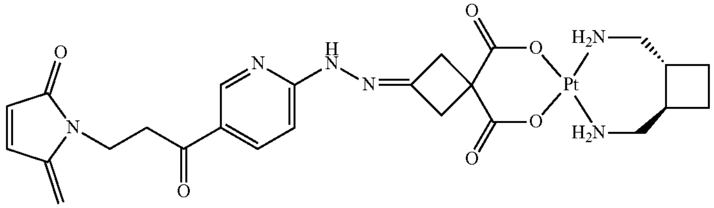 S44 |
| $R_1$, $R_2$: | 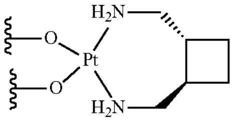 (A3) | |

TABLE 1-continued
Structures of Examples
| | Substituent | Example |
|---|---|---|
| $R_3$: | 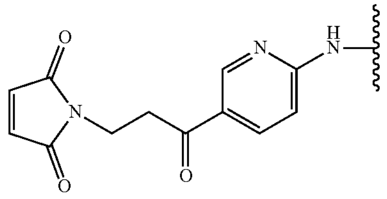 [SMILES: *Nc1ccc(C(=O)CCN2C(=O)C=CC2=O)cn1] | 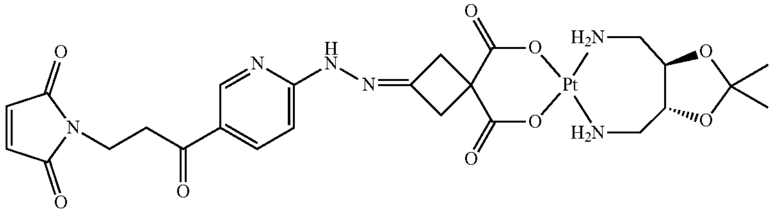<br>S45 |
| $R_1$, $R_2$: | 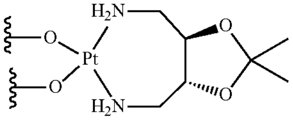<br>(A4) | |
| $R_3$: | 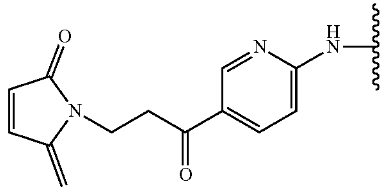 [SMILES: *Nc1ccc(C(=O)CCN2C(=C)C=CC2=O)cn1] | 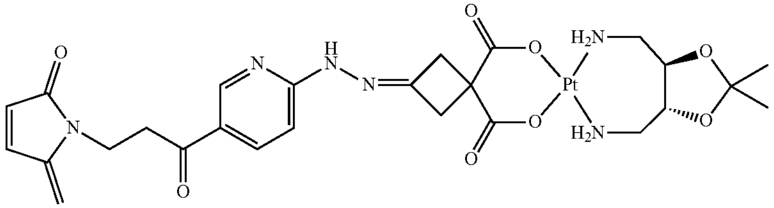<br>S46 |
| $R_1$, $R_2$: | 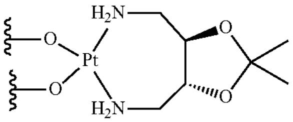<br>(A4) | |

TABLE 1-continued
| Structures of Examples | | |
|---|---|---|
| | Substituent | Example |
| $R_3$: | 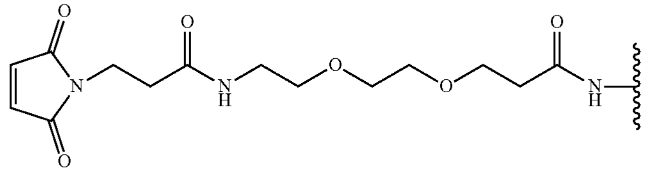 [SMILES: *NC(=O)CCOCCOCCNC(=O)CCN1C(=O)C=CC1=O] | 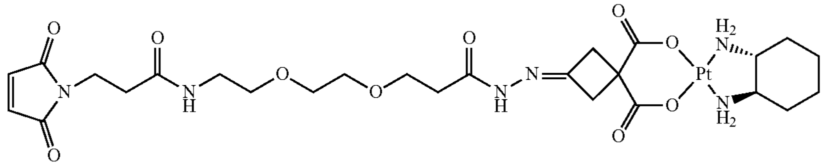 S47 |
| $R_1$, $R_2$: | 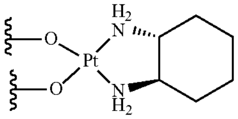 (A2) | |
| $R_3$: | 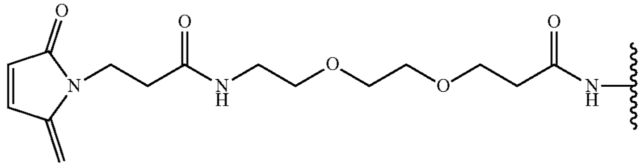 [SMILES: *NC(=O)CCOCCOCCNC(=O)CCN1C(=C)C=CC1=O] | 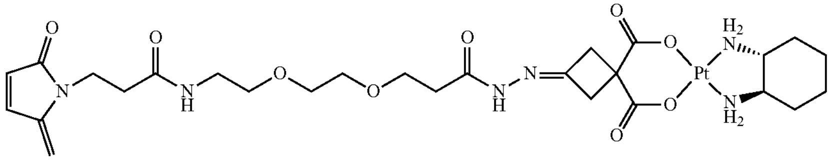 S48 |
| $R_1$, $R_2$: | 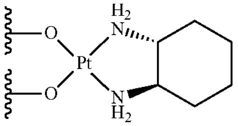 (A2) | |
| $R_3$: | 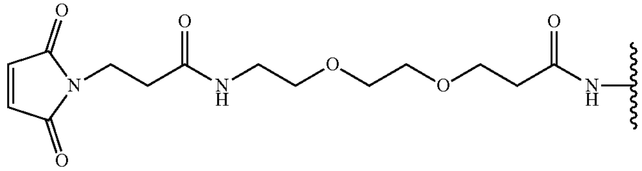 [SMILES: *NC(=O)CCOCCOCCNC(=O)CCN1C(=O)C=CC1=O] | 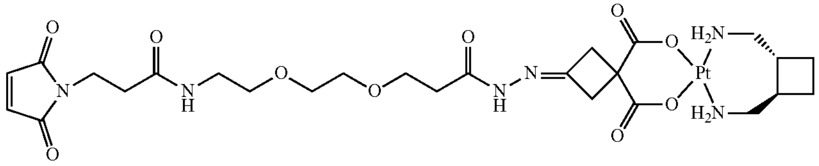 S49 |

TABLE 1-continued
Structures of Examples
| | Substituent | Example |
|---|---|---|
| $R_1$, $R_2$: | 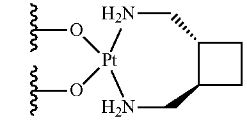 (A3) | |
| $R_3$: | 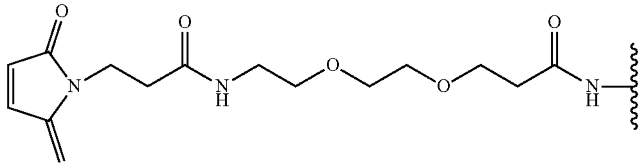 [SMILES: *NC(=O)CCOCCOCCNC(=O)CCN1C(=C)C=CC1=O] | 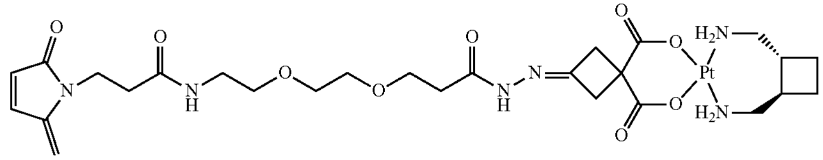 S50 |
| $R_1$, $R_2$: | 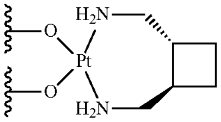 (A3) | |
| $R_3$: | 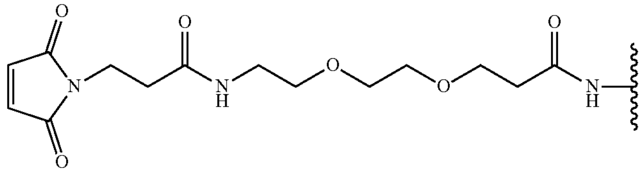 [SMILES: *NC(=O)CCOCCOCCNC(=O)CCN1C(=O)C=CC1=O] | 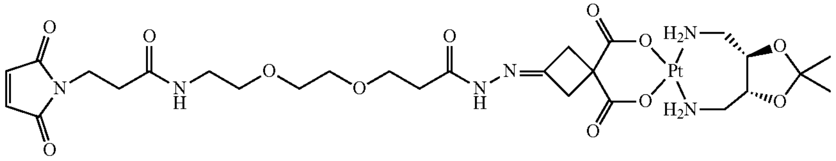 S51 |
| $R_1$, $R_2$: | 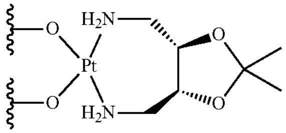 (A4) | |

TABLE 1-continued
| Structures of Examples | | |
|---|---|---|
| | Substituent | Example |
| $R_3$: | 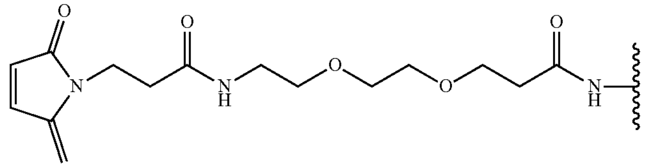 [SMILES: *NC(=O)CCOCCOCCNC(=O)CCN1C(=C)C=CC1=O] | 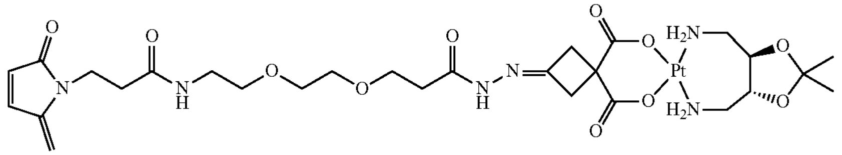 S52 |
| $R_1$, $R_2$: | 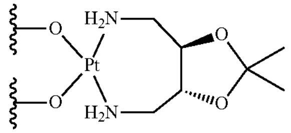 (A4) | |
| $R_3$: | 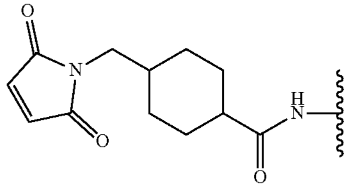 | 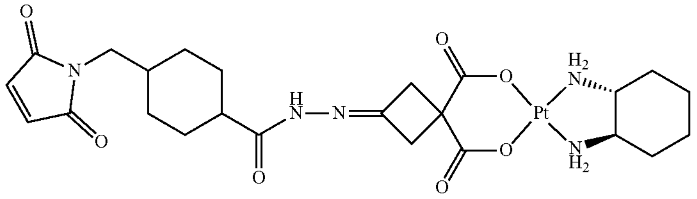 S53 |
| $R_1$, $R_2$: | 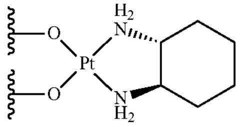 (A2) | |

TABLE 1-continued
Structures of Examples
| | Substituent | Example |
| --- | --- | --- |
| $R_3$: | 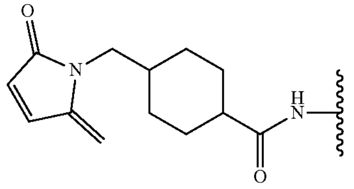 | 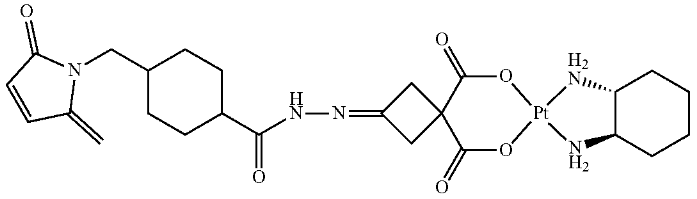<br>S54 |
| $R_1$, $R_2$: | 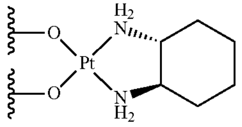<br>(A2) | |
| $R_3$: | 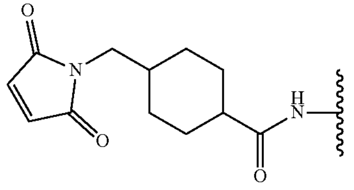 | 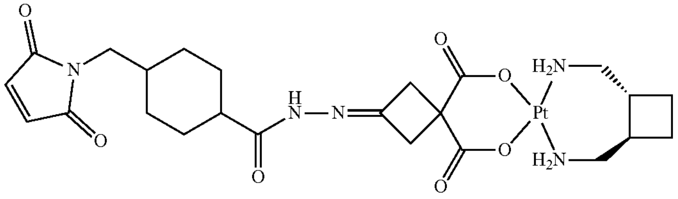<br>S55 |
| $R_1$, $R_2$: | 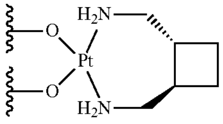<br>(A3) | |

TABLE 1-continued
| Structures of Examples | | |
|---|---|---|
| | Substituent | Example |
| $R_3$: | 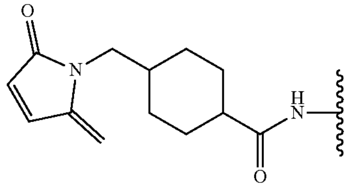 | 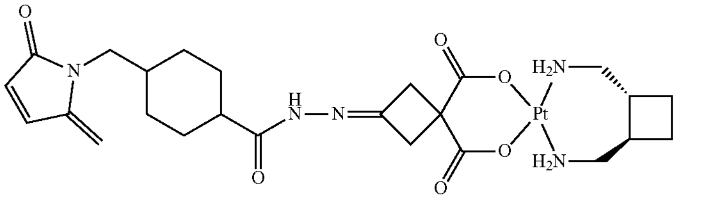<br>S56 |
| $R_1$, $R_2$: | 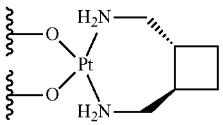<br>(A3) | |
| $R_3$: | 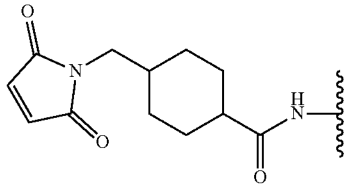 | 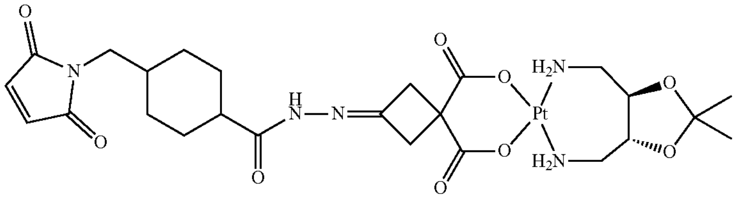<br>S57 |
| $R_1$, $R_2$: | 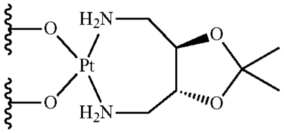<br>(A4) | |

TABLE 1-continued
| Structures of Examples | | |
|---|---|---|
| | Substituent | Example |
| $R_3$: | 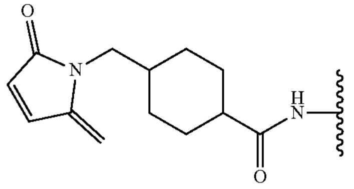 | 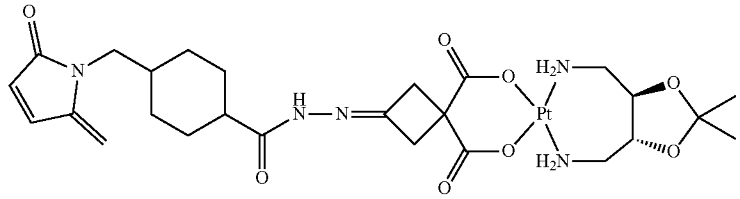<br>S58 |
| $R_1$, $R_2$: | 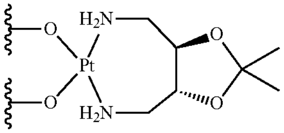<br>(A4) | |
| $R_3$: | 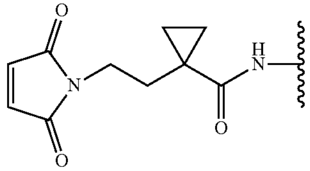 [SMILES: *NC(=O)C1(CCN2C(=O)C=CC2=O)CC1] | 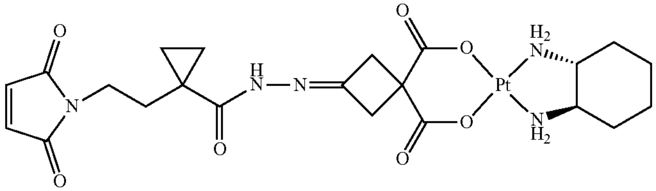<br>S59 |
| $R_1$, $R_2$: | 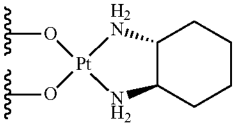<br>(A2) | |

TABLE 1-continued
| Structures of Examples | | |
|---|---|---|
| | Substituent | Example |
| $R_3$: | 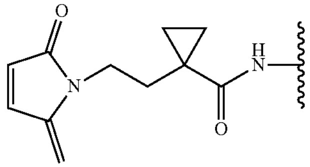 [SMILES: *NC(=O)C1(CCN2C(=C)C=CC2=O)CC1] | 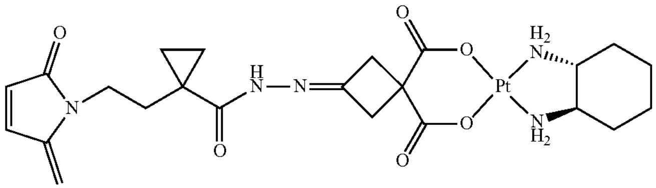 S60 |
| $R_1$, $R_2$: | 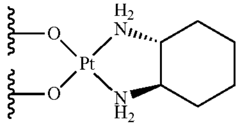 (A2) | |
| $R_3$: | 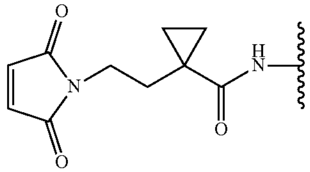 [SMILES: *NC(=O)C1(CCN2C(=O)C=CC2=O)CC1] | 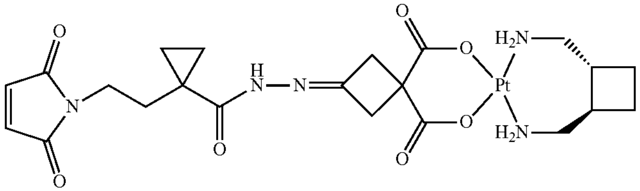 S61 |
| $R_1$, $R_2$: | 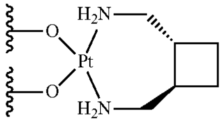 (A3) | |

TABLE 1-continued
| Structures of Examples | | |
|---|---|---|
| | Substituent | Example |
| $R_3$: | 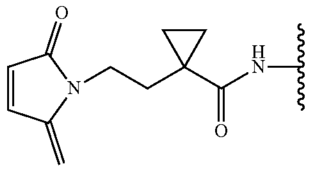 [SMILES: *NC(=O)C1(CCN2C(=C)C=CC2=O)CC1] | 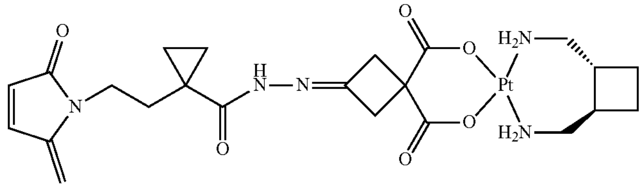<br>S62 |
| $R_1$, $R_2$: | 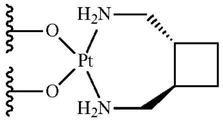<br>(A3) | |
| $R_3$: | 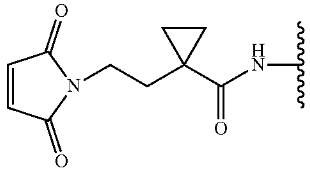 | 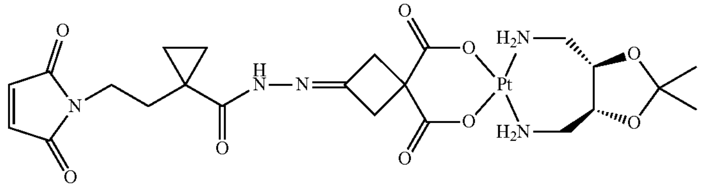<br>S63 |
| $R_1$, $R_2$: | 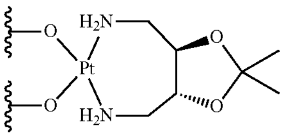<br>(A4) | |

TABLE 1-continued
| Structures of Examples | | |
|---|---|---|
| | Substituent | Example |
| $R_3$: | 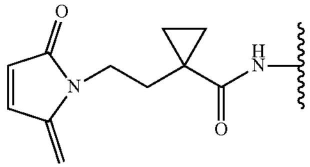 [SMILES: *NC(=O)C1(CCN2C(=C)C=CC2=O)CC1] | 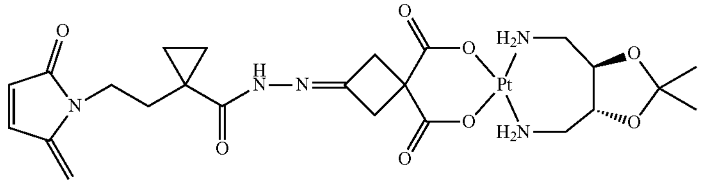 S64 |
| $R_1$, $R_2$: | 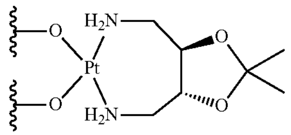 (A4) | |
| $R_3$: | 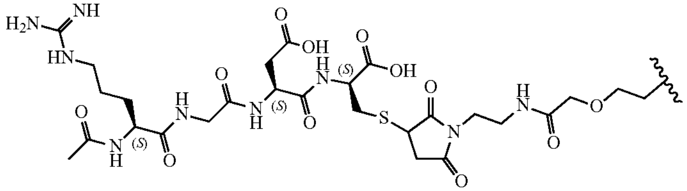 | 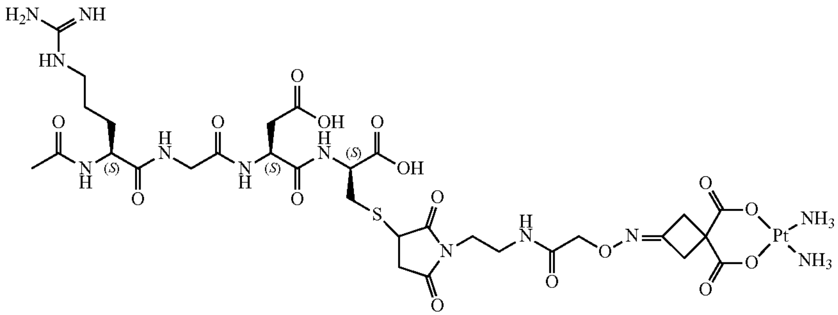 S65 |
| $R_1$, $R_2$: | 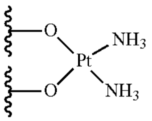 (A1) | |

TABLE 1-continued
| Structures of Examples | | |
|---|---|---|
| | Substituent | Example |
| $R_3$: | 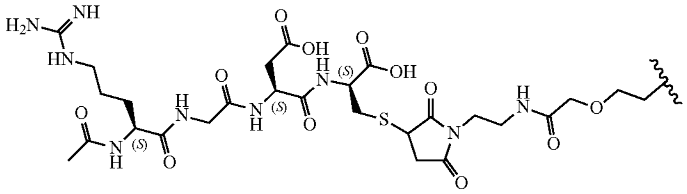 | 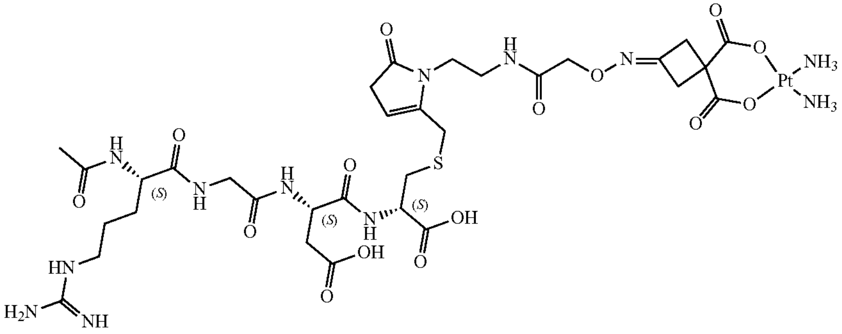<br>S66 |
| $R_1$, $R_2$: | 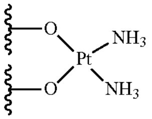<br>(A1) | |
| $R_3$: | 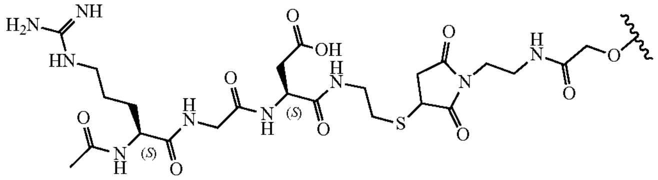 | 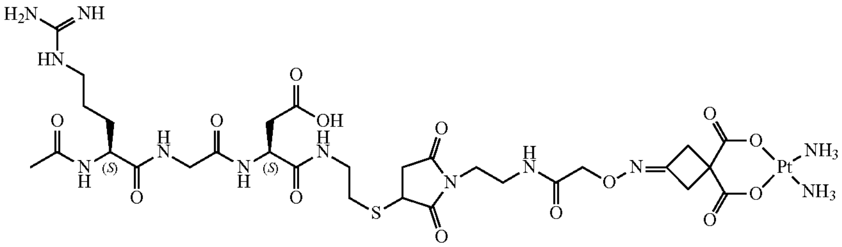<br>S67 |
| $R_1$, $R_2$: | 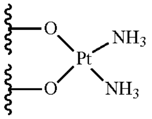<br>(A1) | |

TABLE 1-continued
| Structures of Examples | | |
|---|---|---|
| | Substituent | Example |
| $R_3$: | 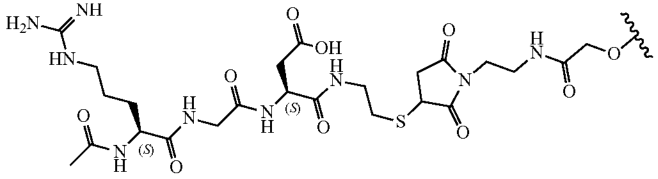 | 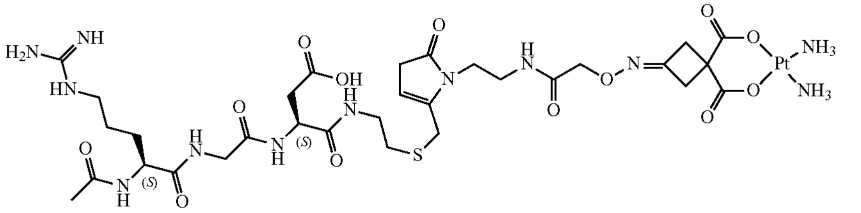 S68 |
| $R_1$, $R_2$: | 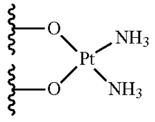 (A1) | |
| $R_3$: | 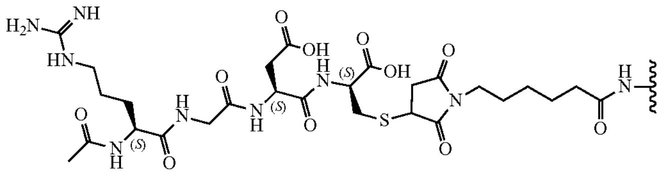 | 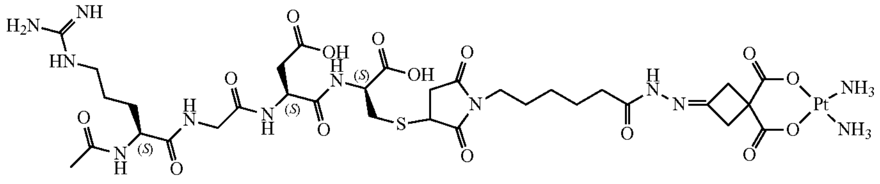 S69 |
| $R_1$, $R_2$: | 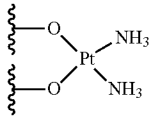 (A1) | |

TABLE 1-continued
| Structures of Examples | | |
|---|---|---|
| | Substituent | Example |
| $R_3$: | 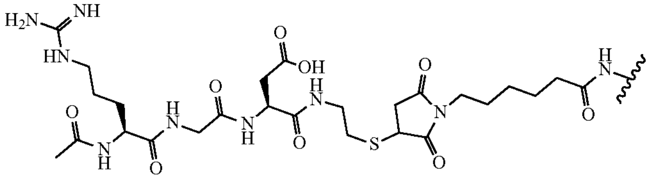 [SMILES: *NC(=O)CCCCCN1C(=O)CC(SCCNC(=O)[C@H](CC(=O)O)NC(=O)CNC(=O)[C@H](CCCNC(=N)N)NC(C)=O)C1=O] | 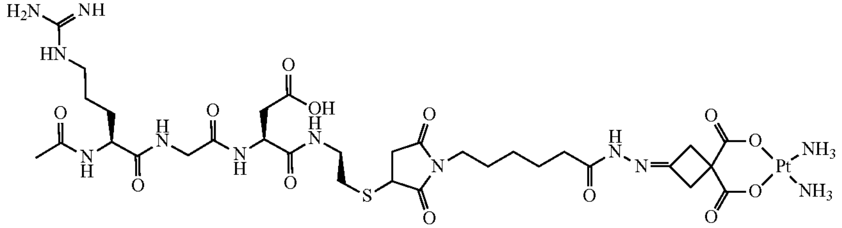<br>S70 |
| $R_1$, $R_2$: | 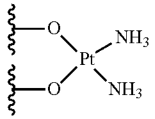<br>(A1) | |
| $R_3$: | 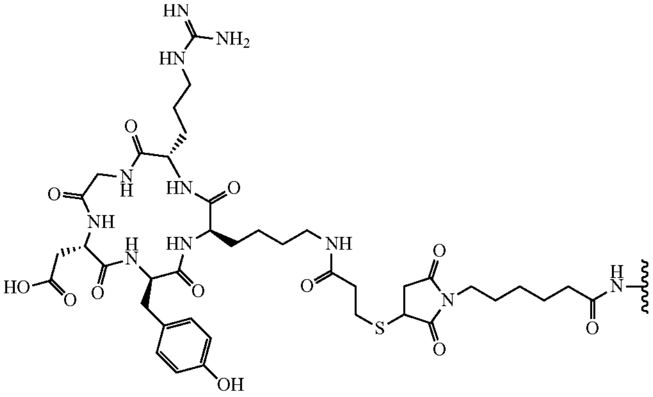 [SMILES: *NC(=O)CCCCCN1C(=O)CC(SCCC(=O)NCCCC[C@H]2NC(=O)[C@@H](Cc3ccc(O)cc3)NC(=O)[C@H](CC(=O)O)NC(=O)CNC(=O)[C@H](CCCNC(=N)N)NC2=O)C1=O] | 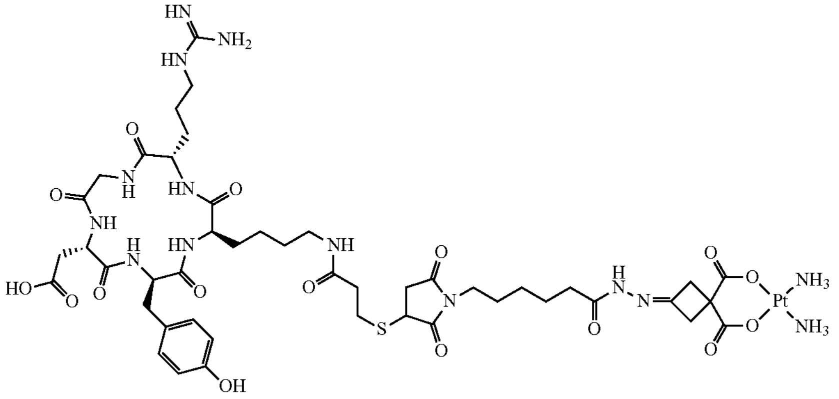<br>S71 |
| $R_1$, $R_2$: | 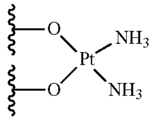<br>(A1) | |

TABLE 1-continued
| Structures of Examples | |
|---|---|
| Substituent | Example |
| R3: 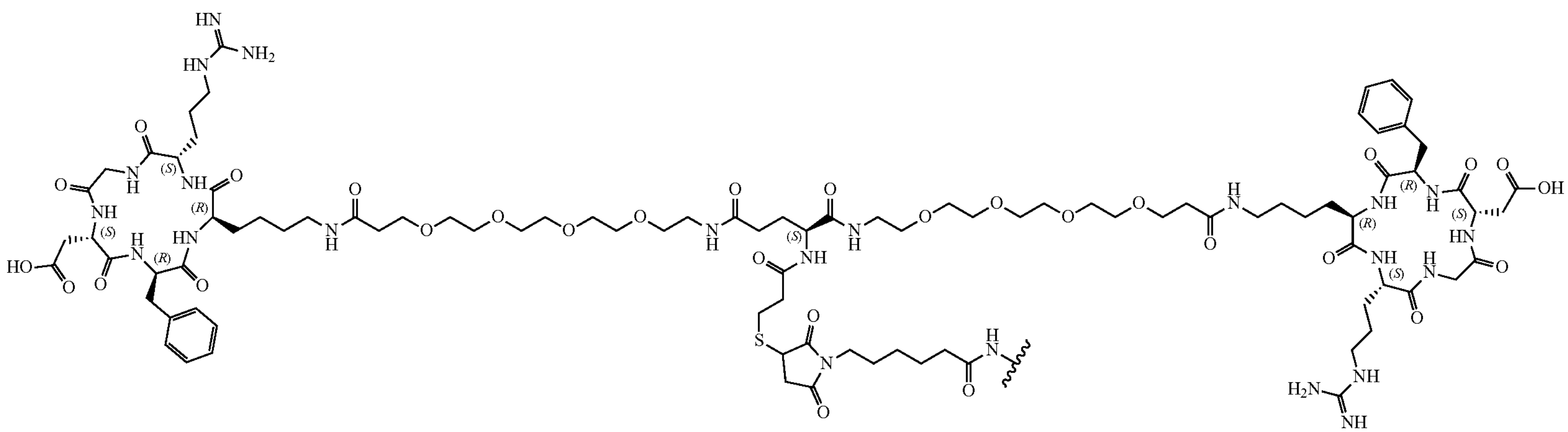 | |
| R1, R2: 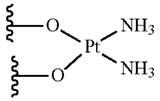 (A1) | |

TABLE 1-continued
| Structures of Examples | |
|---|---|
| Substituent | Example |
| Example: 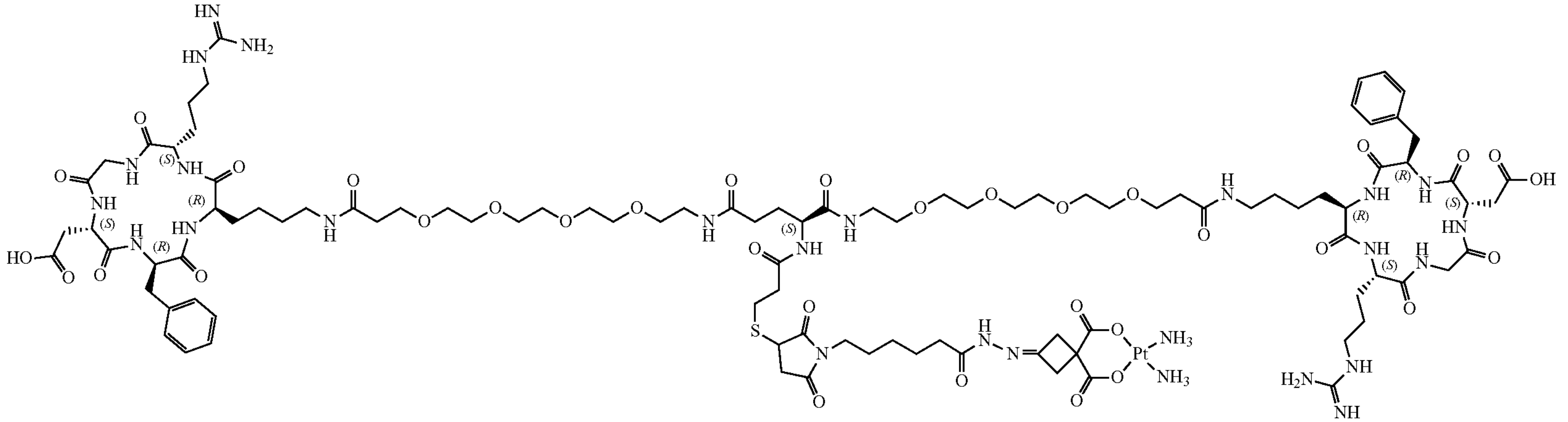 S72 | |
| R₃: 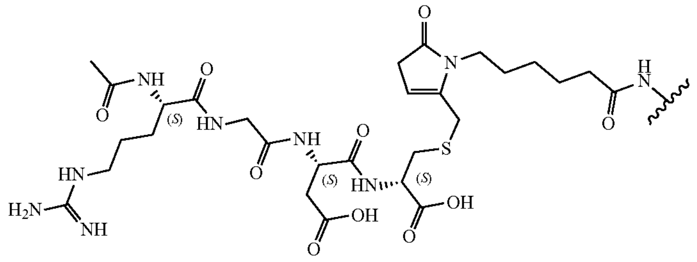 | 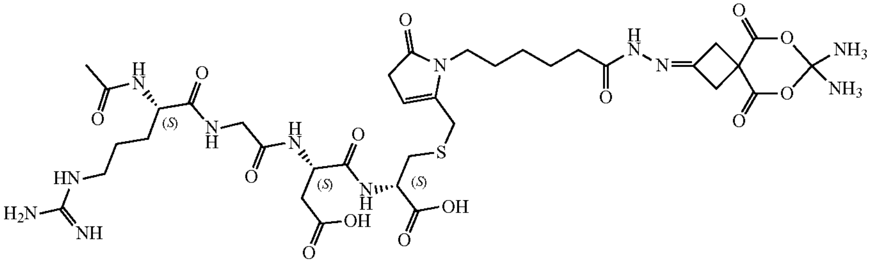 S73 |
| R₁, R₂: 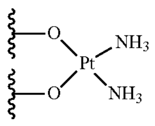 (A1) | |

TABLE 1-continued
Structures of Examples
| Substituent | | Example |
|---|---|---|
| $R_3$: | 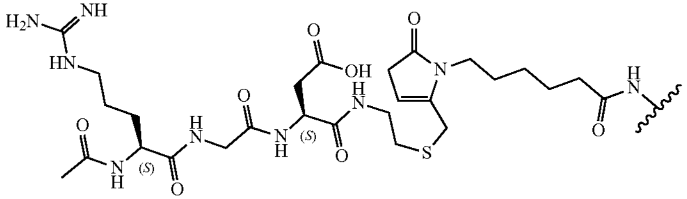 | 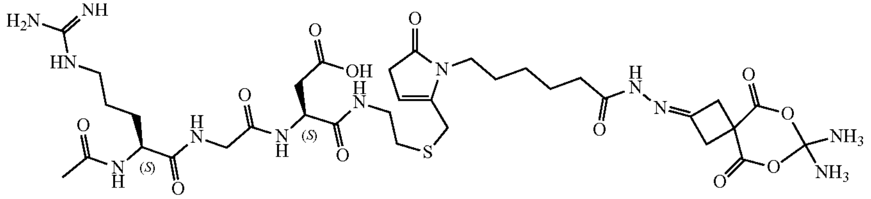 S74 |
| $R_1$, $R_2$: | 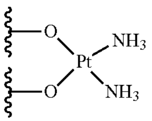 (A1) | |
| $R_3$: | 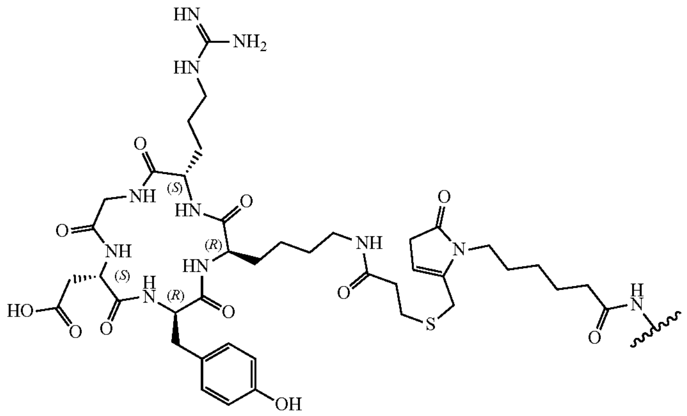 | 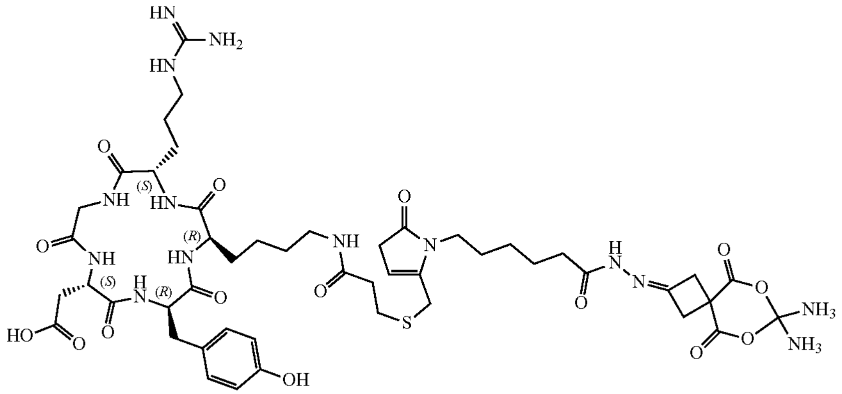 S75 |
| $R_1$, $R_2$: | 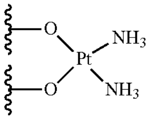 (A1) | |

TABLE 1-continued
| Structures of Examples | |
|---|---|
| Substituent | Example |
| R3: | |
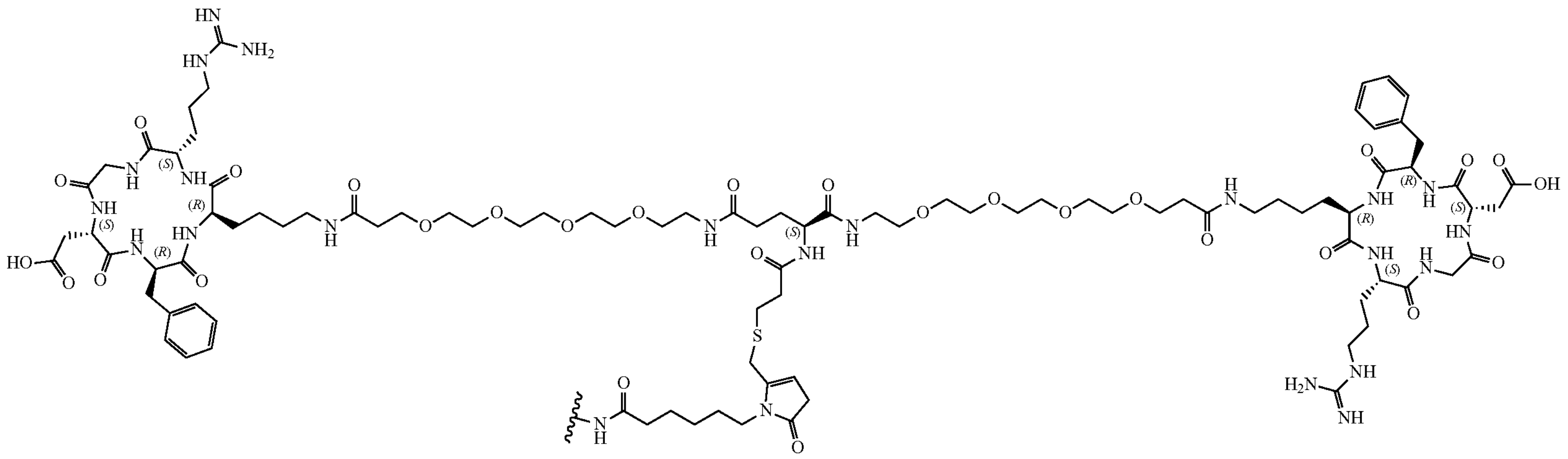
$R_1$, $R_2$:
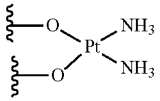
(A1)

TABLE 1-continued
Structures of Examples
| Substituent | Example |
| --- | --- |
| Example: 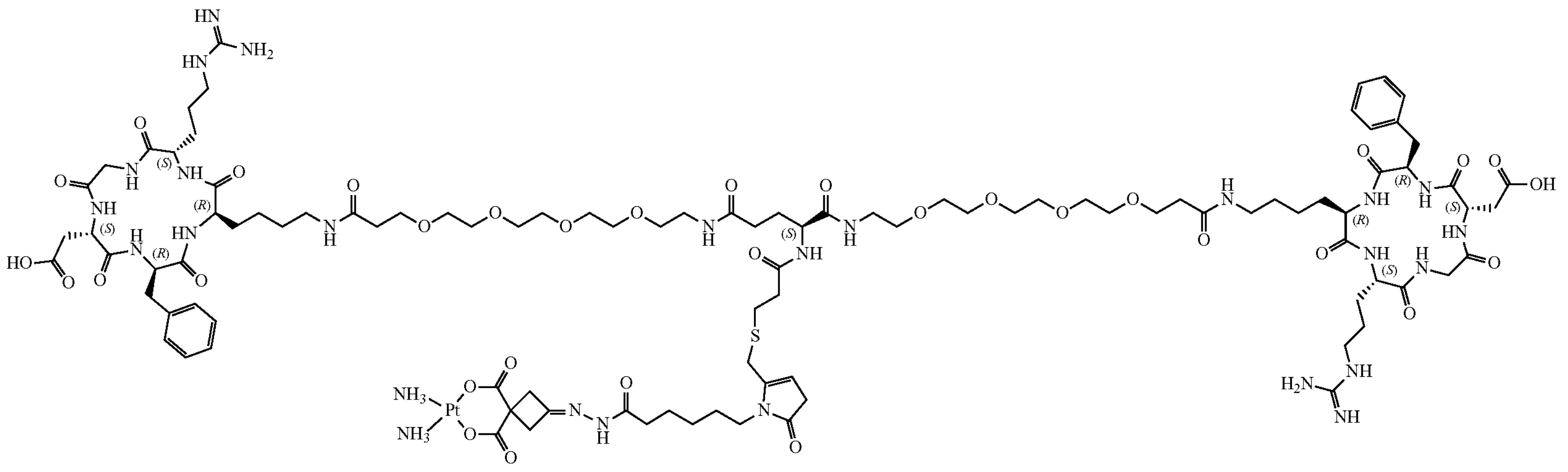 | S76 |
| $R_3$: 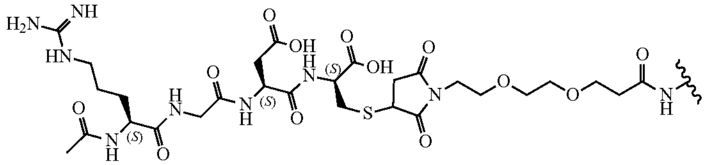 | 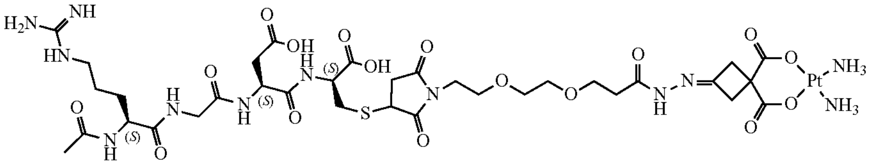 S77 |
| $R_1$, $R_2$: 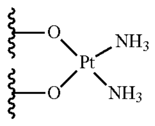 (A1) | |

TABLE 1-continued
Structures of Examples
| Substituent | | Example |
|---|---|---|
| $R_3$: | 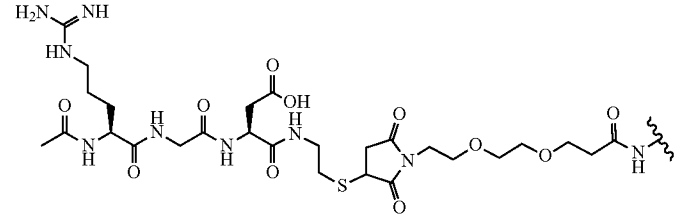 [SMILES: *NC(=O)CCOCCOCCN1C(=O)CC(SCCNC(=O)[C@H](CC(=O)O)NC(=O)CNC(=O)[C@H](CCCNC(=N)N)NC(C)=O)C1=O] | 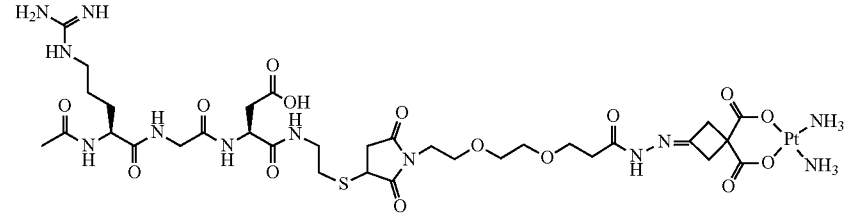 S78 |
| $R_1$, $R_2$: | 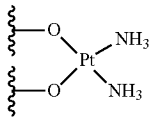 (A1) | |
| $R_3$: | 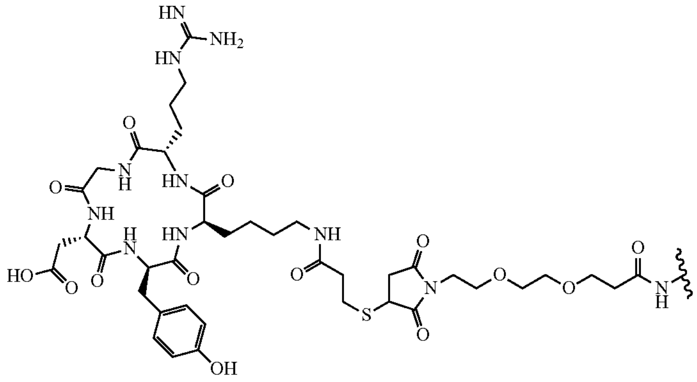 [SMILES: *NC(=O)CCOCCOCCN1C(=O)CC(SCCC(=O)NCCCC[C@H]2NC(=O)[C@@H](Cc3ccc(O)cc3)NC(=O)[C@H](CC(=O)O)NC(=O)CNC(=O)[C@H](CCCNC(=N)N)NC2=O)C1=O] | 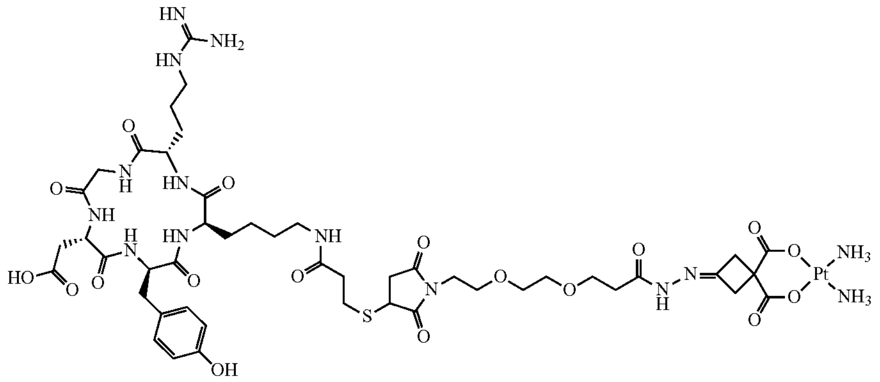 S79 |
| $R_1$, $R_2$: | 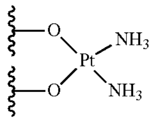 (A1) | |

TABLE 1-continued
| Structures of Examples | |
|---|---|
| Substituent | Example |
| R$_3$: | 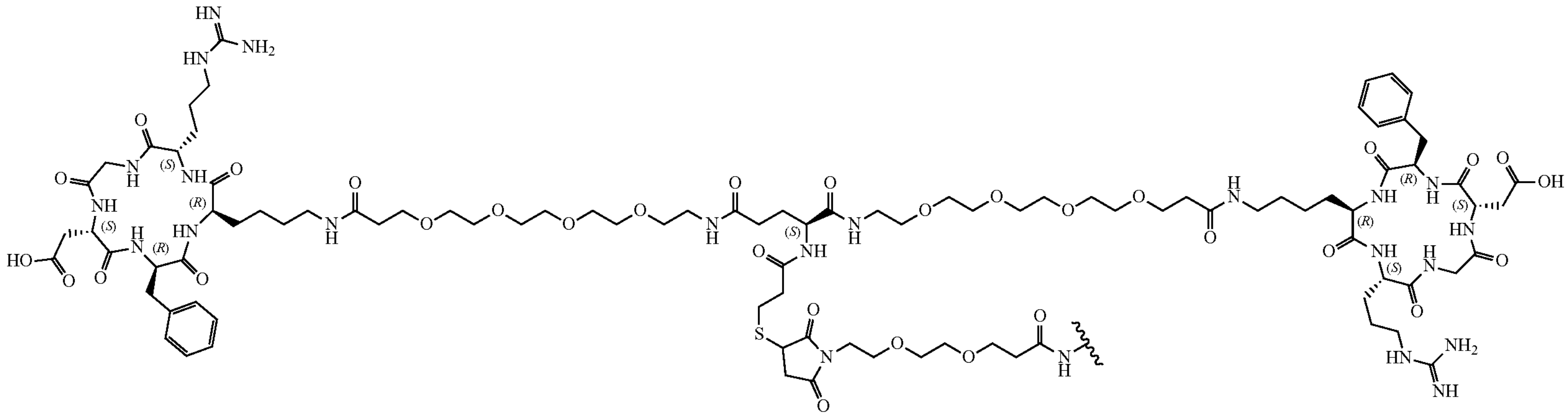 |
| R$_1$, R$_2$: | 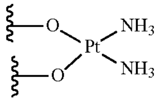 (A1) |

TABLE 1-continued
Structures of Examples
| Substituent | Example |
|---|---|
| Example: | |
| 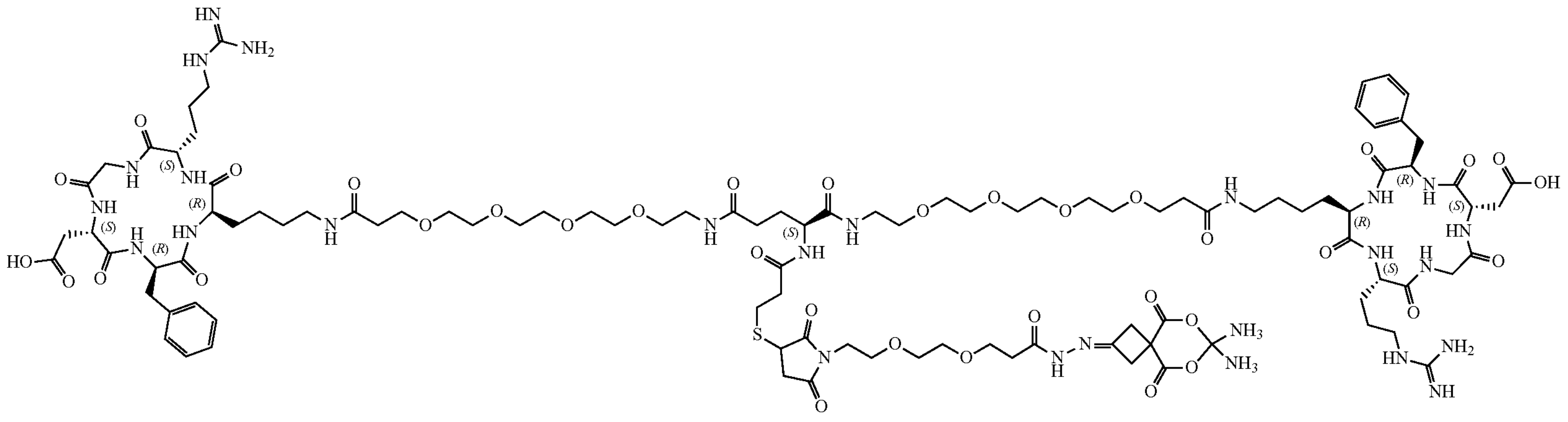 | S80 |
| R3: 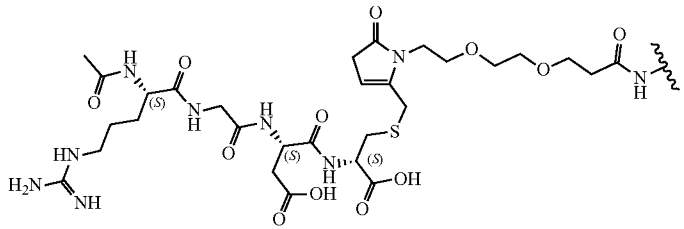 | 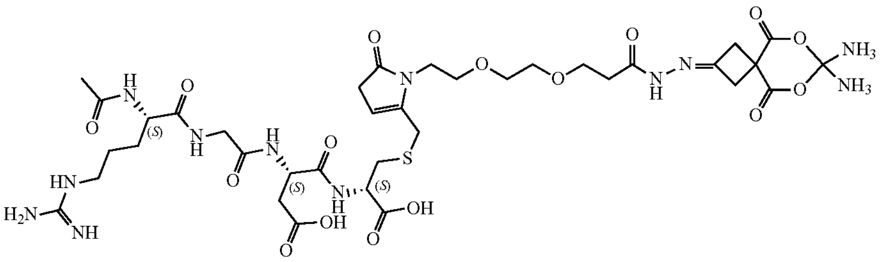 S81 |
| R1, R2: 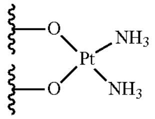 (A1) | |

TABLE 1-continued
| Structures of Examples | | |
|---|---|---|
| | Substituent | Example |
| $R_3$: | 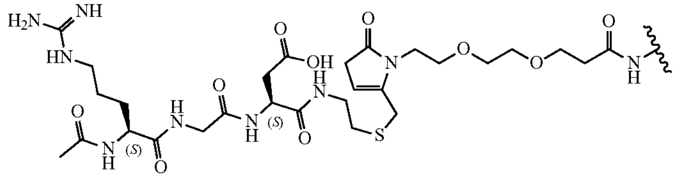 | 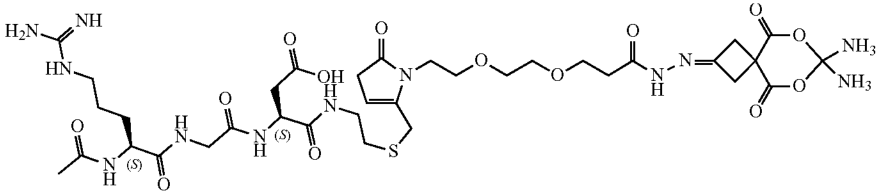<br>S82 |
| $R_1$, $R_2$: | 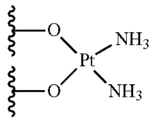<br>(A1) | |
| $R_3$: | 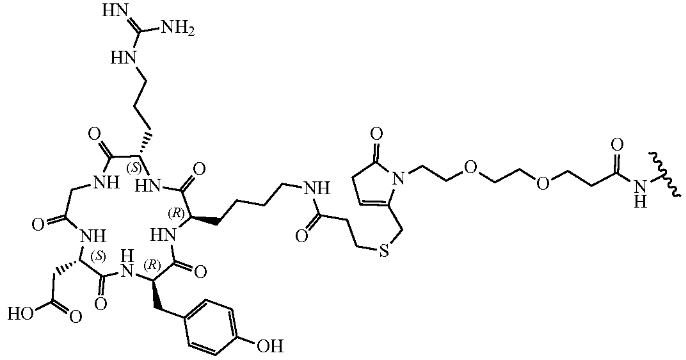 | 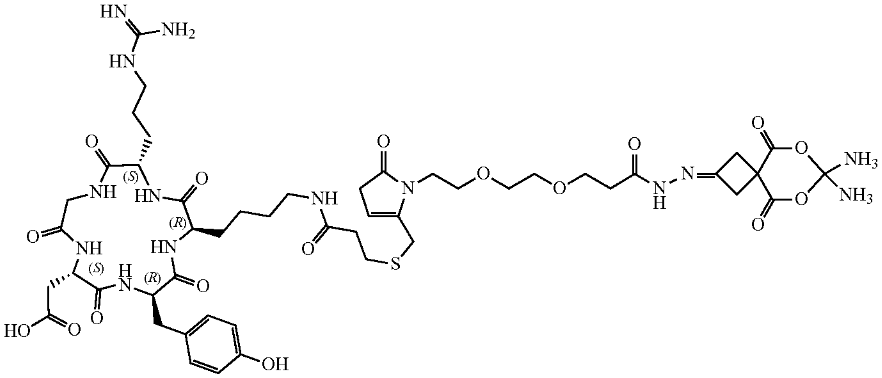<br>S83 |
| $R_1$, $R_2$: | 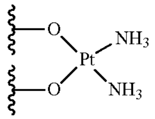<br>(A1) | |

TABLE 1-continued
| Structures of Examples | |
| --- | --- |
| Substituent | Example |
| $R_3$: | |
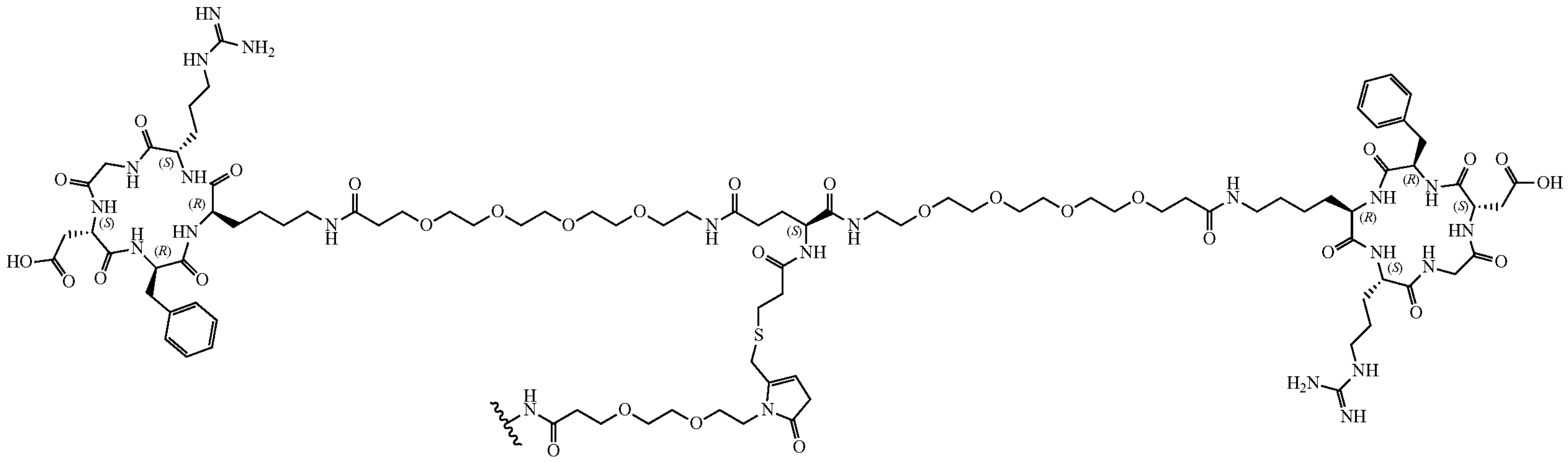
$R_1$, $R_2$:
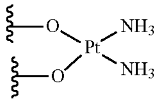
(A1)

TABLE 1-continued
| Structures of Examples | |
|---|---|
| Substituent | Example |
| | 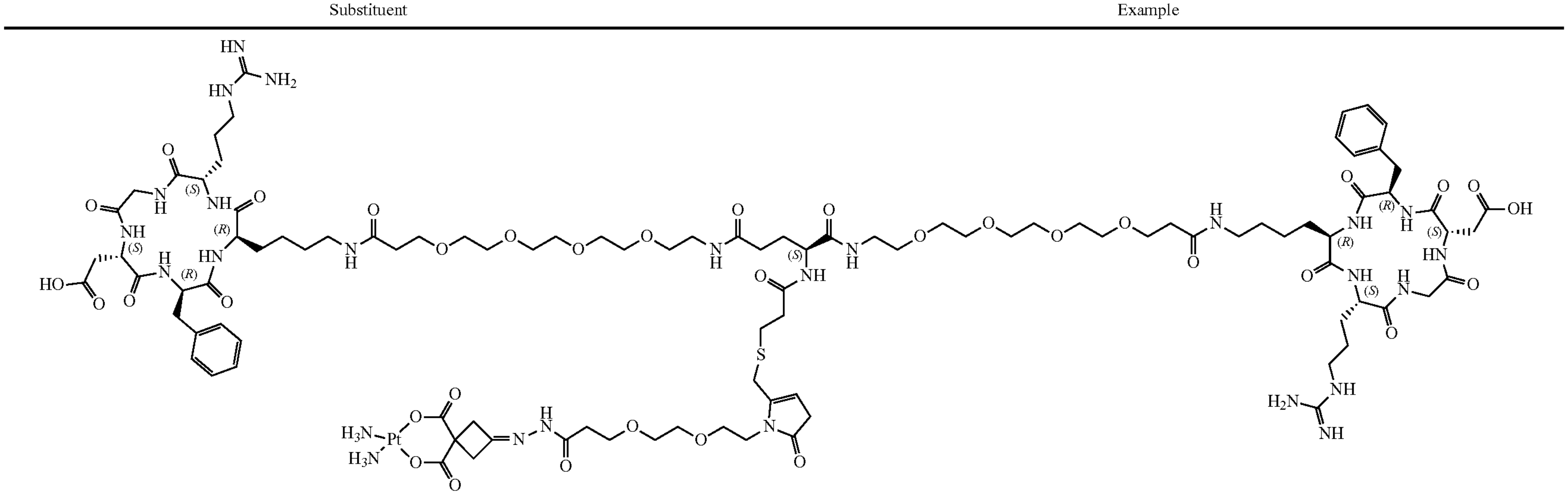<br>S84 |
| $R_3$: 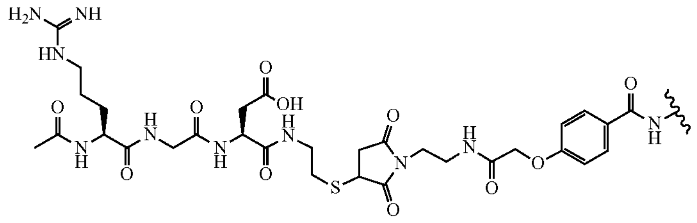 [SMILES: *NC(=O)c1ccc(OCC(=O)NCCN2C(=O)CC(SCCNC(=O)[C@H](CC(=O)O)NC(=O)CNC(=O)[C@H](CCCNC(=N)N)NC(C)=O)C2=O)cc1] | 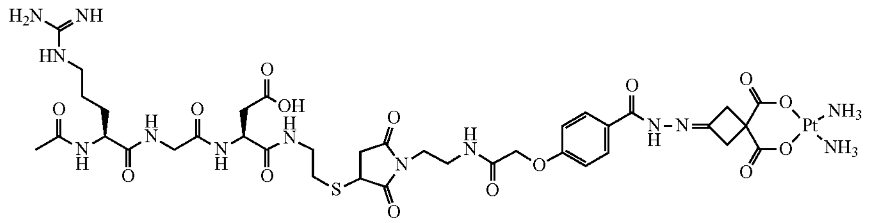<br>S85 |
| $R_1$, $R_2$: 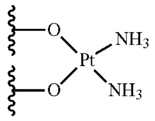<br>(A1) | |

TABLE 1-continued
| Structures of Examples | | |
|---|---|---|
| | Substituent | Example |
| $R_3$: | 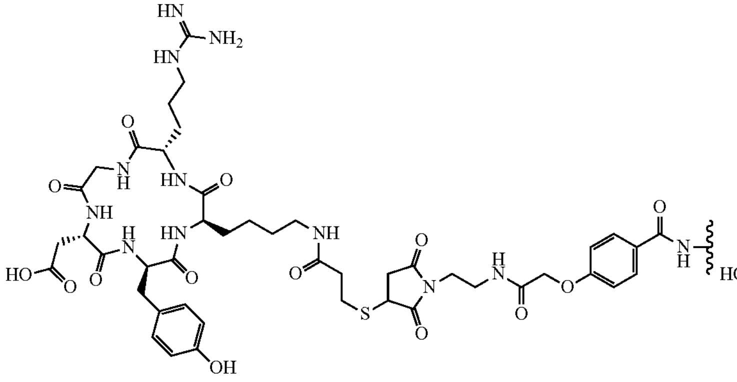 | 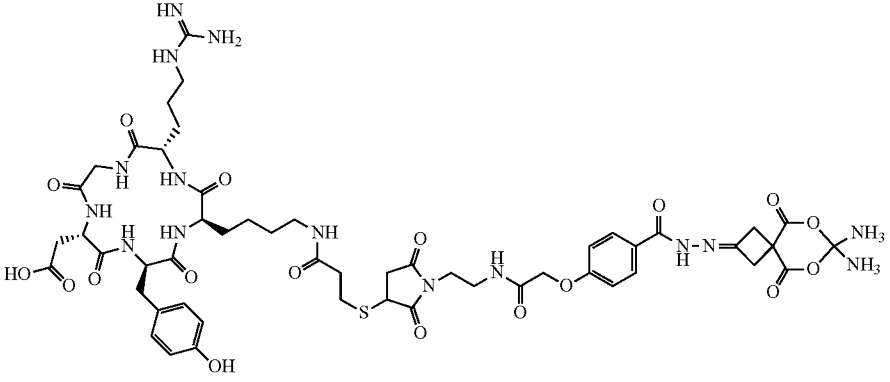<br>S86 |
| $R_1$, $R_2$: | 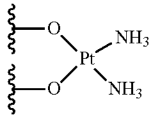<br>(A1) | |

TABLE 1-continued
| Structures of Examples | |
|---|---|
| Substituent | Example |
| $R_3$: | |
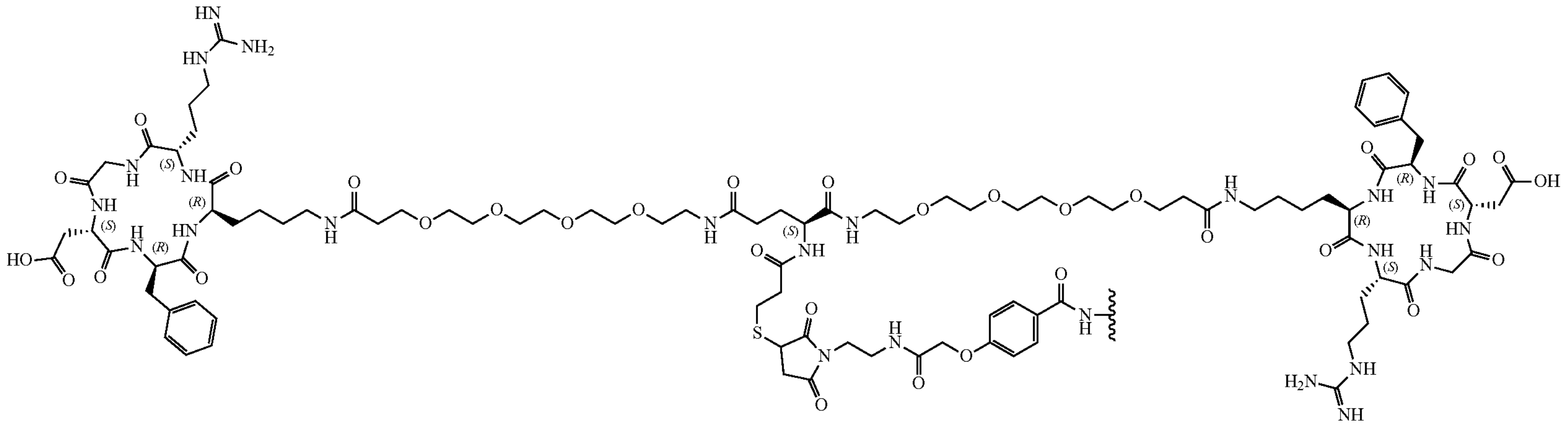
$R_1$, $R_2$:
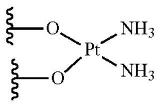
(A1)

TABLE 1-continued
Structures of Examples
| | Substituent | Example |
| --- | --- | --- |
| | 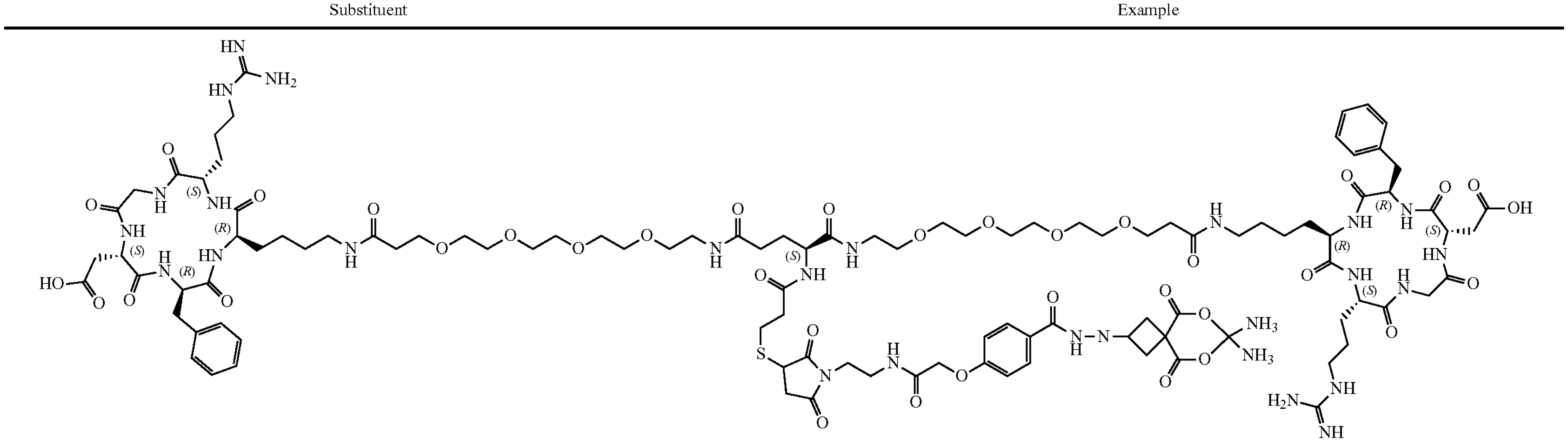 | S87 |
| R3: | 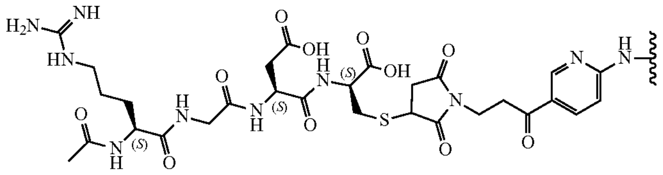 | 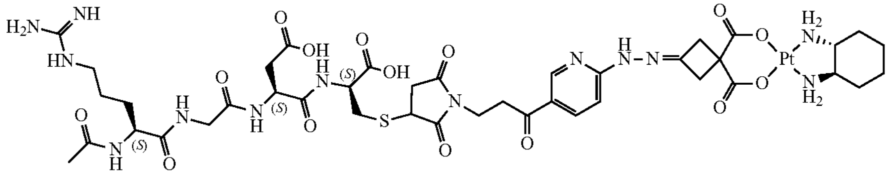 S88 |
| R1, R2: | 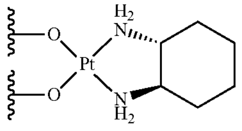 (A2) | |

TABLE 1-continued
| Structures of Examples | | |
|---|---|---|
| | Substituent | Example |
| $R_3$: | 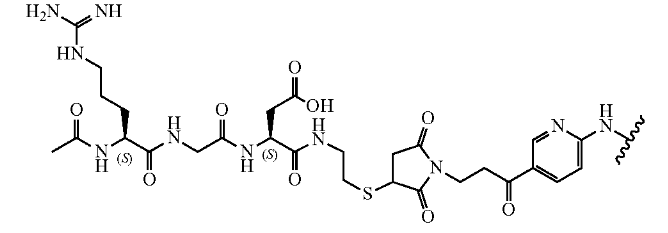 | 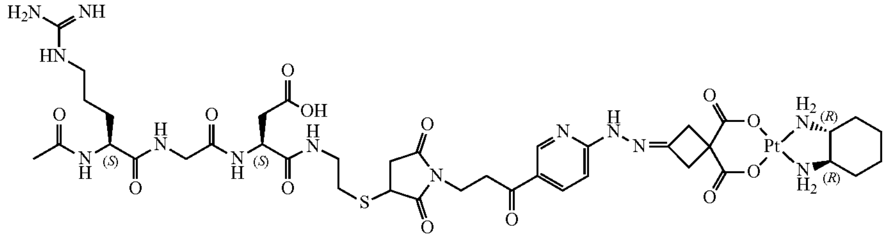 S89 |
| $R_1$, $R_2$: | 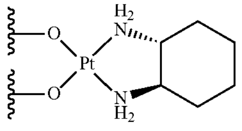 (A2) | |
| $R_3$: | 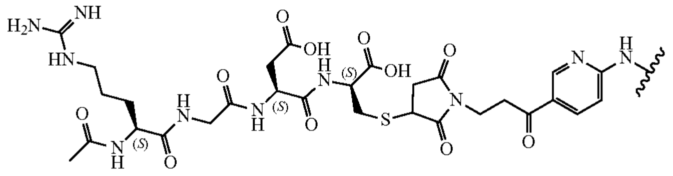 | 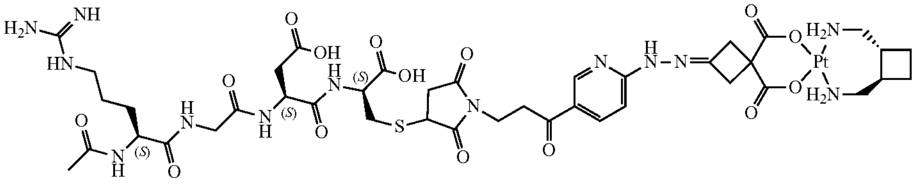 S90 |
| $R_1$, $R_2$: | 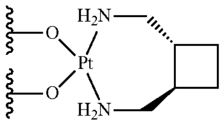 (A3) | |

TABLE 1-continued
| Structures of Examples | | |
|---|---|---|
| Substituent | | Example |
| $R_3$: | 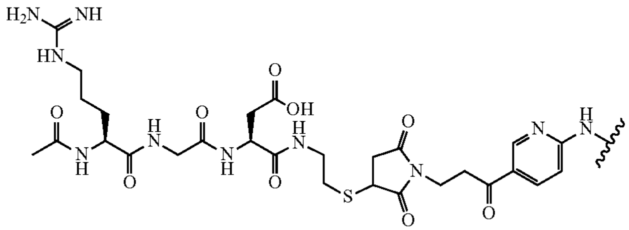 [SMILES: *Nc1ccc(C(=O)CCN2C(=O)CC(SCCNC(=O)[C@H](CC(=O)O)NC(=O)CNC(=O)[C@H](CCCNC(=N)N)NC(C)=O)C2=O)cn1] | 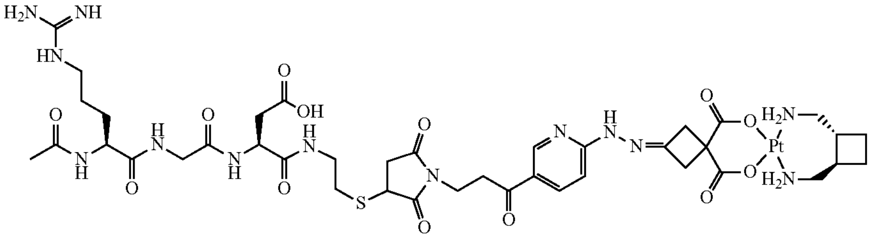 S91 |
| $R_1$, $R_2$: | 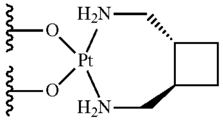 (A3) | |
| $R_3$: | 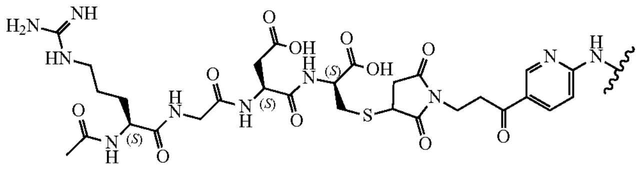 | 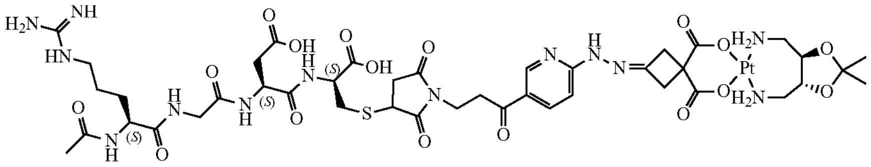 S92 |
| $R_1$, $R_2$: | 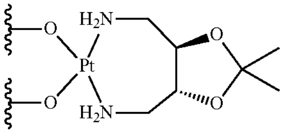 (A4) | |

TABLE 1-continued
| Structures of Examples | | |
|---|---|---|
| | Substituent | Example |
| $R_3$: | 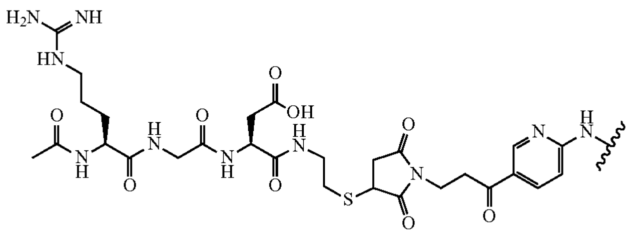 [SMILES: *Nc1ccc(C(=O)CCN2C(=O)CC(SCCNC(=O)[C@H](CC(=O)O)NC(=O)CNC(=O)[C@H](CCCNC(=N)N)NC(C)=O)C2=O)cn1] | 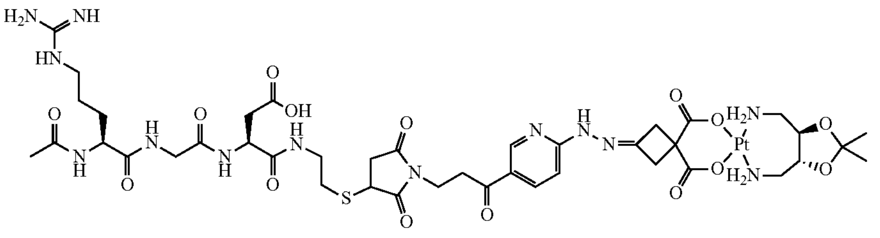<br>S93 |
| $R_1$, $R_2$: | 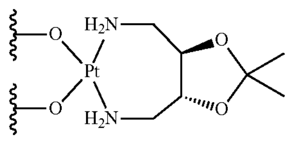<br>(A4) | |
| $R_3$: | 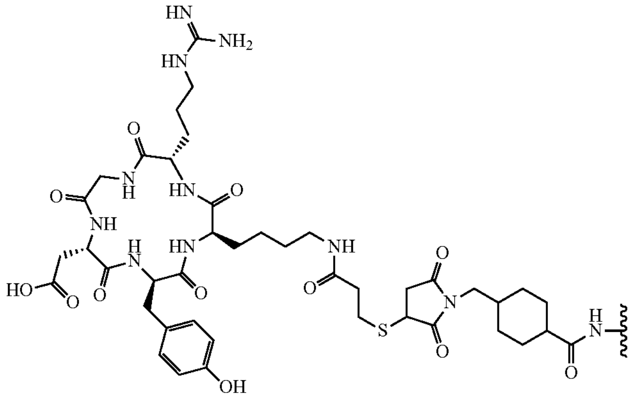 [SMILES: *NC(=O)C1CCC(CN2C(=O)CC(SCCC(=O)NCCCC[C@H]3NC(=O)[C@@H](Cc4ccc(O)cc4)NC(=O)[C@H](CC(=O)O)NC(=O)CNC(=O)[C@H](CCCNC(=N)N)NC3=O)C2=O)CC1] | 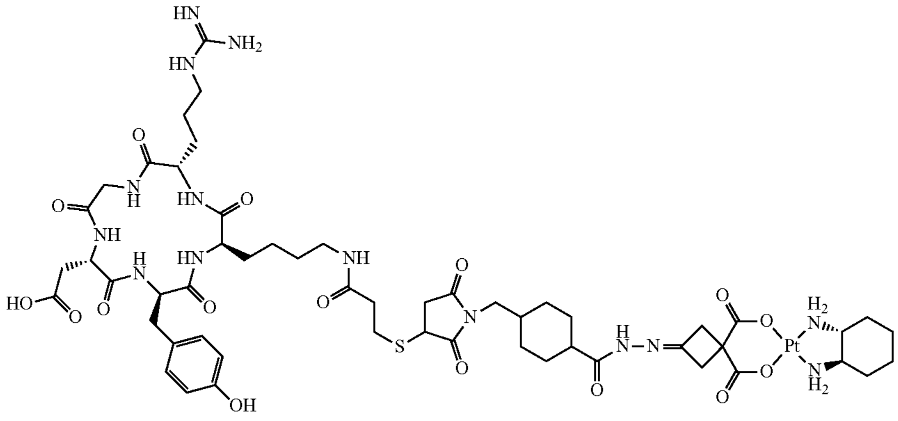<br>S94 |

TABLE 1-continued
Structures of Examples
| Substituent | Example |
| --- | --- |
| $R_1$, $R_2$: 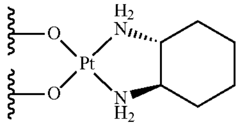 (A2) | |
| $R_3$: 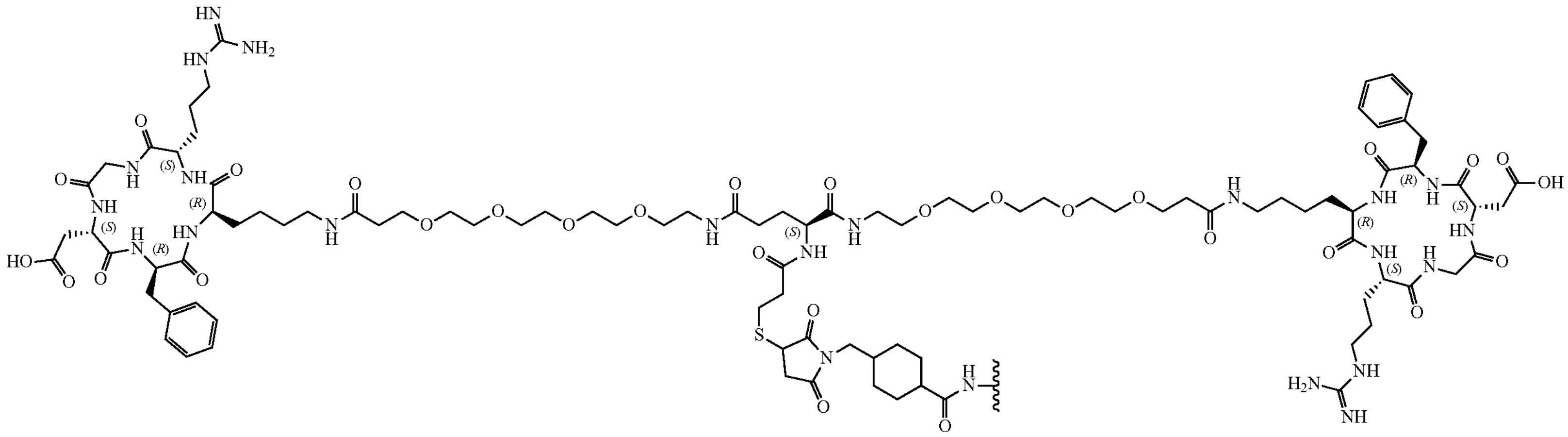 | |
| $R_1$, $R_2$: 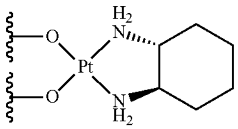 (A2) | |

TABLE 1-continued
| Structures of Examples | |
|---|---|
| Substituent | Example |
| Example: 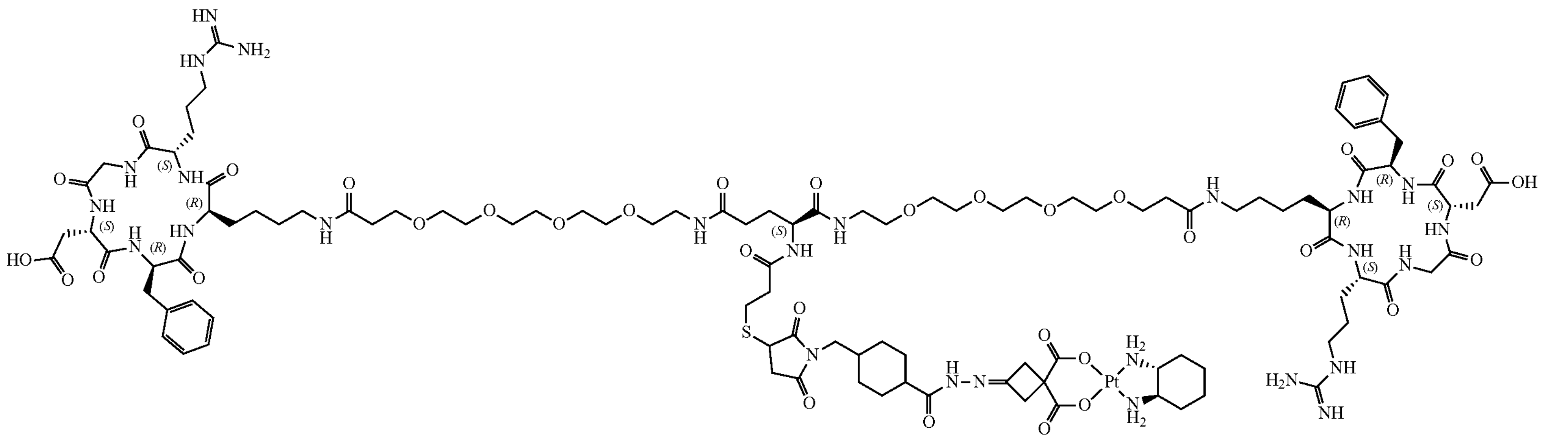 | S95 |
| R₃: 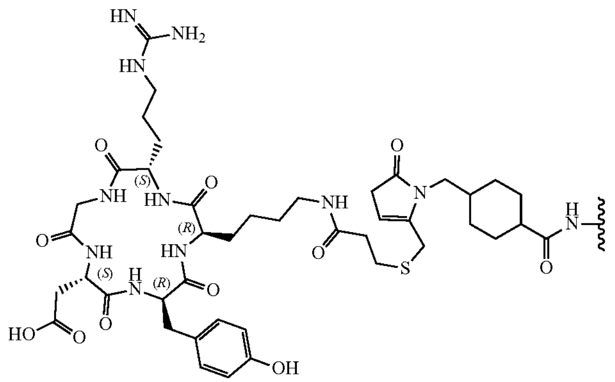 | 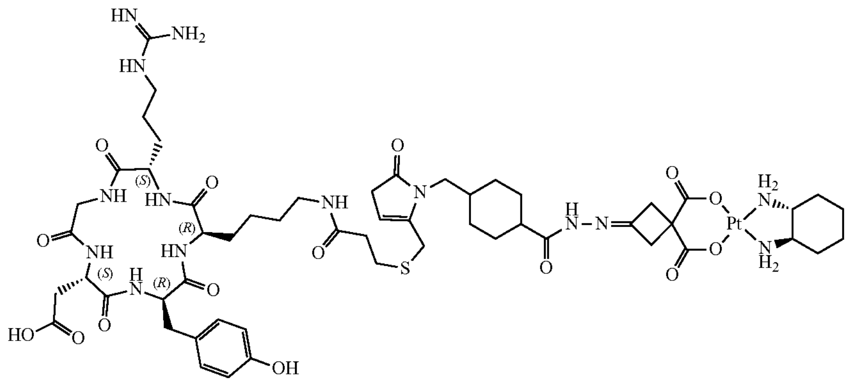 S96 |

TABLE 1-continued
| Structures of Examples | |
|---|---|
| Substituent | Example |
| R1, R2: 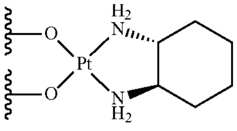 (A2) | |
| R3: 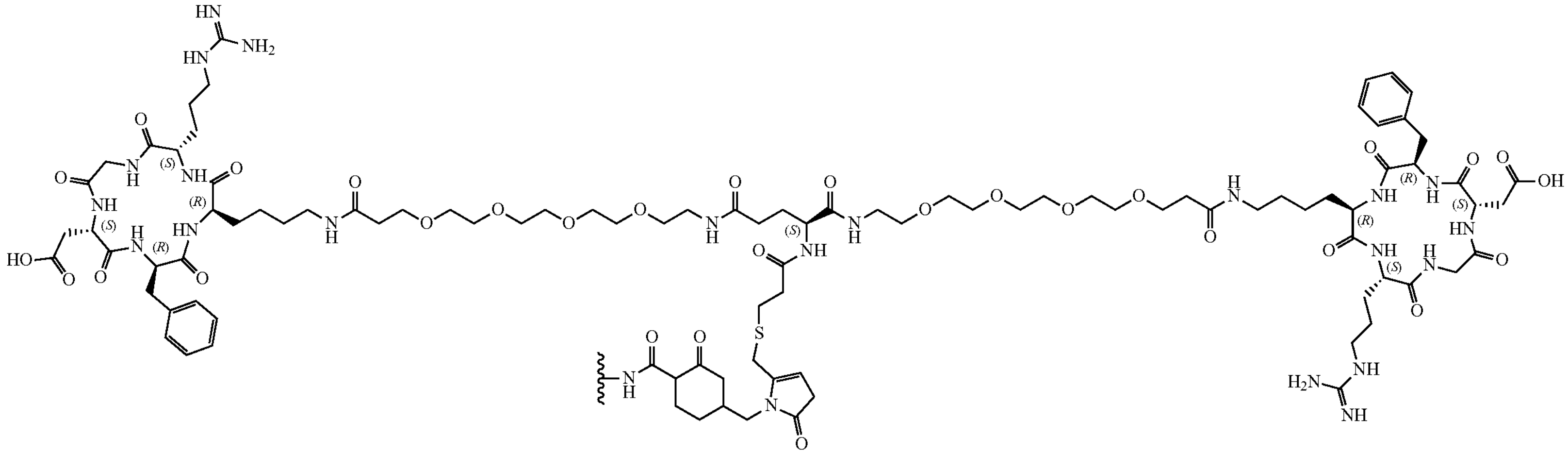 | |
| R1, R2: 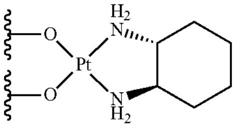 (A2) | |

TABLE 1-continued
| Structures of Examples | |
|---|---|
| Substituent | Example |
| Example: | |
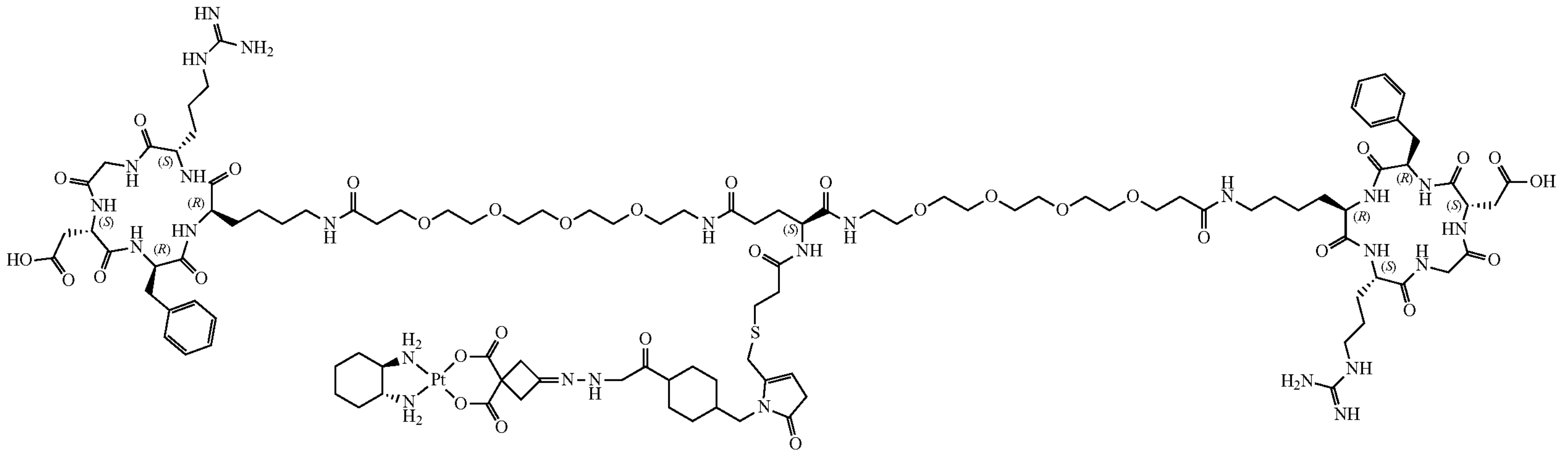
S97

The detection results of mass spectrometry (MS) confirmed that the molecular weights of compounds S1-S97 are sequentially shown in the following Table 2, which are consistent with the molecular weights predicted by structural calculation:

TABLE 2

Mass spectrometry detection results of examples

| Number | Mass spectrometry detection | Predicted molecular weight | Property | Yield |
|---|---|---|---|---|
| S1 | 581 | 580.42 | white solid | 195.2 mg |
| S2 | 579 | 578.45 | white solid | 185.3 mg |
| S3 | 699 | 697.61 | white solid | 164.8 mg |
| S4 | 697 | 695.64 | white solid | 221.1 mg |
| S5 | 693 | 691.58 | white solid | 236.2 mg |
| S6 | 691 | 689.61 | white solid | 160.5 mg |
| S7 | 635 | 634.48 | white solid | 175.3 mg |
| S8 | 634 | 632.51 | white solid | 198.7 mg |
| S9 | 629 | 627.48 | white solid | 178.2 mg |
| S10 | 627 | 625.51 | white solid | 154.1 mg |
| S11 | 623 | 621.51 | white solid | 198.0 mg |
| S12 | 621 | 619.54 | white solid | 162.8 mg |
| S13 | 639 | 637.58 | white solid | 140.4 mg |
| S14 | 637 | 635.60 | white solid | 187.3 mg |
| S15 | 567 | 566.39 | white solid | 194.2 mg |
| S16 | 565 | 564.42 | white solid | 146.7 mg |
| S17 | 593 | 592.47 | white solid | 137.2 mg |
| S18 | 592 | 590.50 | white solid | 172.3 mg |
| S19 | 640 | 638.50 | white solid | 154.3 mg |
| S20 | 638 | 636.53 | white solid | 169.5 mg |
| S21 | 593 | 592.47 | white solid | 148.4 mg |
| S22 | 711 | 709.58 | white solid | 128.3 mg |
| S23 | 593 | 592.47 | white solid | 136.2 mg |
| S24 | 713 | 711.60 | white solid | 154.0 mg |
| S25 | 620 | 618.51 | white solid | 167.3 mg |
| S26 | 618 | 616.54 | white solid | 174.2 mg |
| S27 | 591 | 590.46 | white solid | 129.4 mg |
| S28 | 589 | 588.48 | white solid | 137.3 mg |
| S29 | 701 | 699.54 | white solid | 168.4 mg |
| S30 | 785 | 783.70 | white solid | 174.2 mg |
| S31 | 662 | 660.55 | white solid | 146.5 mg |
| S32 | 660 | 658.58 | white solid | 150.8 mg |
| S33 | 662 | 660.55 | white solid | 114.7 mg |
| S34 | 660 | 658.58 | white solid | 154.2 mg |
| S35 | 708 | 706.57 | white solid | 163.9 mg |
| S36 | 706 | 704.60 | white solid | 118.5 mg |
| S37 | 716 | 714.61 | white solid | 132.6 mg |
| S38 | 716 | 714.60 | white solid | 147.6 mg |
| S39 | 714 | 712.64 | white solid | 170.2 mg |
| S40 | 760 | 758.67 | white solid | 182.4 mg |
| S41 | 709 | 707.61 | white solid | 106.3 mg |
| S42 | 707 | 705.64 | white solid | 114.7 mg |
| S43 | 709 | 707.61 | white solid | 119.1 mg |
| S44 | 707 | 705.64 | white solid | 150.6 mg |
| S45 | 755 | 753.63 | white solid | 164.2 mg |
| S46 | 753 | 751.66 | white solid | 108.2 mg |
| S47 | 791 | 789.71 | white solid | 115.6 mg |
| S48 | 789 | 787.73 | white solid | 120.3 mg |
| S49 | 791 | 789.71 | white solid | 184.2 mg |
| S50 | 790 | 787.73 | white solid | 175.6 mg |
| S51 | 837 | 835.73 | white solid | 114.3 mg |
| S52 | 835 | 833.76 | white solid | 120.4 mg |
| S53 | 700 | 698.64 | white solid | 126.5 mg |
| S54 | 698 | 696.67 | white solid | 156.3 mg |
| S55 | 700 | 698.64 | white solid | 165.8 mg |
| S56 | 698 | 696.67 | white solid | 117.3 mg |
| S57 | 746 | 744.67 | white solid | 120.6 mg |
| S58 | 744 | 742.69 | white solid | 124.0 mg |
| S59 | 672 | 670.59 | white solid | 148.6 mg |
| S60 | 670 | 668.61 | white solid | 152.3 mg |
| S61 | 672 | 670.59 | white solid | 119.3 mg |
| S62 | 670 | 668.61 | white solid | 114.6 mg |
| S63 | 718 | 716.61 | white solid | 132.6 mg |
| S64 | 716 | 714.64 | white solid | 124.1 mg |
| S65 | 1073 | 1071.94 | white solid | 118.3 mg |
| S66 | 1071 | 1069.97 | white solid | 128.6 mg |
| S67 | 1029 | 1027.93 | white solid | 147.3 mg |
| S68 | 1027 | 1025.96 | white solid | 136.2 mg |
| S69 | 1085 | 1083.99 | white solid | 127.6 mg |
| S70 | 1041 | 1039.98 | white solid | 135.6 mg |
| S71 | 1301 | 1300.28 | white solid | 128.4 mg |
| S72 | 2495 | 2493.64 | white solid | 140.2 mg |
| S73 | 1083 | 1082.02 | white solid | 117.4 mg |
| S74 | 1039 | 1038.01 | white solid | 121.0 mg |
| S75 | 1299 | 1298.30 | white solid | 123.6 mg |
| S76 | 2493 | 2491.67 | white solid | 130.5 mg |
| S77 | 1131 | 1130.02 | white solid | 140.0 mg |
| S78 | 1087 | 1086.01 | white solid | 134.2 mg |
| S79 | 1347 | 1346.30 | white solid | 198.9 mg |
| S80 | 2541 | 2539.67 | white solid | 186.4 mg |
| S81 | 1129 | 1128.05 | white solid | 102.3 mg |
| S82 | 1085 | 1084.04 | white solid | 89.6 mg |
| S83 | 1345 | 1344.33 | white solid | 78.5 mg |
| S84 | 2539 | 2537.69 | white solid | 94.3 mg |
| S85 | 1148 | 1147.05 | white solid | 84.6 mg |
| S86 | 1408 | 1407.05 | white solid | 91.7 mg |
| S87 | 2602 | 2600.71 | white solid | 74.9 mg |
| S88 | 1200 | 1199.13 | white solid | 69.8 mg |
| S89 | 1156 | 1155.12 | white solid | 79.4 mg |
| S90 | 1200 | 1199.13 | white solid | 88.4 mg |
| S91 | 1156 | 1155.12 | white solid | 76.9 mg |
| S92 | 1246 | 1245.15 | white solid | 124.1 mg |
| S93 | 1202 | 1201.14 | white solid | 108.4 mg |
| S94 | 1407 | 1406.44 | white solid | 154.6 mg |
| S95 | 2601 | 2599.81 | white solid | 134.2 mg |
| S96 | 1405 | 1404.47 | white solid | 112.7 mg |
| S97 | 2599 | 2597.84 | white solid | 143.7 mg |

In Vitro Water Solubility Experiment of Example

In order to compare the difference in water solubility between the platinum compounds of the present disclosure and the marketed drugs cisplatin, carboplatin and oxaliplatin, the water solubility at room temperature was determined. At room temperature of 25° C., the test sample that had been ground into a fine powder was weighed accurately, and shaken vigorously for 30 seconds every 5 minutes in a certain volume of distilled water; and the dissolution of each test sample was observed within 30 minutes. If no visible solute particles were visible, the sample was considered to be completely dissolved. The experimental results of the solubility of the test sample in water are shown in Table 3.

TABLE 3
| Solubility of the test sample in water | | |
|---|---|---|
| Platinum compound | Structure | Solubility (mg/mL) |
| Cisplatin | 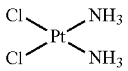 | 1.0 |
| Carboplatin | 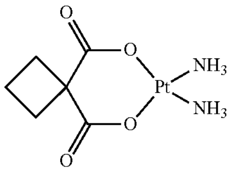 | 16.6 |
| Oxaliplatin | 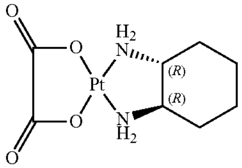 | 5.5 |
| S47 | 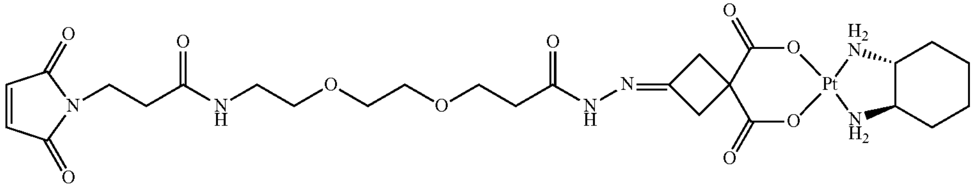 S47 | >20 |

TABLE 3-continued
| Solubility of the test sample in water | | |
|---|---|---|
| Platinum compound | Structure | Solubility (mg/mL) |
| S72 | 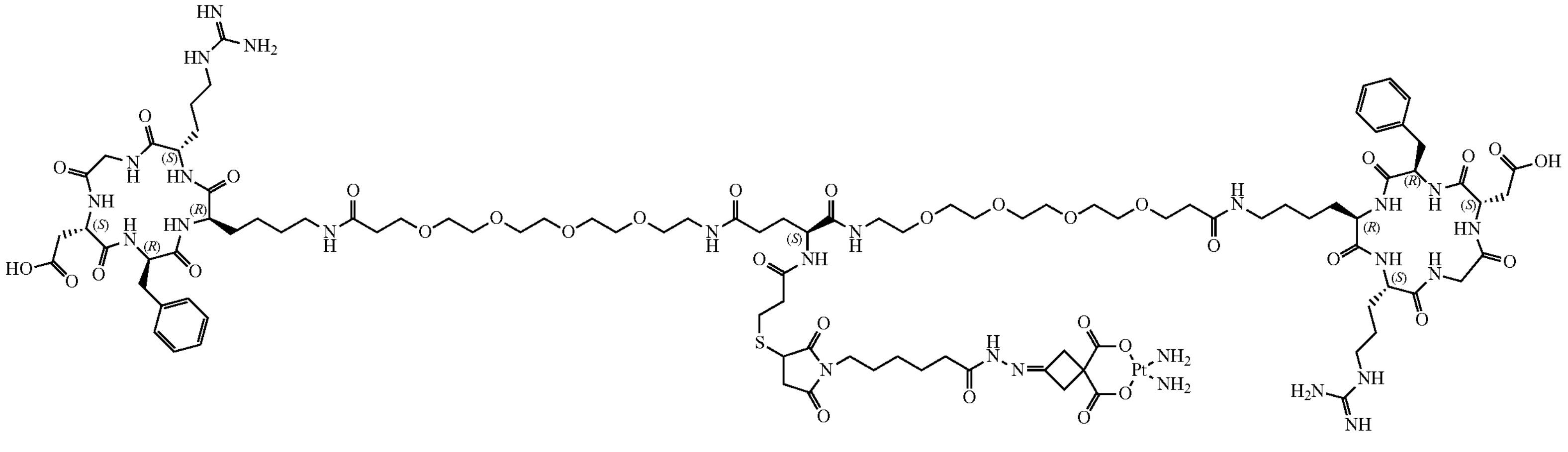 S72 | >30 |

TABLE 3-continued
| Solubility of the test sample in water | | |
|---|---|---|
| Platinum compound | Structure | Solubility (mg/mL) |
| S80 | 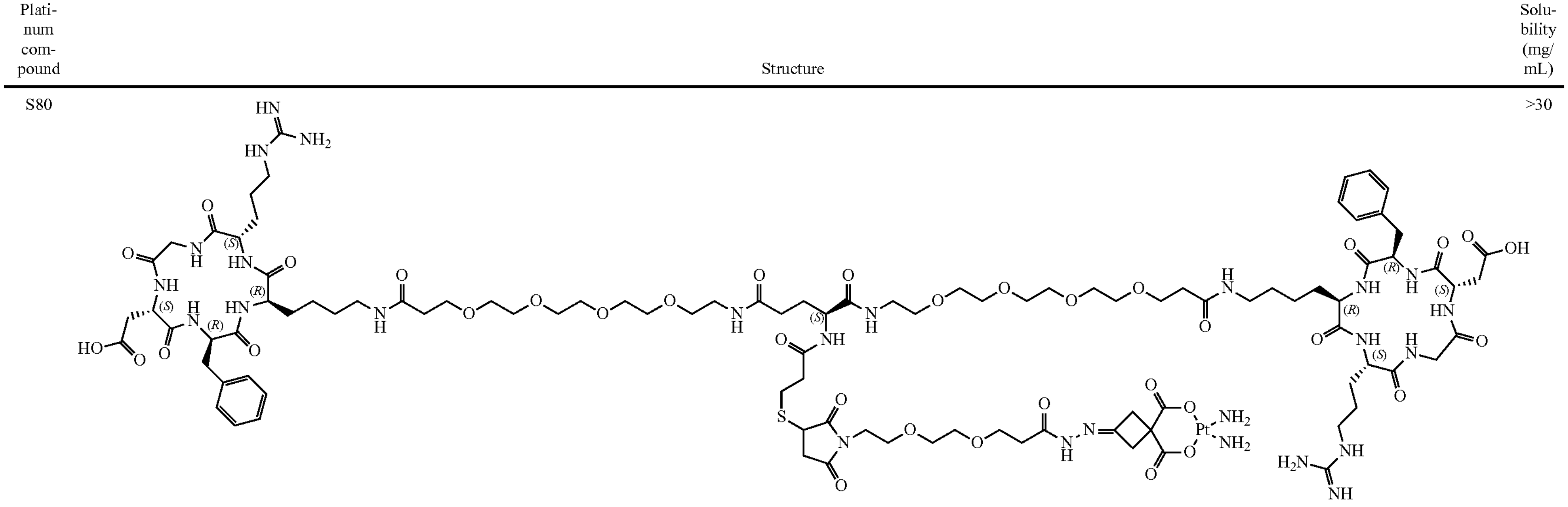 S80 | >30 |

TABLE 3-continued
| Solubility of the test sample in water | | |
|---|---|---|
| Platinum compound | Structure | Solubility (mg/mL) |
| S95 | 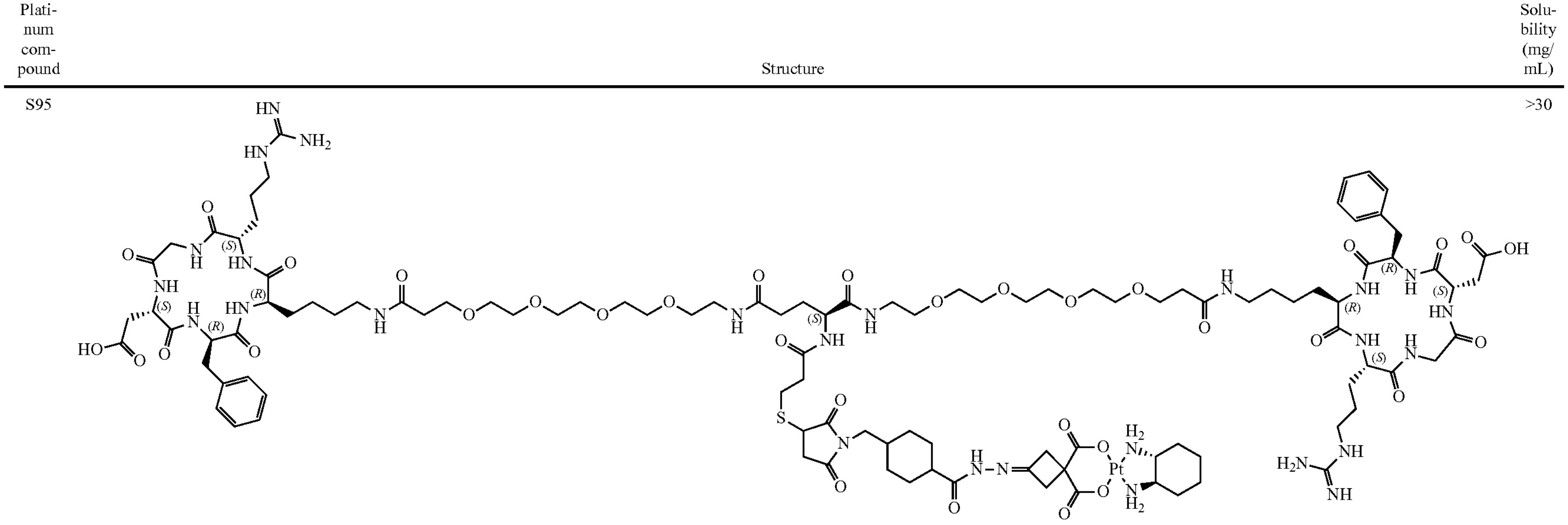 S95 | >30 |

TABLE 3-continued
| Solubility of the test sample in water | | |
|---|---|---|
| Platinum compound | Structure | Solubility (mg/mL) |
| S97 | 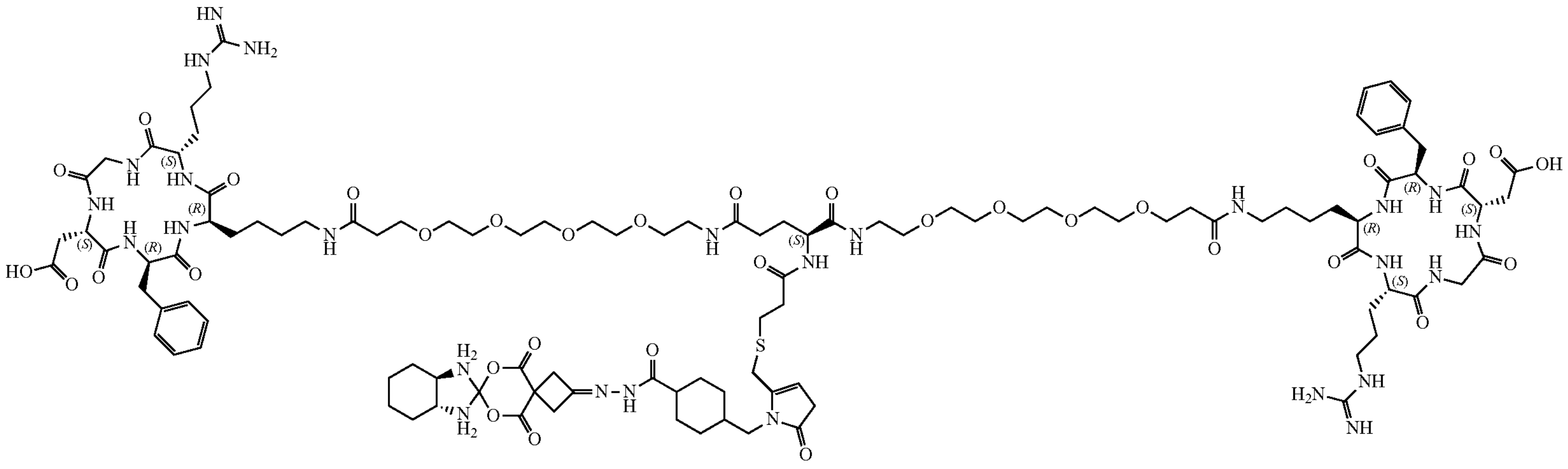 S97 | 30 |

Conclusions: The water solubility of marketed drugs cisplatin and oxaliplatin is poor, both of which are less than 6 mg/mL. The solubility of carboplatin is slightly better, reaching 16.6 mg/mL in water. However, the water solubility of the examples S47, S72, S80, S95 and S97S disclosed by the present disclosure are significantly improved compared with the marketed drugs. Especially the water solubility of example 72 and example S80, compared with carboplatin, the water solubility has nearly a 1-fold improvement; the water solubility of example S47, example S95, example S97 has an improvement of 3 times or more, and examples S47, S72, S80, S95 and S97S are easier to make into a lyophilized powder or an aqueous solution dosage form, which solves the adverse effects of poor water solubility of platinum drugs in clinical application.

In Vivo Tumor Inhibition Experiment of Example

The inhibitory effects of example S47 and example S70 of the present disclosure on animal transplanted tumor S180 were tested.

Kunming mice, ♀, 22±1 g, were purchased from Shanghai Slac Laboratory Animal Co., Ltd. Certificate number: SCXK (Shanghai) 2013-0010-02. Feeding environment: SPF level. Example S47, example S70 and carboplatin, a positive control drug, were prepared with 5% glucose to the required concentration. Mice were subcutaneously inoculated with S180 sarcoma cells, and the drug administration was started on the next day of inoculation. The administration dose and scheme are shown in Table 4. The mice were killed on the eighth day, and the tumor was weighed and the tumor inhibition rate was calculated.

Tumor inhibition rate=(tumor weight in the control group−tumor weight in the treatment group)/tumor weight in the control group×100

TABLE 4

Therapeutic effects of example S47, example S70 and carboplatin in S180 sarcoma of mice

| Group | Dose mmol/kg | Route of administration | Number of mice: Before administration | Number of mice: After administration | Tumor weight (g) X ± SD | Tumor inhibition rate % |
|---|---|---|---|---|---|---|
| Control group | NS | Ip, dl, 4 | 10 | 10 | 1.92 ± 0.33 | |
| S47-Low dose | 80 | Ip, dl, 4 | 6 | 6 | 0.87 ± 0.18 | 54.7 |
| S47-Medium dose | 160 | Ip, dl, 4 | 6 | 6 | 0.53 ± 0.21 | 72.4 |
| S47-High dose | 240 | Ip, dl, 4 | 6 | 6 | 0.26 ± 0.12 | 86.5 |
| S70-Low dose | 80 | Ip, dl, 4 | 6 | 6 | 0.92 ± 0.20 | 52.3 |
| S70-Medium dose | 160 | Ip, dl, 4 | 6 | 6 | 0.56 ± 0.17 | 70.8 |
| S70-High dose | 240 | Ip, dl, 4 | 6 | 6 | 0.30 ± 0.14 | 84.6 |
| Carboplatin | 160 | Ip, dl, 4 | 6 | 6 | 0.78 ± 0.28 | 60.4 |

*P<0.01 compared with the control group

Conclusion: Example S47 and example S70 have obvious inhibitory effects on the growth in S180 sarcoma of mice, and the inhibitory effects at equimolar concentrations are significantly better than carboplatin, an anticancer drug widely used in clinical practice, and example S47 and example S70 have a good dose-effect relationship, and have a good clinical application prospect.

The invention claimed is:

1. A compound represented by the following formula (I) or a pharmaceutically acceptable salt thereof, (I)

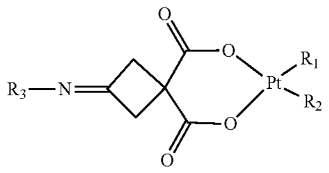

wherein:

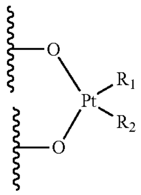

is the following structure:

(A1)

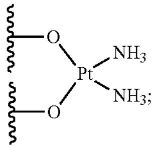

-continued (A2)

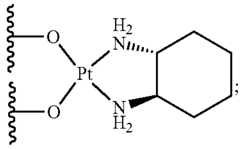

-continued (A3)

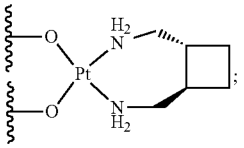

(A4)

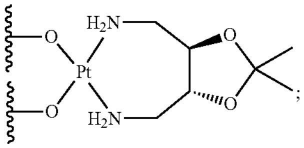

(A5)

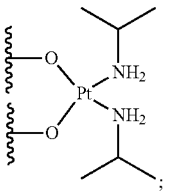

(A6)

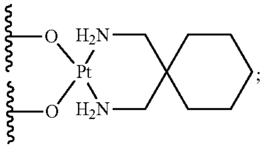

(A7)

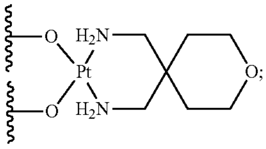

or (A8)

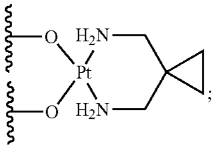

$R_3$ is the following structure:

R3-1

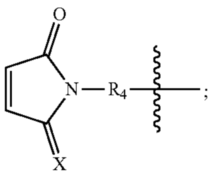

R3-2

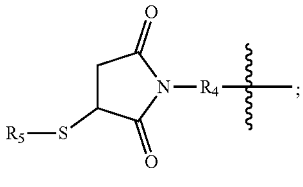

or

-continued

R3-3

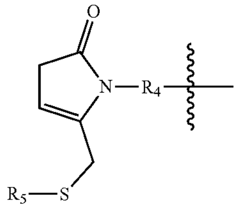

wherein, X is $CH_2$or O;

$R_4$ is selected from:

R4-12

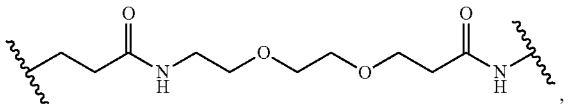

R4-8

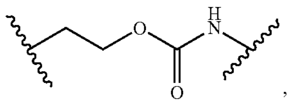

R4-10

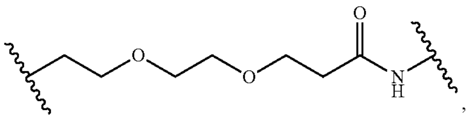

R4-15

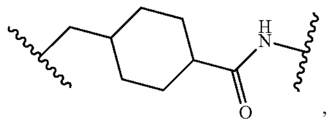

R4-16

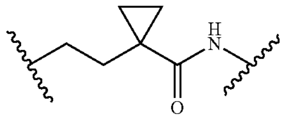

and $C_{1-12}$ alkylcarbonylamino;

$R_5$ is: human serum albumin HSA; an antibody that binds to a tumor-associated antigen; or, a molecule that is able to specifically bind to a tumor cell surface integrin receptor.

2. The compound represented by formula (I) or the pharmaceutically acceptable salt thereof as claimed in claim 1, wherein, the general formula of this series of platinum compounds is:

I-A1

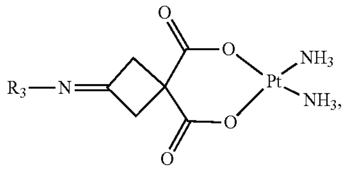

-continued

I-A2

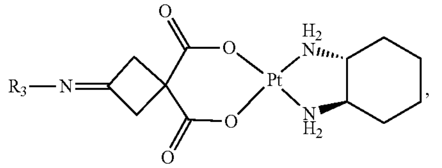

I-A3

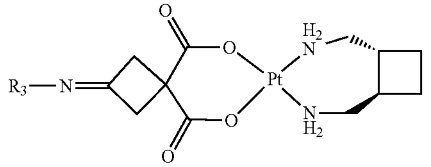

or

I-A4

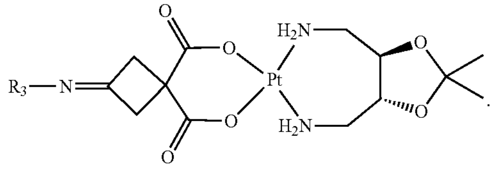

3. The compound represented by formula (I) or the pharmaceutically acceptable salt thereof as claimed in claim 1, wherein, $R_4$ is the following structure:

R4-9

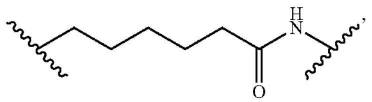

R4-11

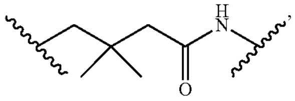

R4-13

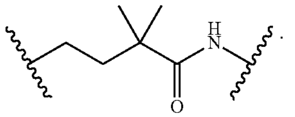

4. The compound represented by formula (I) or the pharmaceutically acceptable salt thereof as claimed in claim 1, wherein, $R_5$ is the molecule that is able to specifically bind to the tumor cell surface integrin receptor.

5. The compound represented by formula (I) or the pharmaceutically acceptable salt thereof as claimed in claim 4, wherein, $R_5$ is the molecule that is able to specifically bind to an integrin, and comprises an arginine-glycine-aspartic acid (RGD) tripeptide sequence in chemical structure.

6. The compound represented by formula (I) or the pharmaceutically acceptable salt thereof as claimed in claim 1, wherein, the general structure formula is shown in any one of the following structures:

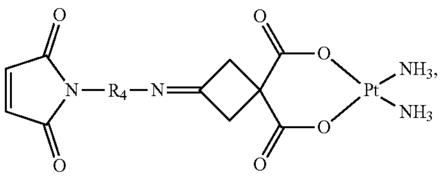

-continued

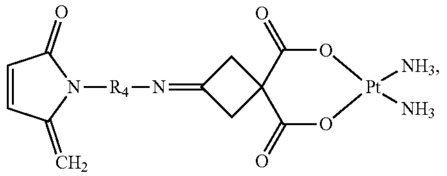

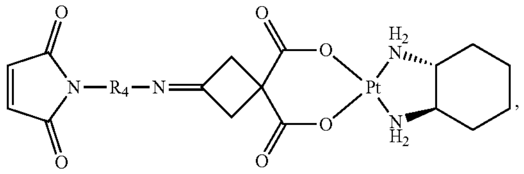

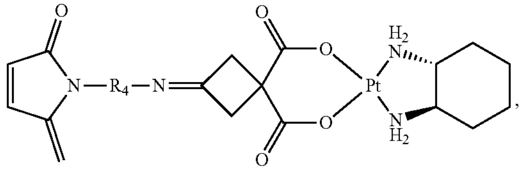

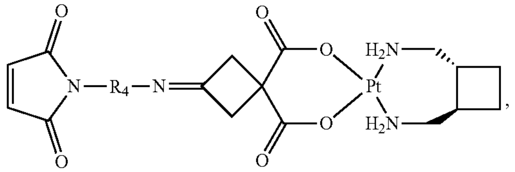

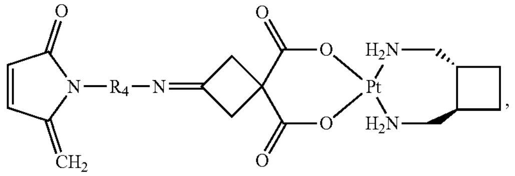

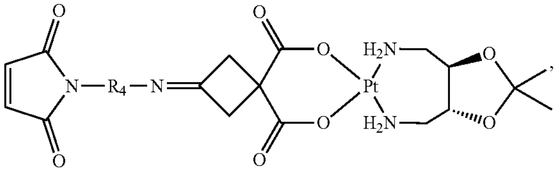

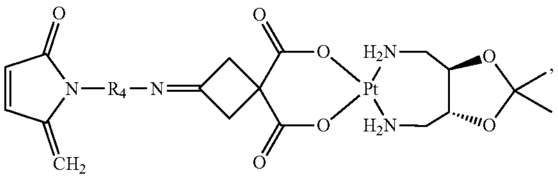

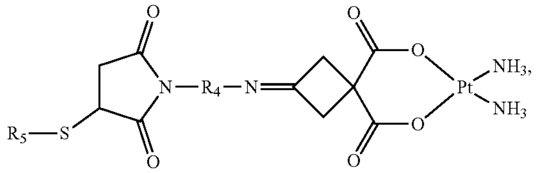

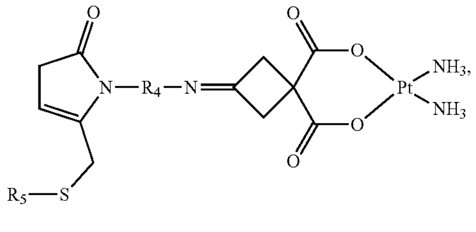

-continued
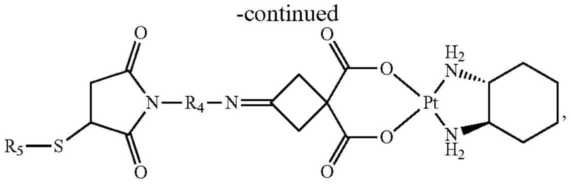
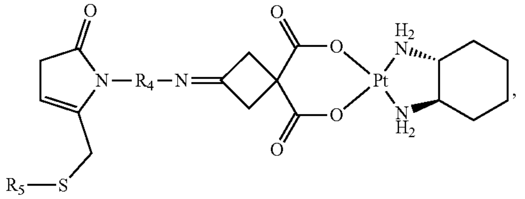
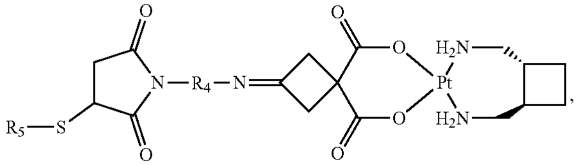
-continued
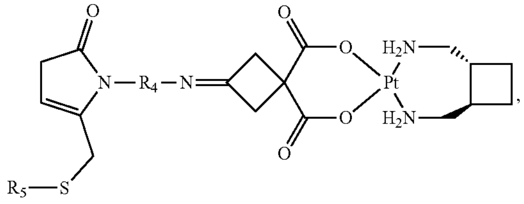
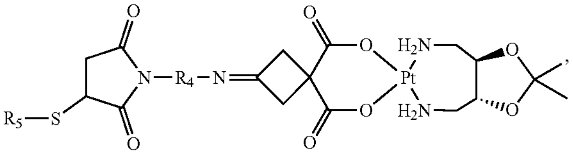
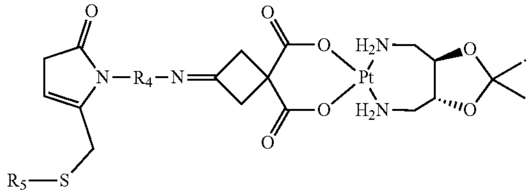
7. The compound represented by formula (I) or the pharmaceutically acceptable salt thereof as claimed in claim 1, wherein, the compound represented by formula (I) is:
S15
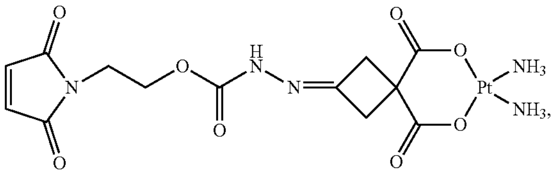
S16
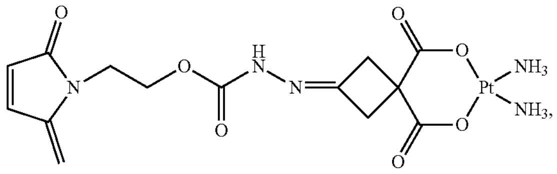
S18
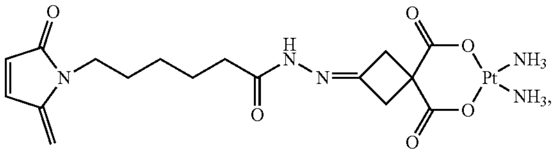
S19
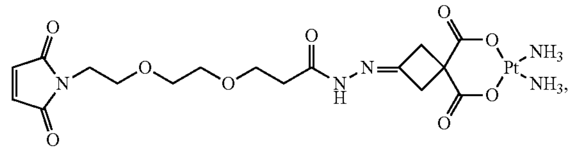
S20
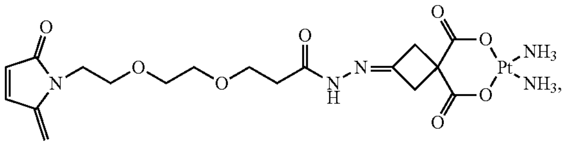
S21
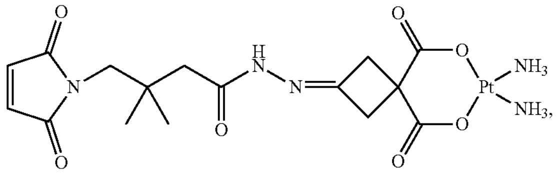
S22
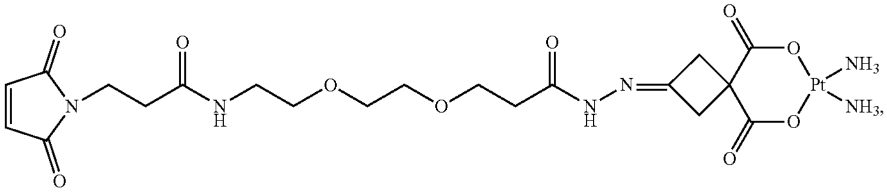

-continued
S23
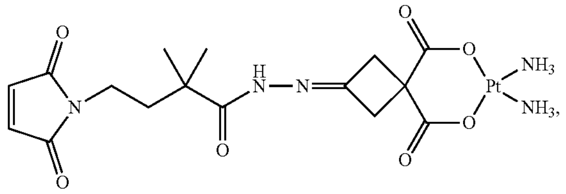
S25
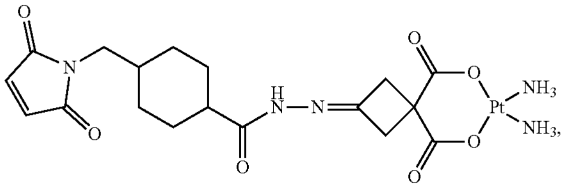
S26
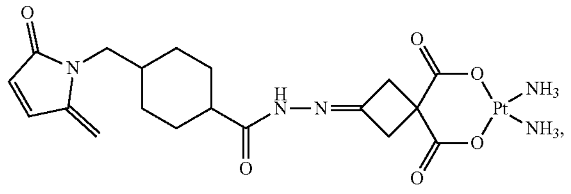
S27
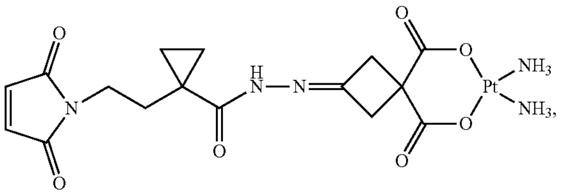
S28
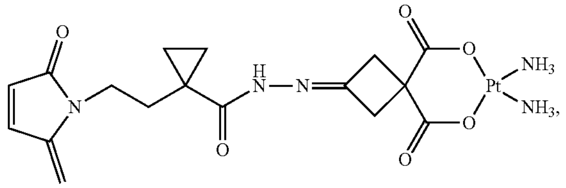
S48
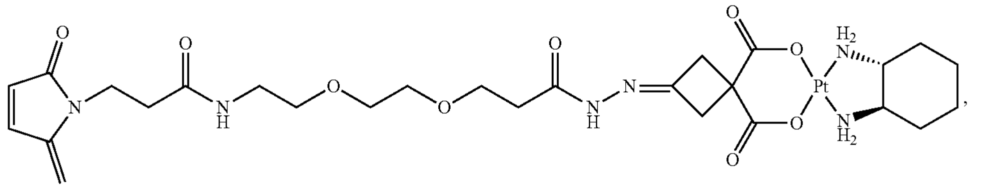
S49
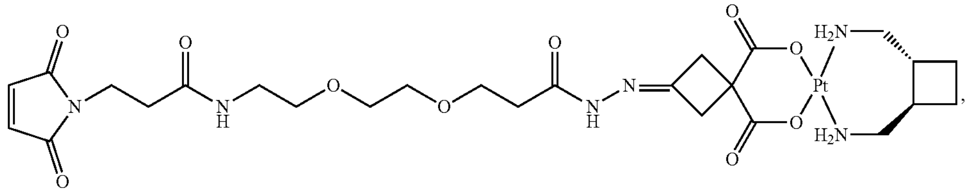
S50
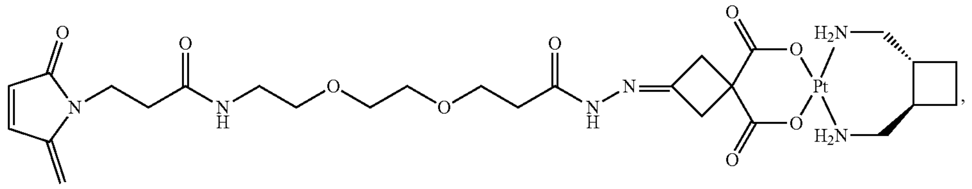
S51
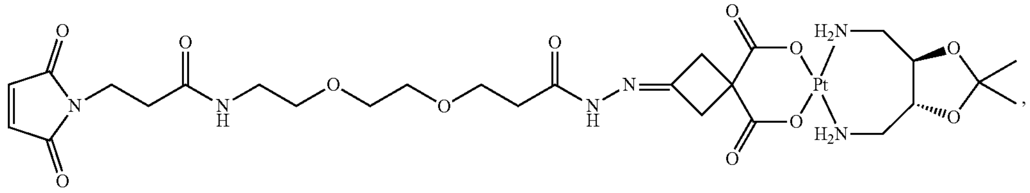
S52
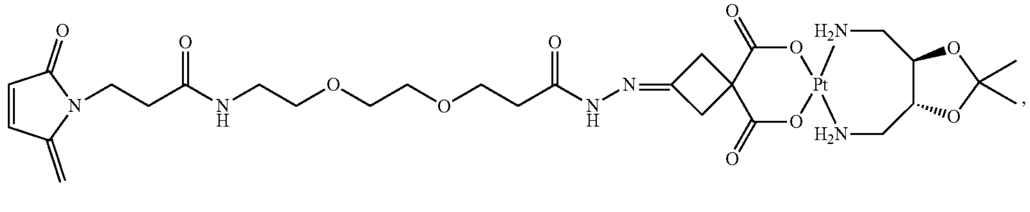

-continued
S53
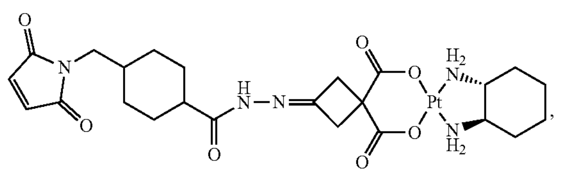
S54
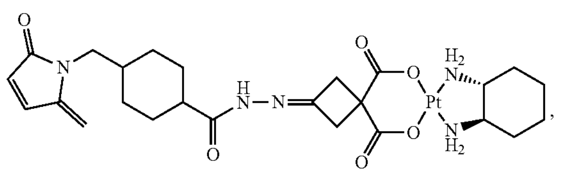
S55
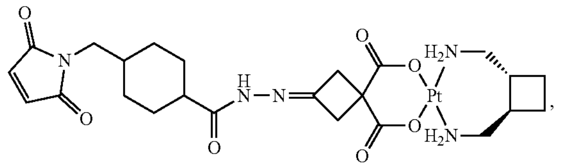
S56
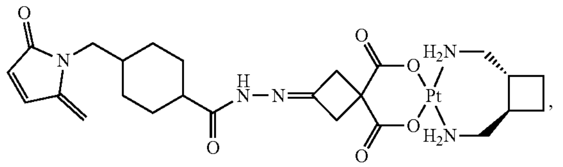
S57
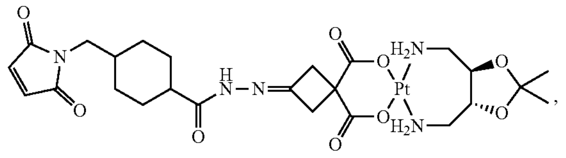
S58
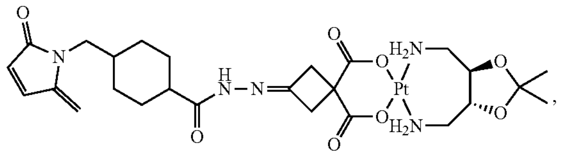
S59
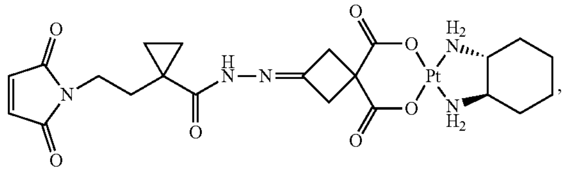
S60
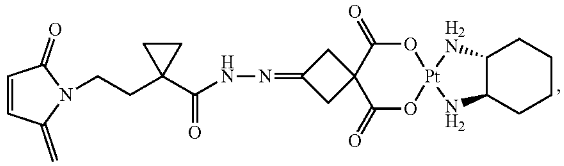
S61
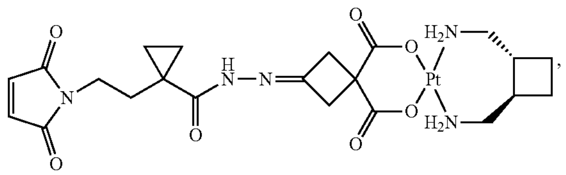
S62
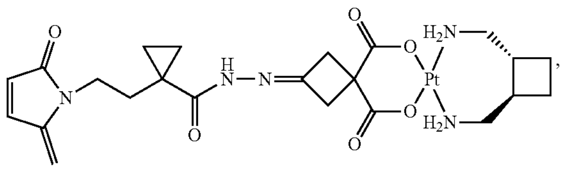
S63
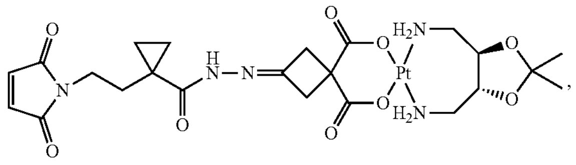
S64
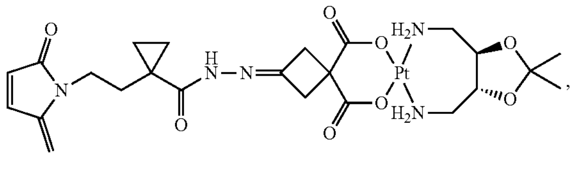
S69
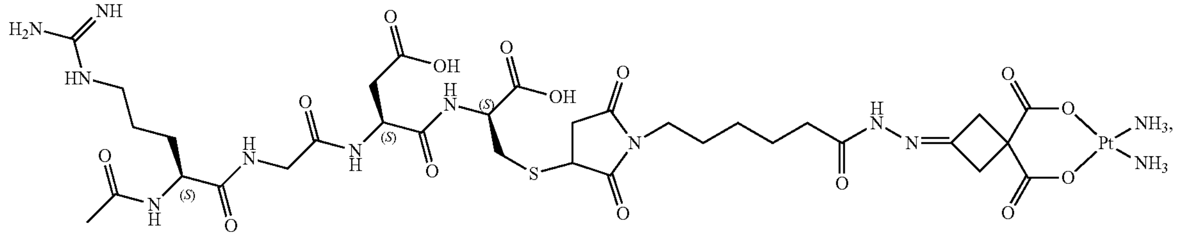

-continued
S70
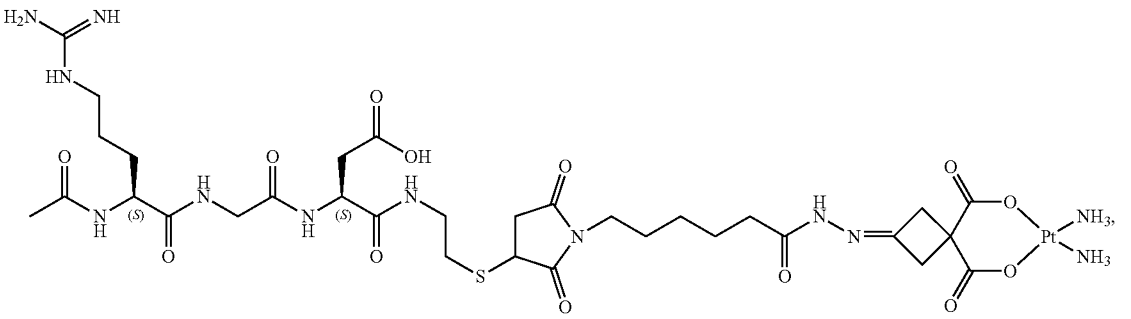
S71
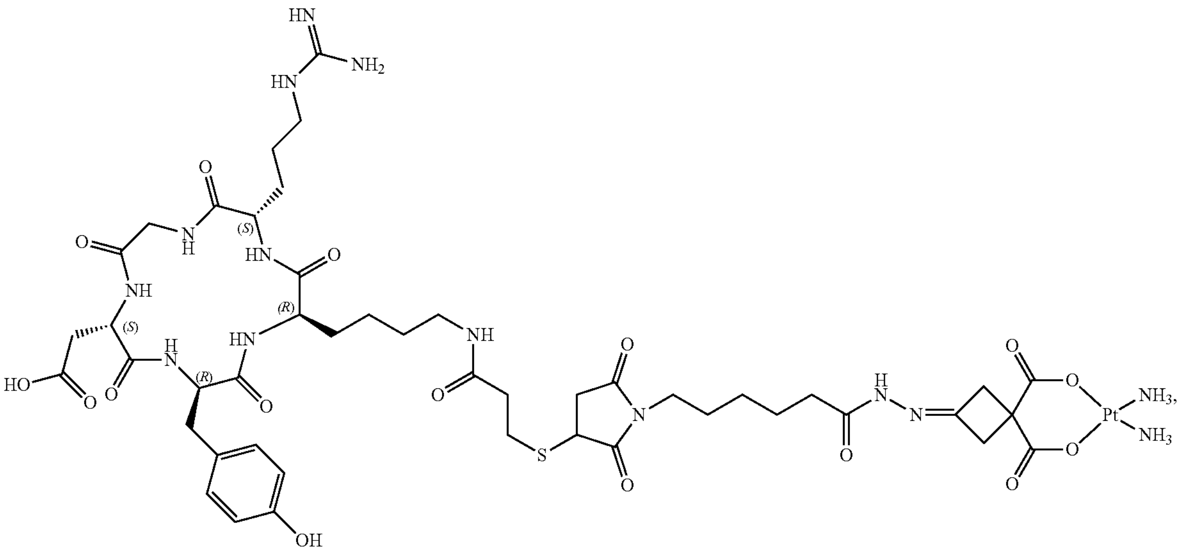
S73
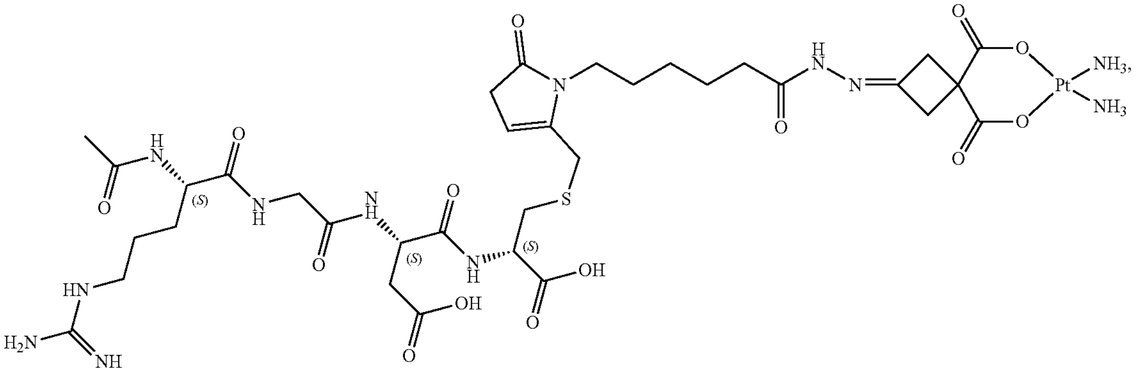
S74
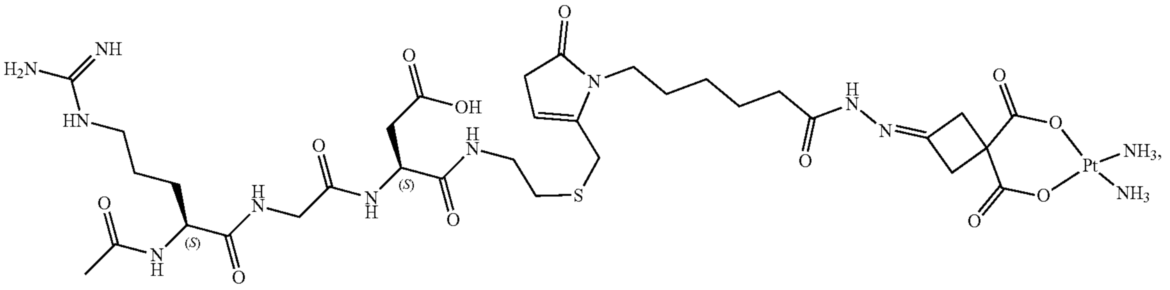

-continued
S75
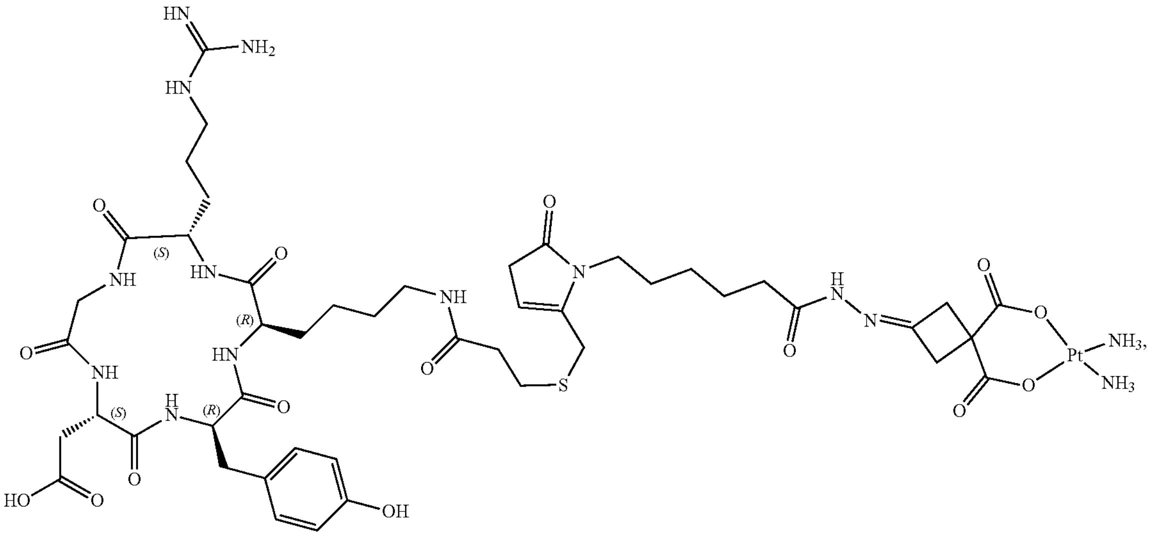
S76
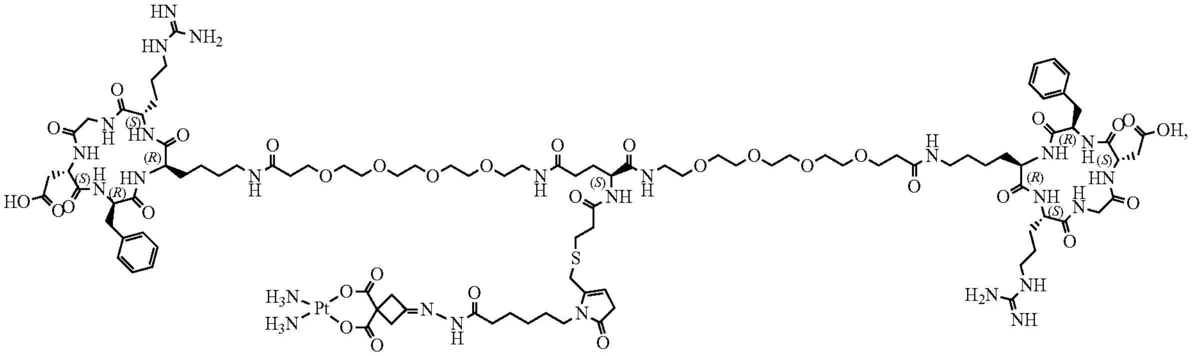
S77
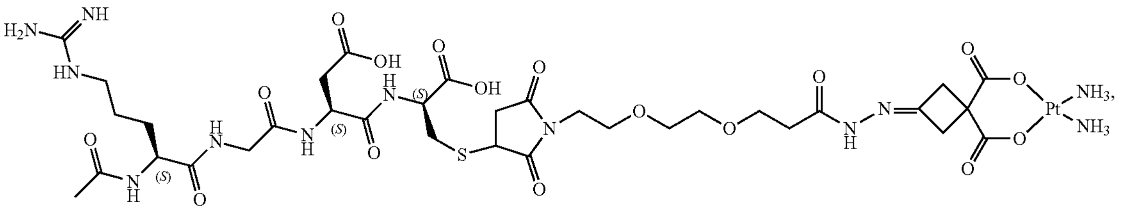
S78
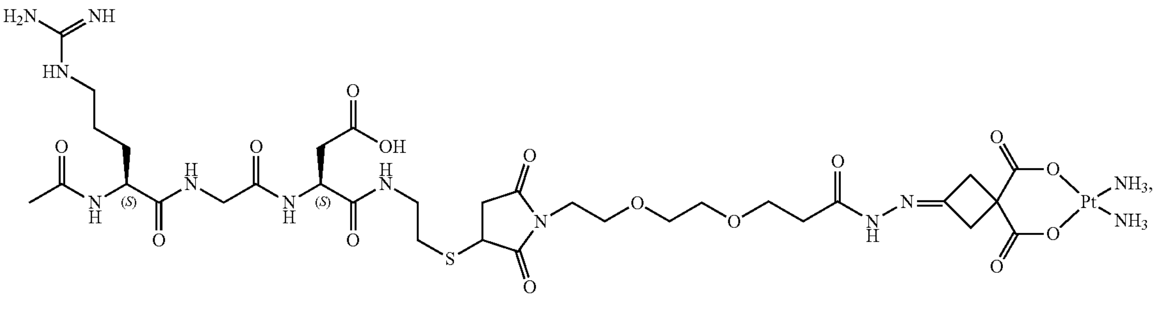

-continued
S79
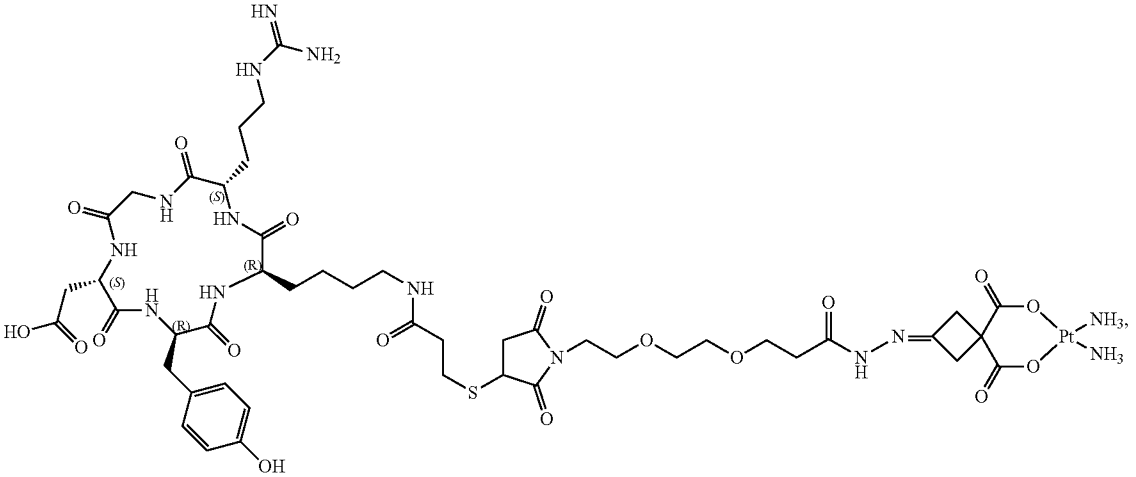
S81
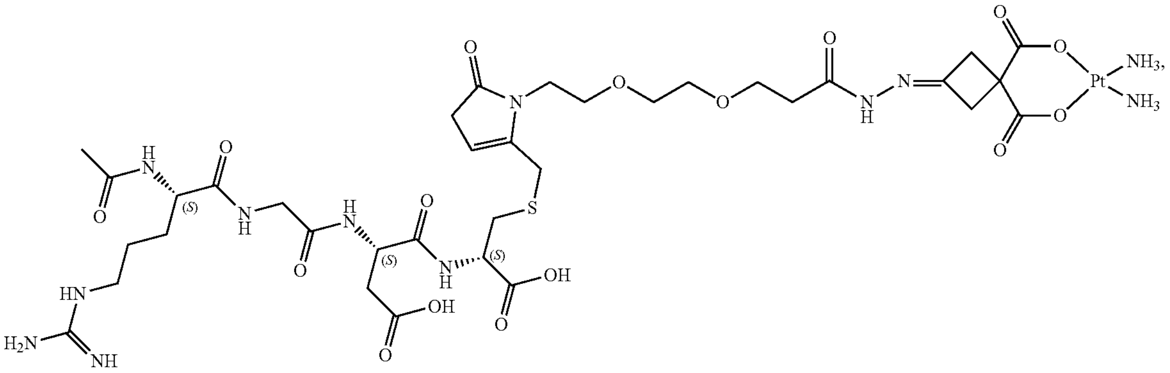
S82
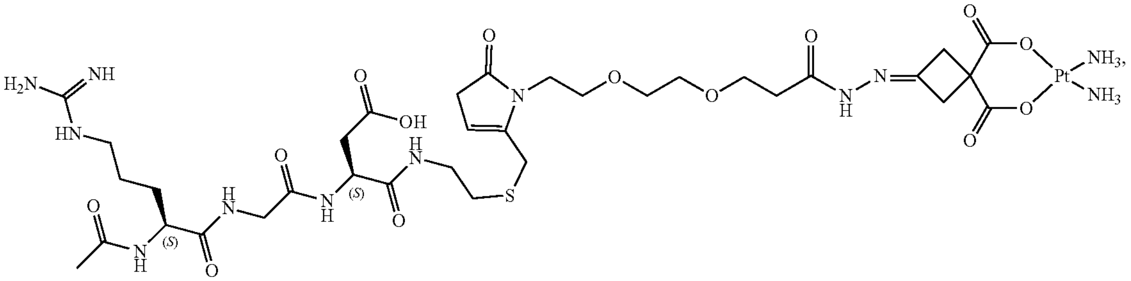
S83
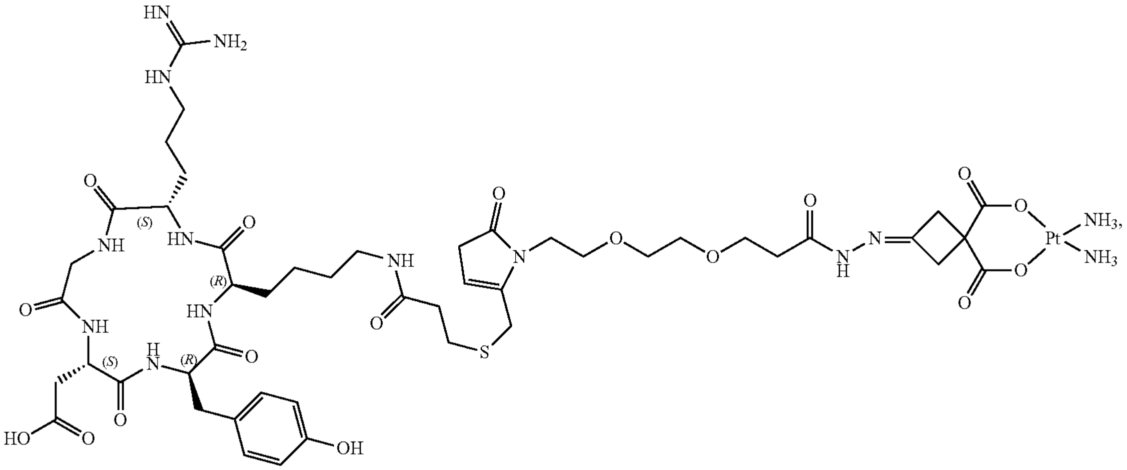

-continued

S84

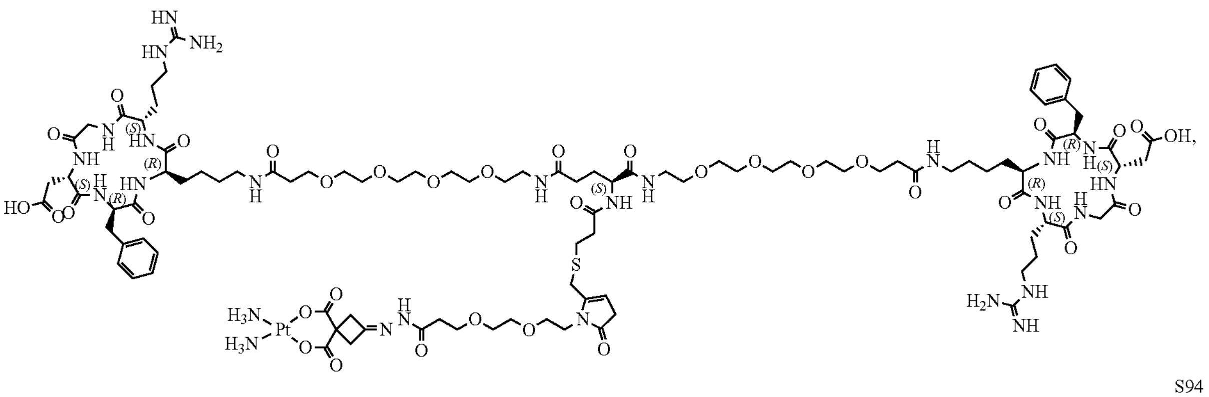

S94

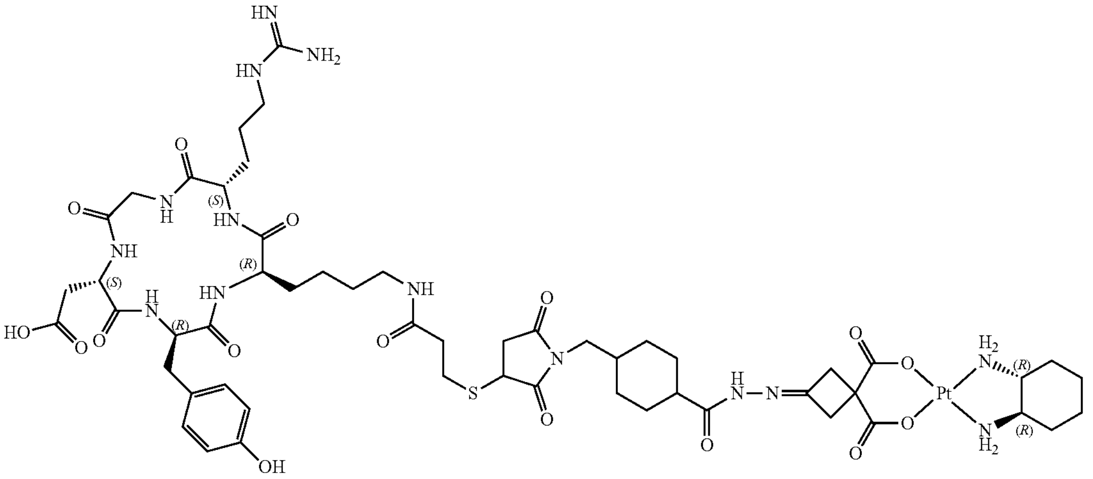

or

S96

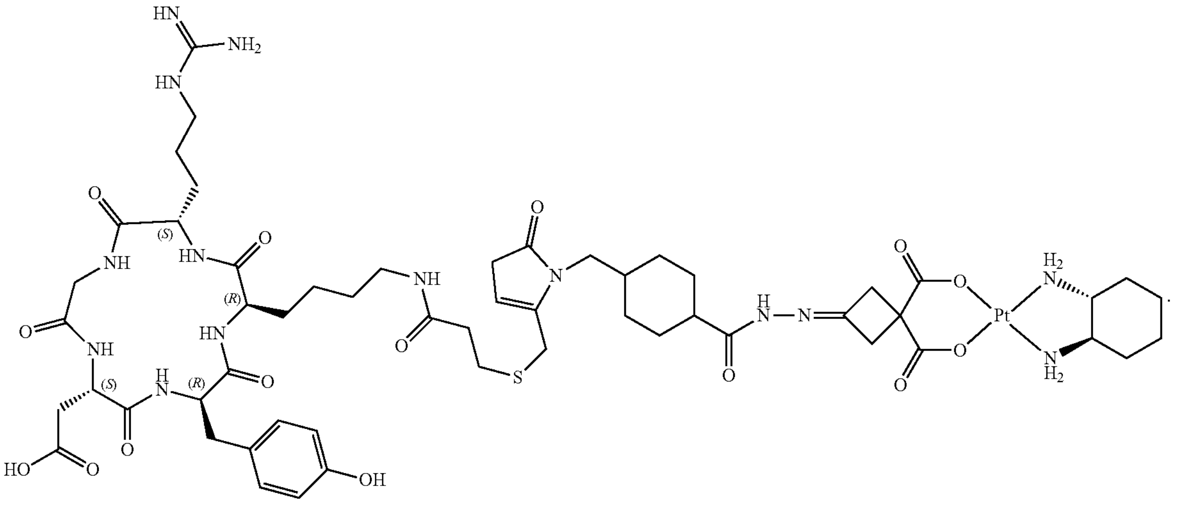

8. A pharmaceutical composition, comprising the compound represented by formula (I) or the pharmaceutically acceptable salt thereof as claimed in claim 1 and a pharmaceutically acceptable carrier.

9. A method for treating cancer, comprising administering a therapeutically effective amount of the compound represented by formula (I) or the pharmaceutically acceptable salt thereof as claimed in claim 1 to a patient, wherein, the compound represented by the formula (I) or the pharmaceutically acceptable salt is administered in combination with an anticancer medicament and/or in combination with radiotherapy and/or immunotherapy; the cancer is colorectal cancer, colon cancer, pancreatic cancer, lung cancer, non-small cell lung cancer, ovarian cancer, cervical cancer, melanoma, head and/or neck cancer, or head and neck squamous cell carcinoma.

10. A method for treating cancer, comprising administering a therapeutically effective amount of the compound represented by formula (I) or the pharmaceutically acceptable salt thereof as claimed in claim 1 to a patient; the cancer is colorectal cancer, colon cancer, pancreatic cancer, lung cancer, non-small cell lung cancer, ovarian cancer, cervical cancer, melanoma, head and/or neck cancer, or head and neck squamous cell carcinoma.

11. The compound represented by formula (I) or the pharmaceutically acceptable salt thereof as claimed in claim 1, wherein, the antibody is an anti-folate receptor a antibody, an anti-mesothelin antibody, an anti-Her2 antibody, an anti-EGFR antibody, an anti-VEGFR antibody, an anti-CD20 antibody, an anti-CD22 antibody, an anti-CD28 antibody, an anti-CD33 antibody or an anti-BR96 antibody.

12. The compound represented by formula (I) or the pharmaceutically acceptable salt thereof as claimed in claim 4, wherein, the integrin receptor is $\alpha v\beta 3$, $\alpha v\beta 6$ or $\alpha 5\beta 1$.

13. The compound represented by formula (I) or the pharmaceutically acceptable salt thereof as claimed in claim 1, wherein, $R_4$ is selected from:

R4-12

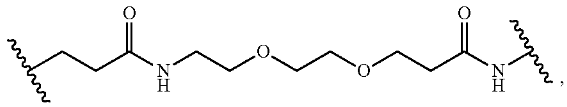

R4-8

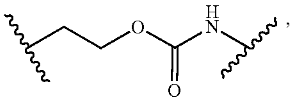

R4-10

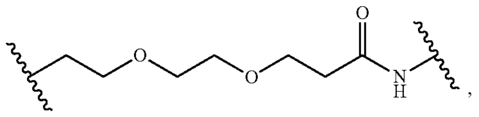

R4-15

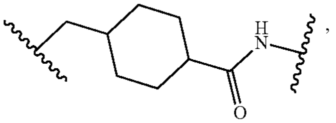

R4-16

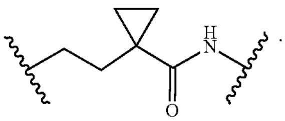

14. The compound represented by formula (I) or the pharmaceutically acceptable salt thereof as claimed in claim 1, wherein, $R_4$ is $C_{1-12}$ alkylcarbonylamino.

15. The compound represented by formula (I) or the pharmaceutically acceptable salt thereof as claimed in claim 1, wherein, $R_5$ is human serum albumin HSA.

16. The compound represented by formula (I) or the pharmaceutically acceptable salt thereof as claimed in claim 1, wherein: the general formula of this series of platinum compounds is:

I-A1

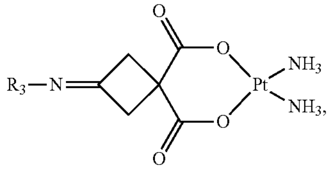

I-A2

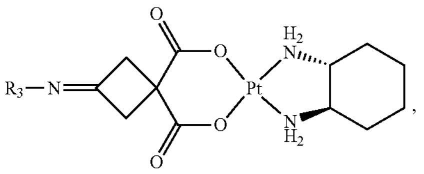

I-A3

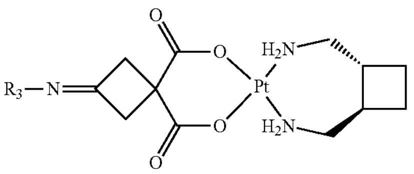

or

I-A4

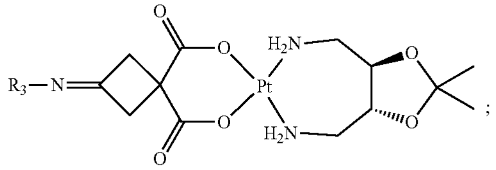

$R_3$ is the following structure:

R3-1

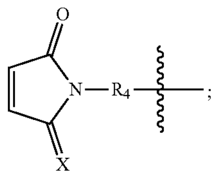

R3-2

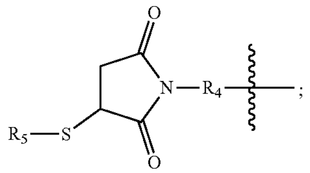

or

R3-3

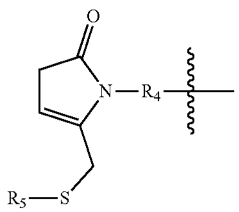

wherein, X is $CH_2$ or O;

$R_4$ is $C_{1-12}$ alkylcarbonylamino;

$R_5$ is human serum albumin HSA; an anti-folate receptor a antibody, an anti-mesothelin antibody, an anti-Her2 antibody, an anti-EGFR antibody, an anti-VEGFR antibody, an anti-CD20 antibody, an anti-CD22 antibody, an anti-CD28 antibody, an anti-CD33 antibody or an anti-BR96 antibody.

17. The compound represented by formula (I) or the pharmaceutically acceptable salt thereof as claimed in claim 1, wherein: the general formula of this series of platinum compounds is:

I-A1

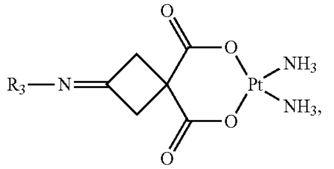

I-A2

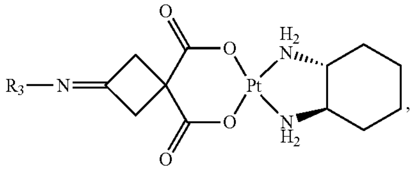

I-A3

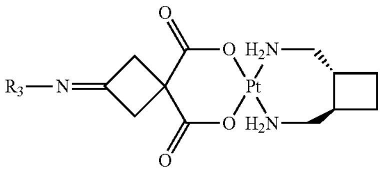

or

I-A4

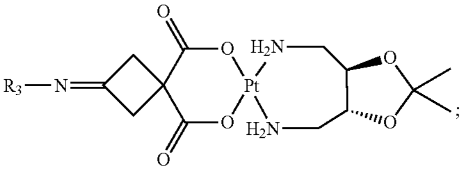

$R_3$ is the following structure:

R3-1

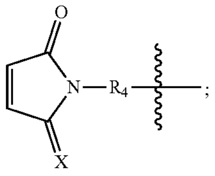

R3-2

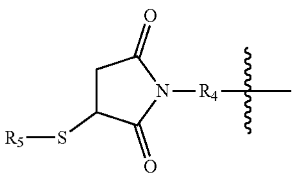

or

R3-3

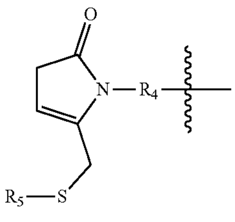

wherein, X is $CH_2$ or O;

$R_4$ is $C_{1-12}$ alkylcarbonylamino;

$R_5$ is the molecule that is able to specifically bind to the tumor cell surface integrin receptor.

18. The compound represented by formula (I) or the pharmaceutically acceptable salt thereof as claimed in claim 1, wherein: the general formula of this series of platinum compounds is:

I-A1

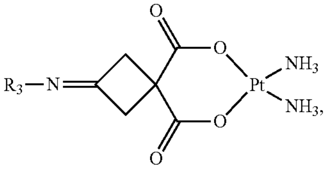

I-A2

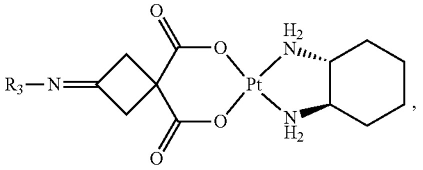

I-A3

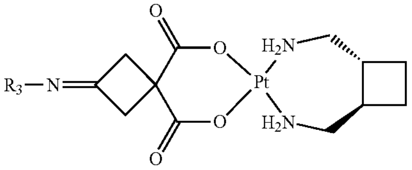

or

I-A4

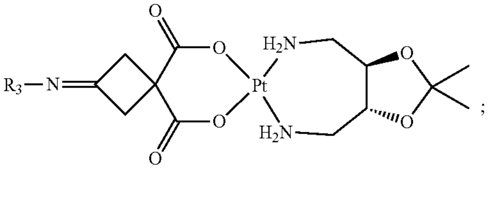

$R_3$ is the following structure:

R3-1

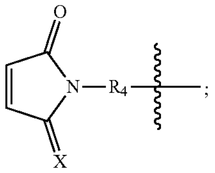

R3-2

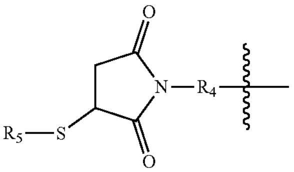

or

-continued

R3-3

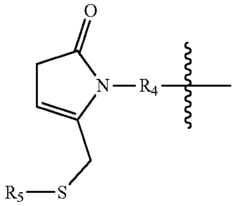

wherein, X is $CH_2$ or O;
$R_4$ is selected from:

R4-12

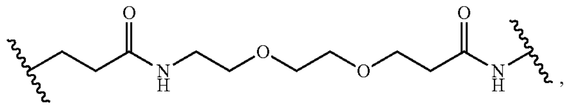

R4-8

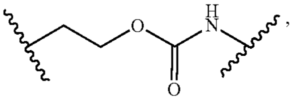

-continued

R4-10

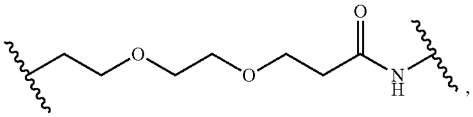

R4-15

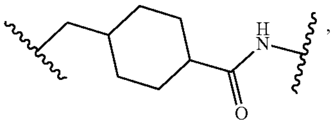

R4-16

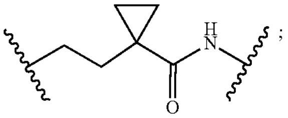

$R_5$ is human serum albumin HSA; an anti-folate receptor a antibody, an anti-mesothelin antibody, an anti-Her2 antibody, an anti-EGFR antibody, an anti-VEGFR antibody, an anti-CD20 antibody, an anti-CD22 antibody, an anti-CD28 antibody, an anti-CD33 antibody or an anti-BR96 antibody.

19. The compound represented by formula (I) or the pharmaceutically acceptable salt thereof as claimed in claim 1, wherein, the compound represented by formula (I) is:

S17

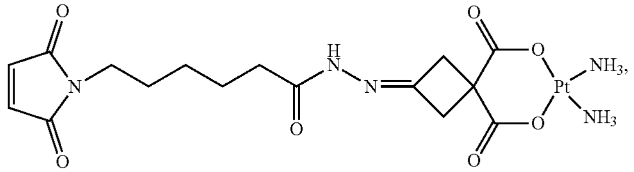

S47

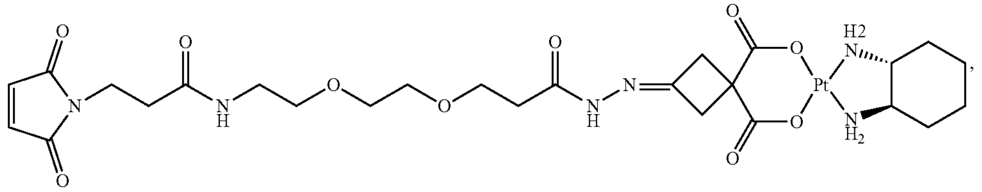

-continued
S72
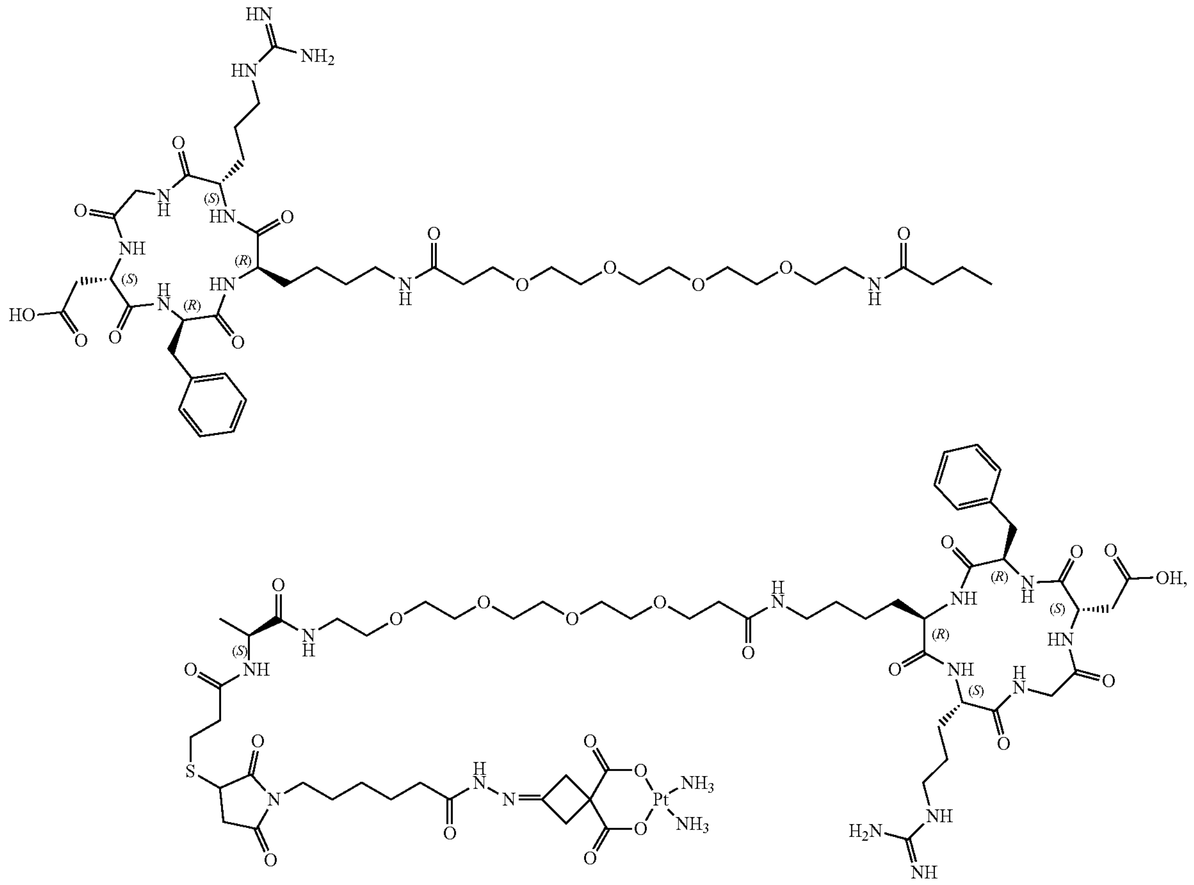
,

-continued
S80
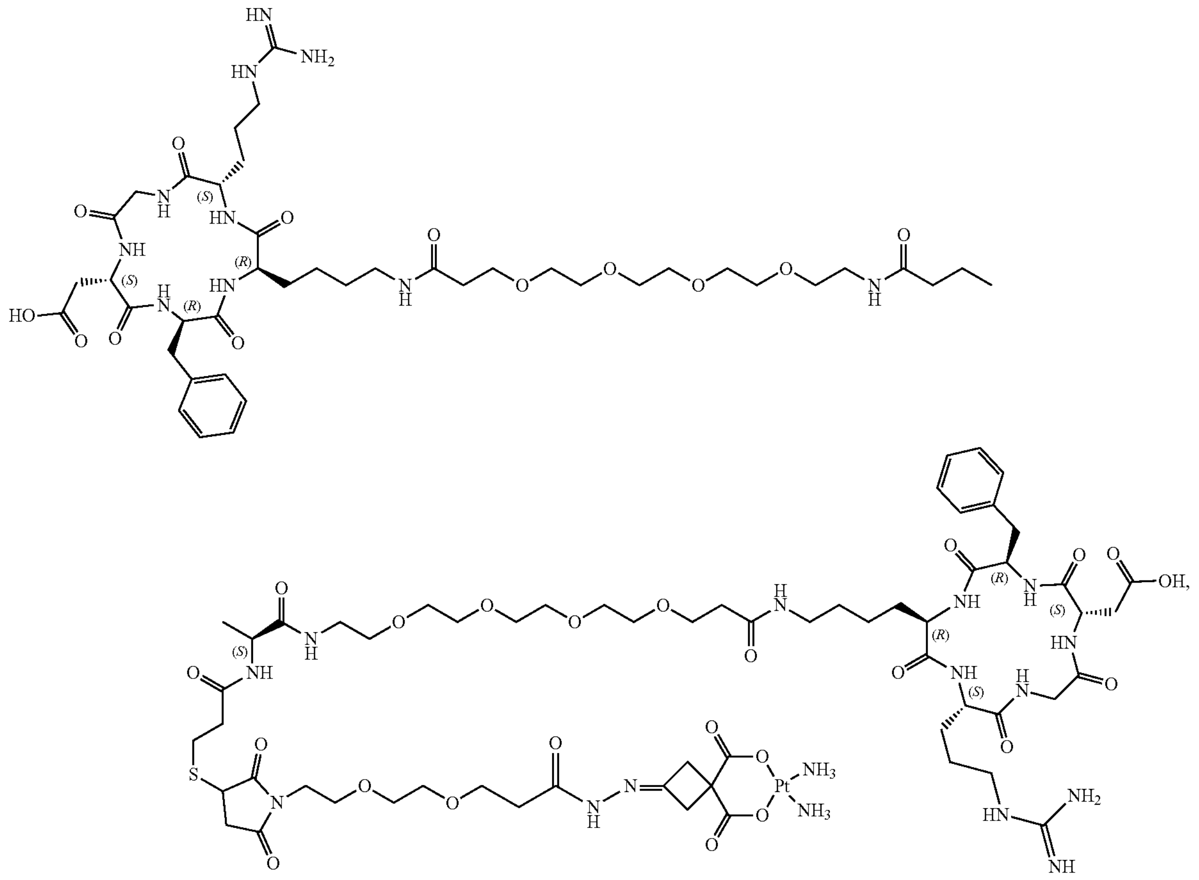

-continued
S95
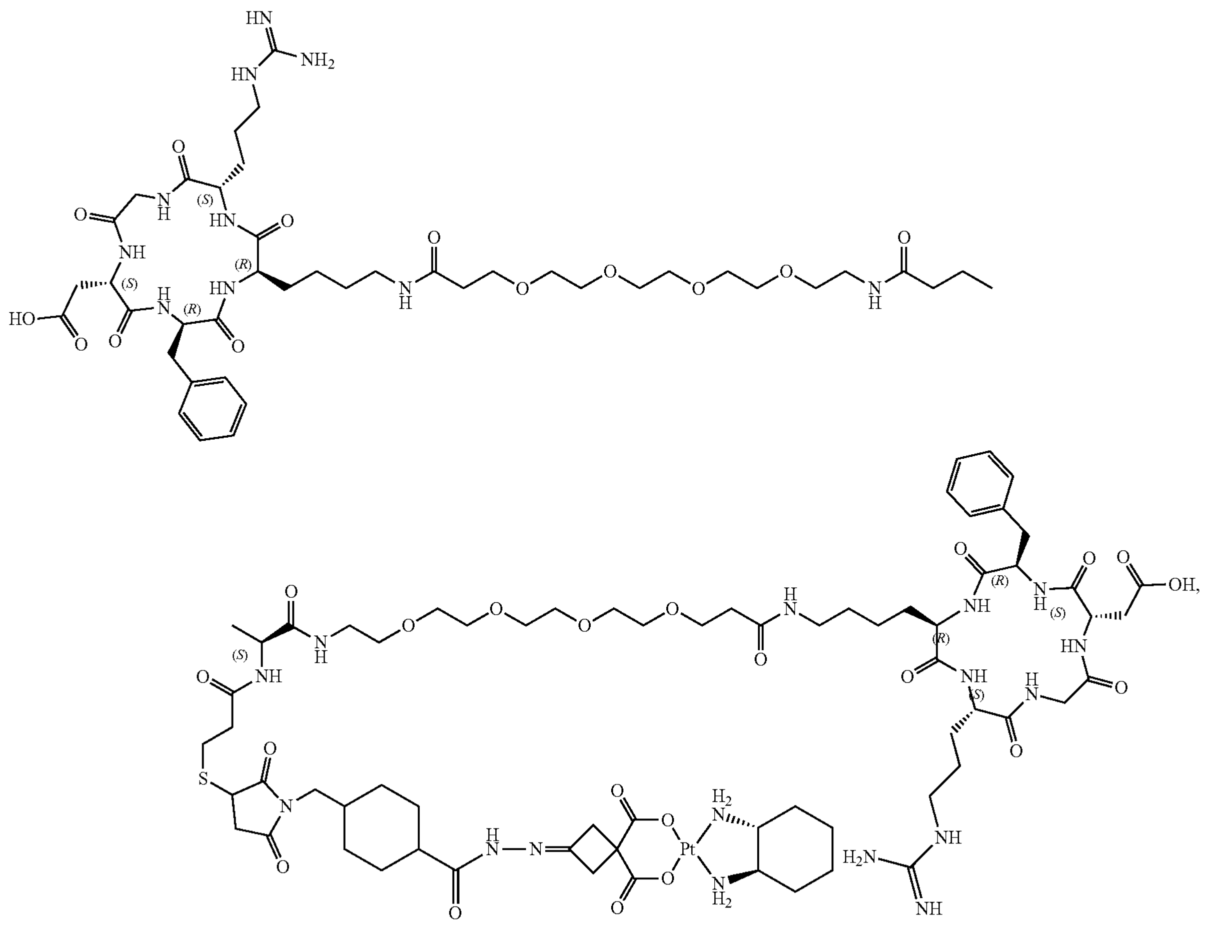

-continued
S97
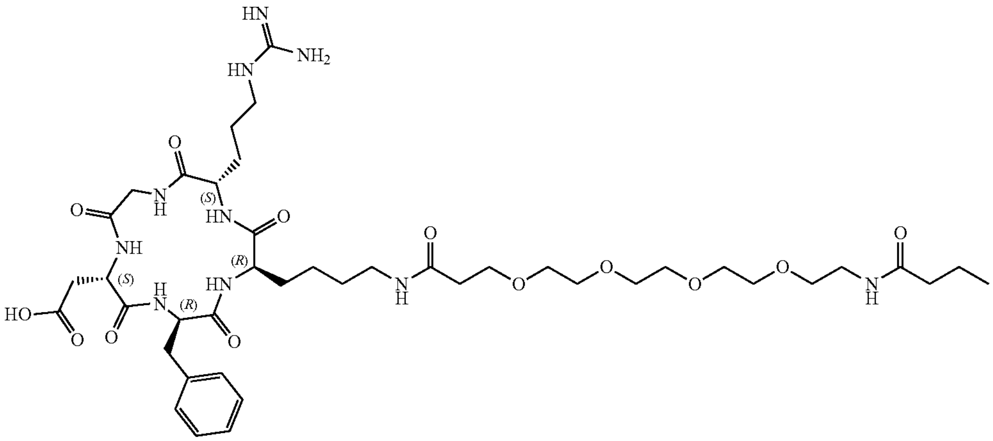
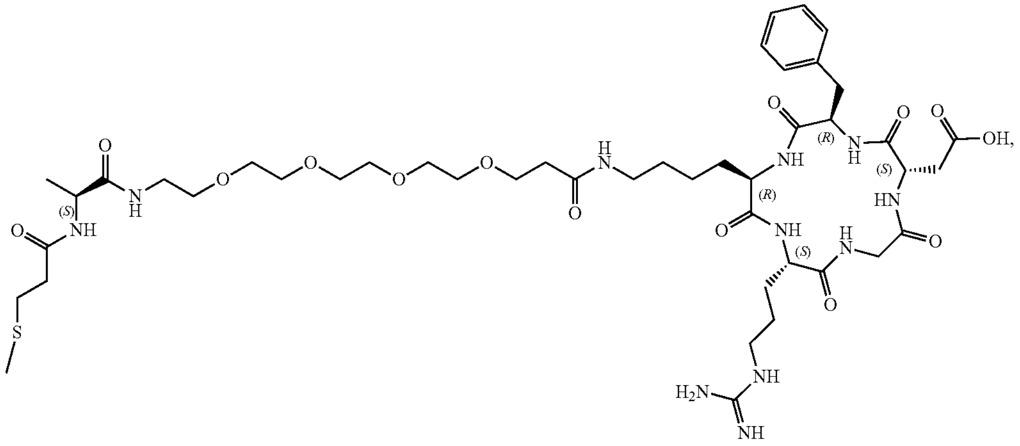
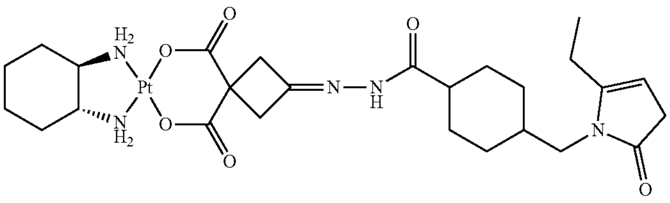
* * * * *